(12) United States Patent
Ashton et al.

(10) Patent No.: US 11,767,508 B2
(45) Date of Patent: Sep. 26, 2023

(54) METHODS AND CULTURE SUBSTRATES FOR CONTROLLED INDUCTION OF BIOMIMETIC NEURAL TISSUES COMPRISING SINGULAR ROSETTE STRUCTURES

(71) Applicant: Wisconsin Alumni Research Foundation, Madison, WI (US)

(72) Inventors: Randolph Scott Ashton, Madison, WI (US); Gavin T. Knight, Coral Springs, FL (US)

(73) Assignee: Wisconsin Alumni Research Foundation, Madison, WI (US)

( * ) Notice: Subject to any disclaimer, the term of this patent is extended or adjusted under 35 U.S.C. 154(b) by 449 days.

(21) Appl. No.: 16/044,236

(22) Filed: Jul. 24, 2018

(65) Prior Publication Data

US 2019/0024046 A1    Jan. 24, 2019

Related U.S. Application Data

(60) Provisional application No. 62/536,023, filed on Jul. 24, 2017.

(51) Int. Cl.
*C12N 5/0793* (2010.01)

(52) U.S. Cl.
CPC ...... *C12N 5/0619* (2013.01); *C12N 2501/115* (2013.01); *C12N 2501/119* (2013.01); *C12N 2501/385* (2013.01); *C12N 2501/41* (2013.01); *C12N 2501/415* (2013.01); *C12N 2501/727* (2013.01); *C12N 2501/999* (2013.01); *C12N 2506/02* (2013.01); *C12N 2506/03* (2013.01); *C12N 2513/00* (2013.01); *C12N 2533/30* (2013.01); *C12N 2533/90* (2013.01); *C12N 2535/00* (2013.01)

(58) Field of Classification Search
CPC .................................................. C12N 5/0619
See application file for complete search history.

(56) References Cited

U.S. PATENT DOCUMENTS

| | | |
|---|---|---|
| 2008/0171385 A1 | 7/2008 | Bergendahl |
| 2014/0134732 A1 | 5/2014 | Ashton |
| 2016/0068806 A1 | 3/2016 | Ashton |
| 2017/0283774 A1 | 10/2017 | Lippmann |

OTHER PUBLICATIONS

Knight et al. (2015, Chem. Commun., vol. 51, pp. 5238-5241) (Year: 2015).*
Lippmann et al. (2014, Stem Cells, vol. 32, pp. 1032-1042). (Year: 2014).*
Lippmann et al. (2015, Stem Cell Reports, vol. 4, pp. 632-644). (Year: 2015).*
Shaker et al., 2015, Stem Cell and Development, vol. 24(10, pp. 1171-1181 (Year: 2015).*
Copp et al. (2003, Nature Reviews Genetics, vol. 4, pp. 784-793) (Year: 2003).*
Ashton, R., et al., Chemically defined differentiation of human pluripotent stem cells to hindbrain and spinal cord neural stem cells with defined regional identities, Protocol Exchange. (2015). doi:10.1038/protex.2015.076.
Baba et al. (2005), Constitutively active ß-catenin confers multilineage differentiation potential on lymphoid and myeloid progenitors Immunity 23(6):599-609.
Briscoe, J., et al., A Homeodomain Protein Code Specifies Progenitor Cell Identity and Neuronal Fate in the Ventral Neural Tube, Cell. 101 (2000) 435-445. doi:10.1016/S0092-8674(00)80853-3.
Chambers, S.M. et al., Highly efficient neural conversion of human ES and iPS cells by dual inhibition of SMAD signaling, Nature Biotechnology. 27 (2009) 275-280. doi:10.1038/nbt.1529.
Chen et al., Chemically defined conditions for human iPS cell derivation and culture (2011) Nature Methods. 8(4), 424-429.
Cogliatti, Diplomyelia—Caudal Duplication of the Neural-Tube in Mice, Teratology. 34 (1986) 343-352. doi:10.1002/tera.1420340314.
Davidson, L.A., et al., Neural tube closure in Xenopus laevis involves medial migration, directed protrusive activity, cell intercalation and convergent extension, Development. 126 (1999) 4547-4556.
Dessaud, E., et al., Interpretation of the sonic hedgehog morphogen gradient by a temporal adaptation mechanism, Nature. 450 (2007) 717-720. doi:10.1038/nature06347.
Ebert et al., Induced pluripotent stem cells from a spinal muscular atrophy patient Nature 457(7227):277-80 (2009).
Eiraku, M, et al., Self-organized formation of polarized cortical tissues from ESCs and its active manipulation by extrinsic signals, Cell Stem Cell. 3 (2008) 519-532. doi:10 1016/j.stem.2008.09.002.
Etoc, F., et al., A Balance between Secreted Inhibitors and Edge Sensing Controls Gastruloid Self-Organization, Developmental Cell. 39 (2016) 302-315. doi:10.1016/j.devcel.2016.09.016.
Hagen et al. (2002), Expression and characterization of GSK-3 mutants and their effect on ß-catenin phosphorylation in intact cells J. Biol. Chem., 277(26):23330-23335.

(Continued)

*Primary Examiner* — Anoop K Singh
*Assistant Examiner* — David A Montanari
(74) *Attorney, Agent, or Firm* — McDonnell Boehnen Hulbert & Berghoff LLP

(57) ABSTRACT

Described herein are methods, compositions, and kits for directed differentiation of human pluripotent stem cells, neuromesodermal progenitors, and neural stem cells into biomimetic neural tissues comprising one or more rosette structures. Preferably, the methods provided herein direct differentiation of human pluripotent stem cells, neuromesodermal progenitors, and neural stem cells into biomimetic neural tissues comprising a singular neural rosette structure that is comparable to at least a portion of the developing human neural tube. Also described are engineered neural tissue preparations comprising biomimetic neural tissues comprising a singular rosette structure having regional neural progenitor phenotypes.

18 Claims, 20 Drawing Sheets
(18 of 20 Drawing Sheet(s) Filed in Color)

(56) References Cited

OTHER PUBLICATIONS

Howden et al., Genetic correction and analysis of induced pluripotent stem cells from a patient with gyrate atrophy. Proc. Natl. Acad. Sci. U. S. A. 108(16):6537-42 (2011).
Knight, G.T., et al., Micropatterned, clickable culture substrates enable in situ spatiotemporal control of human PSC-derived neural tissue morphology, Chem. Commun. 51 (2015) 5238-5241. doi:10.1039/C4CC08665A.
Lancaster, et al., Cerebral organoids model human brain development and microcephaly, Nature. 501 (2013) 373-379. doi:110.1038/nature12517.
Lancaster, et al., Guided self-organization recapitulates tissue architecture in a bioengineered brain organoid model, bioRxiv. (2016).
Lancaster, et al., Organogenesis in a dish: modeling development and disease using organoid technologies, Science. 345 (2014) 1247125-1247125. doi:10.1126/science.1247125.
Lee, C-T., et al., CYP3A5 Mediates Effects of Cocaine on Human Neocorticogenesis: Studies using an In Vitro 3D Self-Organized hPSC Model with a Single Cortex-Like Unit, Neuropsychopharmacology. 42 (2017) 774-784. doi:10.1038/npp.2016.156.
Lippmann, E.S., et al., Defined human pluripotent stem cell culture enables highly efficient neuroepithelium derivation without small molecule inhibitors, Stem Cells. 32 (2014) 1032-1042. doi:10.1002/stem.1622.
Lippmann, E.S., et al., Deterministic HOX patterning in human pluripotent stem cell-derived neuroectoderm, Stem Cell Reports. 4 (2015) 632-644. doi:10.1016/j.stemcr.2015.02.018.
Marti-Figueroa, et al., The case for applying tissue engineering methodologies to instruct human organoid morphogenesis, Acta Biomaterialia. 54 (2017) 35-44. doi:10.1016/j.actbio.2017.03.023.
Meinhardt, A., et al., 3D reconstitution of the patterned neural tube from embryonic stem cells, Stem Cell Reports. 3 (2014) 987-999. doi:10.1016/j.stemcr.2014.09.020.
Nakano, et al., Self-Formation of Optic Cups and Storable Stratified Neural Retina from Human ESCs, Cell Stem Cell. 10 (2012) 771-785. doi:10.1016/j.stem.2012.05.009.
Nelson, C.M., et al., Emergent patterns of growth controlled by multicellular form and mechanics, Proc. Natl. Acad. Sci. U.S.a. 102 (2005) 11594-11599. doi:10.1073/pnas.0502575102.
Nishimura, T., et al., Planar cell polarity links axes of spatial dynamics in neural-tube closure, Cell. 149 (2012) 1084-1097. doi:10.1016/j.cell.2012.04.021.
Nordström, U., et al., An Early Role for Wnt Signaling in Specifying Neural Patterns of Cdx and Hox Gene Expression and Motor Neuron Subtype Identity, PLoS Biol. 4 (2006) e252. doi:10.1371/journal.pbio.0040252.sg003.
Philippidou, P. et al., Hox Genes: Choreographers in Neural Development, Architects of Circuit Organization, Neuron. 80 (2013) 12-34. doi:10.1016/j.neuron.2013.09.020.
Ranga, A., et al., 3D niche microarrays for systems-level analyses of cell fate, Nature Communications. 5 (2014) 4324. doi:10.1038/ncomms5324.
Sasai, Next-generation regenerative medicine: organogenesis from stem cells in 3D culture, Cell Stem Cell. 12 (2013) 520-530. doi:10.1016/j.stem.2013 04.009.
Sha, J. et al., Sequential Nucleophilic Substitutions Permit Orthogonal Click Functionalization of Multicomponent PEG Brushes, Biomacromolecules. 14 (2013) 3294-3303. doi:10.1021/bm400900r.
Shi, Y., et al., Human cerebral cortex development from pluripotent stem cells to functional excitatory synapses, Nat. Neurosci. 15 (2012) 477-86-S1. doi:10.1038/nn.3041.
Spencer, Theoretical and analytical embryology of conjoined twins: part I: embryogenesis, Clin Anat. 13 (2000) 36-53.
Stewart et al., Comparative RNA-seq Analysis in the Unsequenced Axolotl: The Oncogene Burst Highlights Early Gene Expression in the Blastema, PLoS Comput. Biol. 9:e1002936 (2013).
Testoni, et al., Imaging diagnosis—ultrasonographic diagnosis of diplomyelia in a calf, Veterinary Radiology . . . (2010). doi:10.1111/j.1740-8261.2010.01717.x.
Thomson, J.A., Embryonic Stem Cell Lines Derived from Human Blastocysts, Science. 282 (1998) 1145-1147. doi:10.1126/science 282.5391.1145.
Timmer, J.R., et al., BMP signaling patterns the dorsal and intermediate neural tube via regulation of homeobox and helix-loop-helix transcription factors, Development. 129 (2002) 2459-2472.
Warmflash, A., et al., A method to recapitulate early embryonic spatial patterning in human embryonic stem cells, Nat Meth. 11 (2014) 847-854. doi:10.1038/nmeth.3016.
Watanabe K, et al., "A Rock inhibitor permits survival of dissociated human embryonic stem cells," Nat. Biotechnol. 25:681-686 (2007).
Watson, et al., An in vivo model of human small intestine using pluripotent stem cells, Nat. Med. 20 (2014) 1310-1314. doi:10.1038/nm.3737.
Workman, et al., Engineered human pluripotent-stem-cell-derived intestinal tissues with a functional enteric nervous system, Nat. Med. 23 (2017) 49-59. doi:10.1038/nm.4233.
Yu et al., Induced Pluripotent Stem Cell Lines Derived from Human Somatic Cells, Science 318:1917-1920 (2007).
Yu et al., Human Induced Pluripotent Stem Cells Free of Vector and Transgene Sequences Science 324 (5928):797-801 (2009).
Zhang, et al., Cortical neural precursors inhibit their own differentiation via N-cadherin maintenance of beta-catenin signaling, Developmental Cell. 18 (2010) 472-479. doi:10.1016/j.devcel.2009.12.025.
Zhang, S.C., et al., In vitro differentiation of transplantable neural precursors from human embryonic stem cells, Nature Biotechnology. 19 (2001) 1129-1133. do:10.1038/nbt1201-1129.
Zhang, X, et al., Pax6 is a human neuroectodemn cell fate determinant, Cell Stem Cell. 7 (2010) 90-100. doi: 10.1016/j.stem.2010.04.017.
Knight, G. T., et al., Engineering induction of singular neural rosette emergence within hPSC-derived tissues. eLIFE. (2018)7:e37549, https://doi.org/10.7554/eLife.37549.001.

\* cited by examiner

FIGS. 3A-3F
A
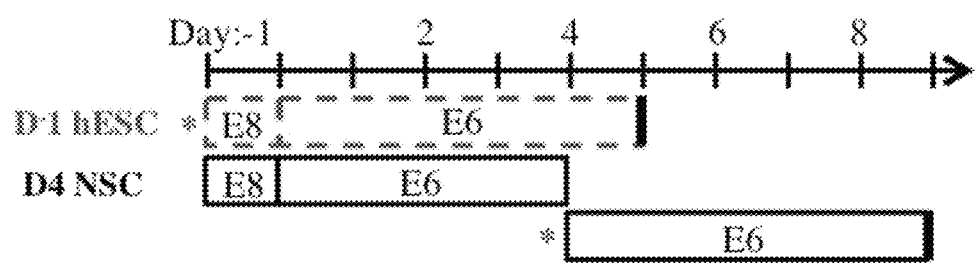
B
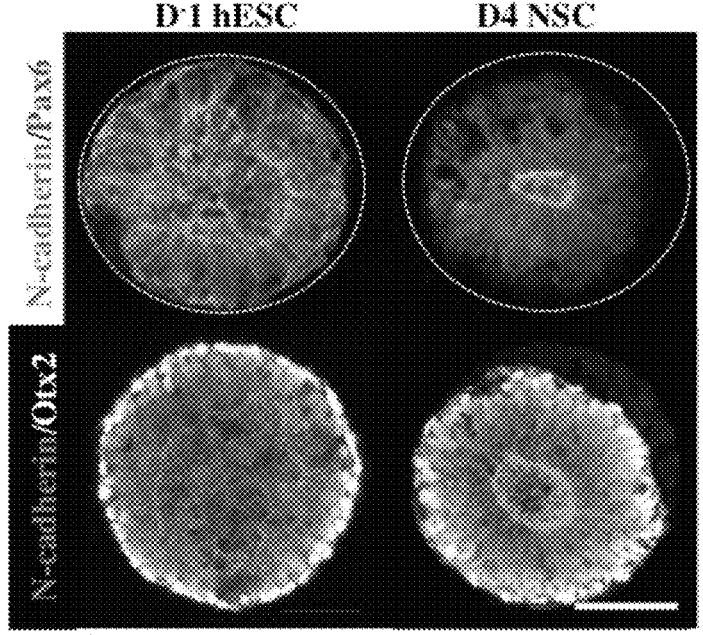
C
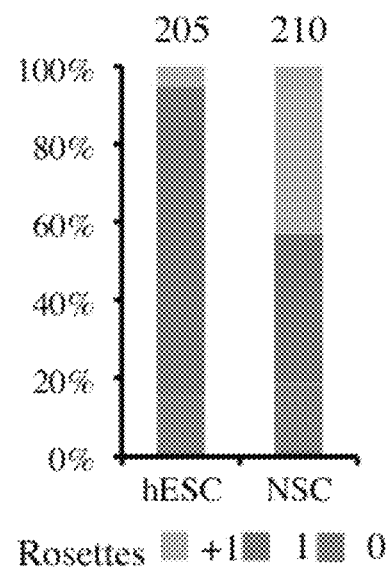

FIGS. 3A-3F, CONTINUED
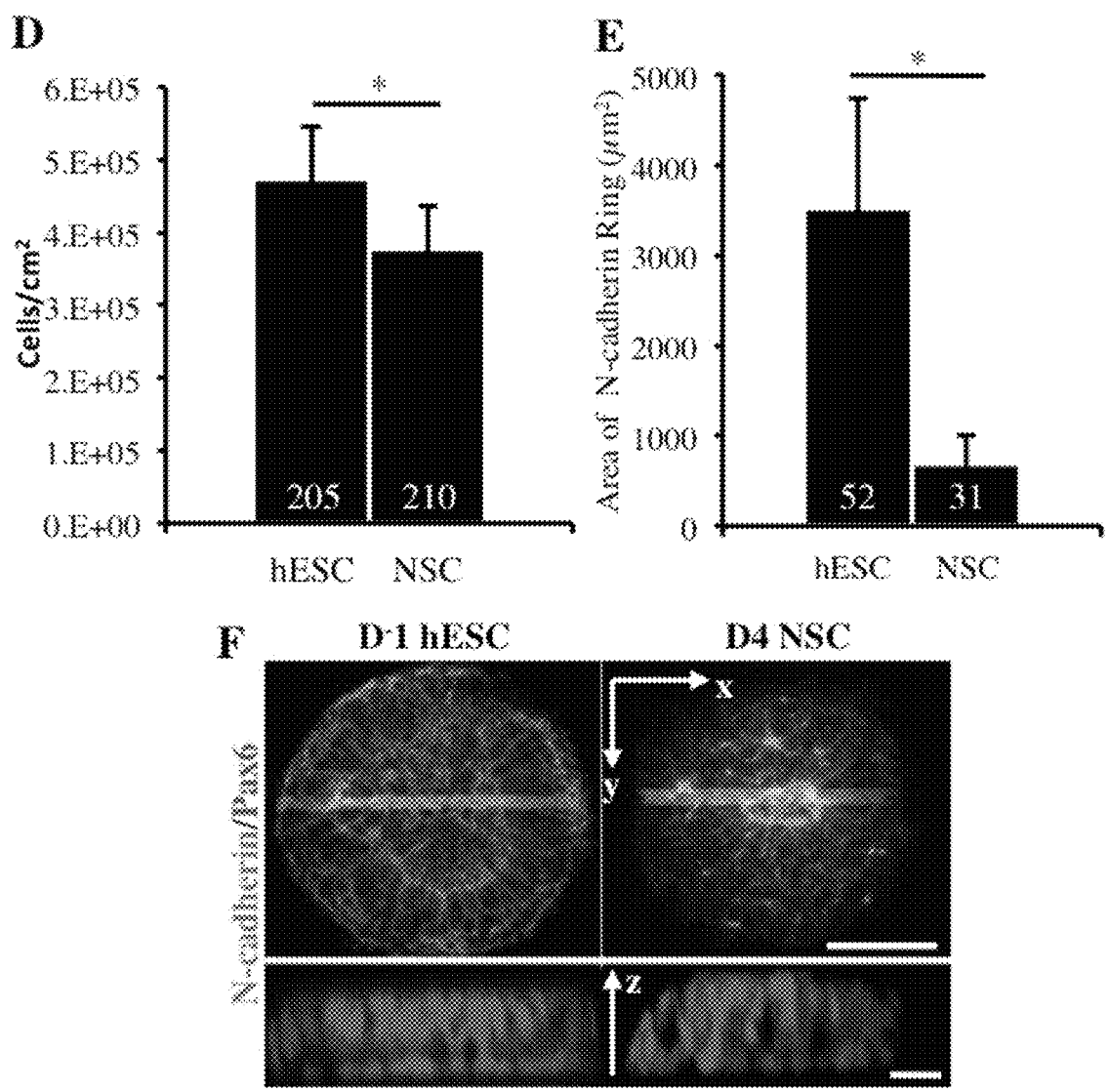

FIGS. 4A-4E, CONTINUED
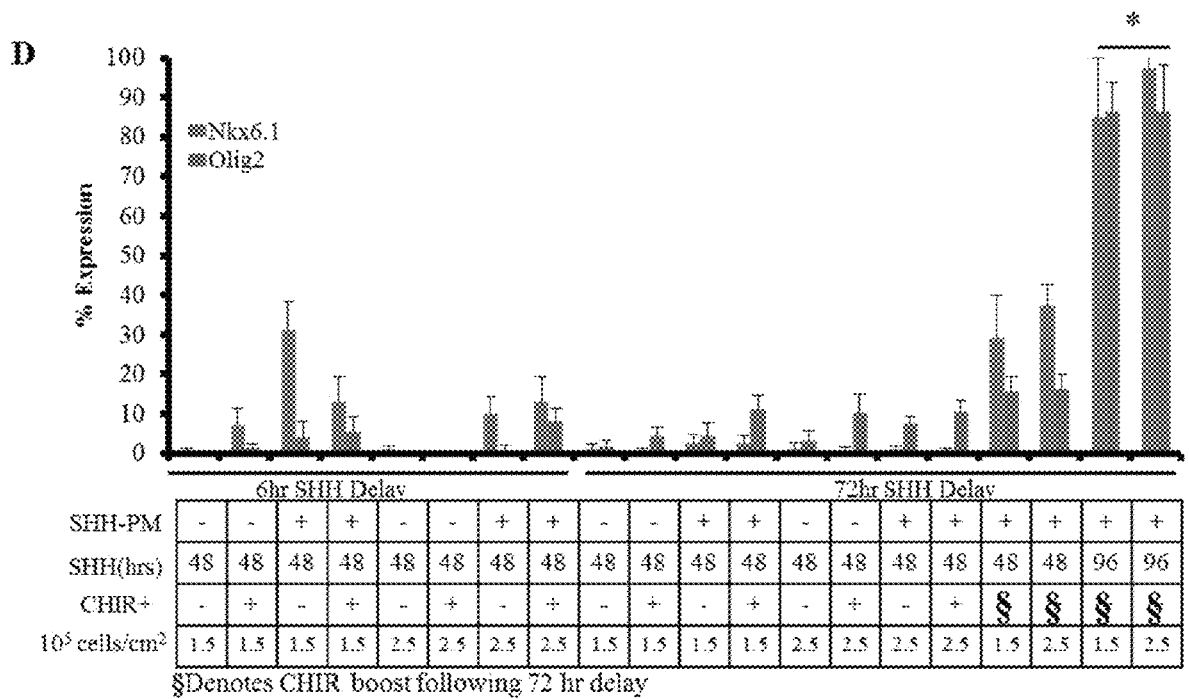
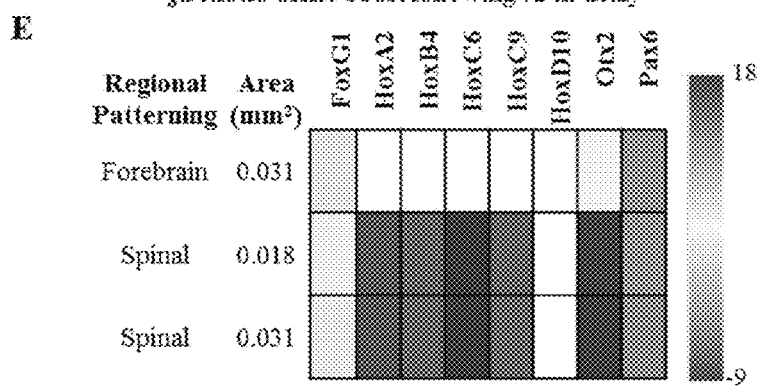

A

B

FIGS. 10A-10D, CONTINUED
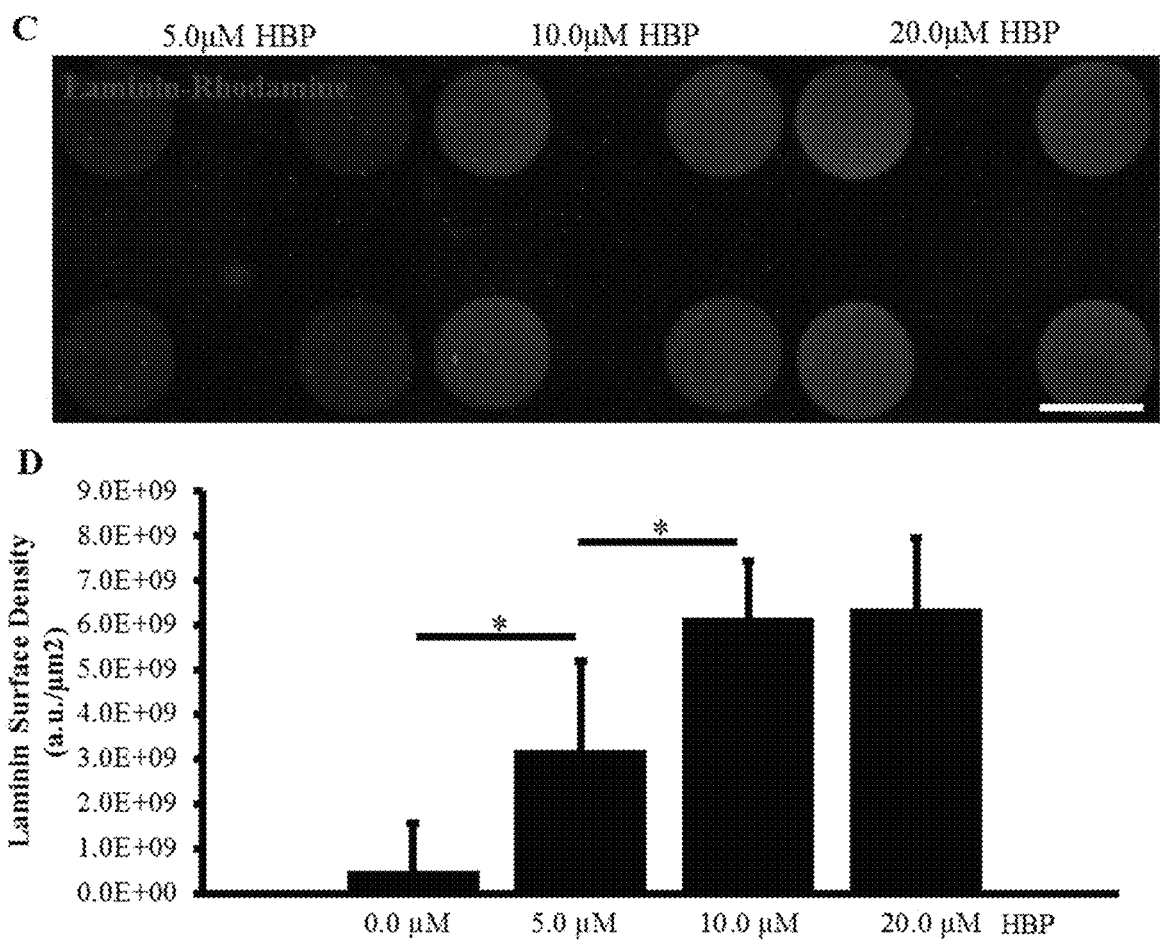

FIGS. 11A-11G, CONTINUED
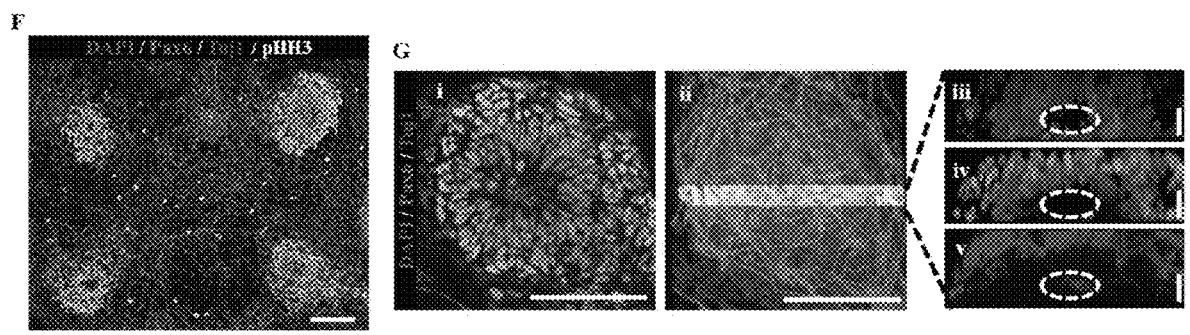

| | Error | Stdev | False + | Stdev | False - | Stdev |
|---|---|---|---|---|---|---|
| Polarization | | | | | | |
| Human | 21.19% | 3.35% | 13.56% | 6.94% | 7.63% | 3.81% |
| Machine Learning | 14.35% | | 7.59% | | 6.75% | |
| Rosette | | | | | | |
| Human | 13.05% | 2.74% | 9.15% | 4.06% | 3.90% | 1.51% |
| Machine Learning | 8.86% | | 3.38% | | 5.49% | |

B.

| | Error | Stdev | False + | Stdev | False - | Stdev |
|---|---|---|---|---|---|---|
| Polarization | | | | | | |
| Human | 19.05% | 14.61% | 16.19% | 16.07% | 1.63% | 1.77% |
| Machine Learning | 20.27% | | 12.16% | | 8.11% | |
| Rosette | | | | | | |
| Human | 9.93% | 6.96% | 9.39% | 7.40% | 0.54% | 0.75% |
| Machine Learning | 19.59% | | 16.89% | | 2.70% | |

METHODS AND CULTURE SUBSTRATES FOR CONTROLLED INDUCTION OF BIOMIMETIC NEURAL TISSUES COMPRISING SINGULAR ROSETTE STRUCTURES

CROSS-REFERENCE TO RELATED APPLICATIONS

This application claims priority to U.S. Provisional Application No. 62/536,023, filed Jul. 24, 2017, which is incorporated herein by reference in its entirety.

STATEMENT REGARDING FEDERALLY SPONSORED RESEARCH OR DEVELOPMENT

This invention was made with government support under NS082618 awarded by National Institutes of Health and 83573701 awarded by Environmental Protection Agency. The government has certain rights in the invention.

BACKGROUND

Human pluripotent stem cells (hPSCs), including human embryonic stem cells (hESCs) and induced pluripotent stem cells (hiPSCs), are an incredibly powerful tool for studying human development and disease and may one day serve as a cell source for regenerative cell and tissue therapies. Human pluripotent stem cells (hPSCs) in two dimensional (2D) and three dimensional (3D) aggregate cultures possess the ability to spontaneously differentiate and self-organize, a.k.a. morph, into tissues, a.k.a. organoids, resembling the microscale structure and functions of primordial organs such as the brain, eye, kidney, and gut. These organoids provide unprecedented biomimicry for studying development and disease in vitro and within a human genetic context. However, while spontaneous morphogenesis enables organoid derivation, this same property results in highly non-standardized tissue products.

The current gold standard of central nervous system (CNS) organoid generation involves long-term 3D bioreactor culture of hPSC-derived neural stem cell (NSC) aggregates. The NSCs spontaneously morph into organoids containing unprecedented microscale formations of primordial CNS structures, e.g. cortical, retinal, and cerebellar tissues. However, the organoid's macroscale anatomy, which includes macroscale morphology, cytoarchitecture (i.e., the spatial organization of different cell and tissue phenotypes), and cellular composition, are inconsistent and non-mimetic of the highly-stereotyped CNS. This is due to the in vitro absence of spatial and temporal cues that robustly instruct micro-thru-macroscale CNS morphogenesis in vivo, including physical limitations on tissue morphology and morphogen gradients that spatially pattern diverse cell and tissue phenotypes. For example, at the onset of organoid derivation, uncontrolled NSC morphogenesis results in random formation of numerous neural tube-like structures, a.k.a. neural rosettes, in contrast to the singular neural tube that forms the primordial anlage and organizational center of CNS morphogenesis in vivo. This results in CNS organoids containing multiple morphogenesis centers, which inevitably confounds their in vitro development and impedes macroscale biomimicry. Such shortcomings of current culture methodologies to robustly instructed controlled in vitro morphogenesis of CNS organoids limits the scalability and clinical translatability of this powerful experimental platform. Thus, there is an ongoing need for improved methods and compositions for directed differentiation of human pluripotent stem cells, neuromesodermal progenitors, and neural stem cells into anatomically biomimetic neural tissues comprising neural rosette structures exhibiting microscale cellular organization comparable to a portion of the developing human neural tube.

BRIEF SUMMARY

Described herein are methods, compositions, and kits for directed differentiation of human pluripotent stem cells, neuromesodermal progenitors, and neural stem cells into biomimetic neural tissues comprising one or more neural rosette structures. Preferably, the methods provided herein direct differentiation of Oct4$^+$/Sox2$^+$ human pluripotent stem cells (hPSCs), Oct4-/Sox2$^+$/Brachyury$^+$/Pax6+ neuromesodermal progenitors (NMPs), or Oct4-/Sox2$^+$/Brachyury-/Pax6+ neural stem cells (NSCs) into biomimetic neural tissues comprising a singular neural rosette structure comparable to a portion of the developing human neural tube.

In a first aspect, provided herein is a method of producing a micropatterned biomimetic neural tissue having a singular rosette structure in vitro. The method can comprise: (a) seeding human pluripotent stem cells (hPSCs) in the presence of a Rho kinase inhibitor onto a micropatterned substrate configured to instruct biomimetic neural morphogenesis of cells cultured thereon; (b) culturing the seeded cells of (a) on the micropatterned substrate for a first culture period of about one to two days in the presence of a first neural differentiation base medium to obtain a first cell population, wherein the first neural differentiation base medium comprises a Rho kinase inhibitor; and (c) culturing the cells of (b) for a second culture period of about 2 to about 6 days under adherent culture conditions in a second neural differentiation base medium, whereby a singular biomimetic neural tissue having a polarized rosette structure in which at least 80% of cells of the structure are Pax6+/N-cadherin+ neuroepithelial cells is produced, wherein greater than about 75% of the biomimetic neural tissue exhibits a singular rosette structure comparable to a developing human neural tube. The first neural differentiation medium can be a chemically defined medium comprising DMEM/F-12, ascorbic acid, sodium bicarbonate, selenium, insulin, transferrin, FGF2, and TGFβ1. The first neural differentiation medium can be E8 medium. The second neural differentiation medium can be a chemically defined medium comprising DMEM/F-12, ascorbic acid, sodium bicarbonate, selenium, insulin, transferrin. The second neural differentiation medium can be E6 medium. The second neural differentiation medium can further comprise one or more of an FGF and an activator of β-catenin pathway signaling. The FGF can be FGF2, FGF8a, FGF8b, FGF8f, FGF17, or FGF18. The activator of β-catenin pathway signaling can be a GSK3 kinase inhibitor. The GSK3 kinase inhibitor can be CHIR99021. In some cases, the second neural differentiation medium comprises about 100 ng/ml to about 200 ng/ml FGF8b and about 3 μM to about 9 μM CHIR99021. The second culture period can be about 5 days. In some cases, the method further comprises transiently exposing cells on the micropatterned substrate to an activator of Wnt/β-catenin signaling about 24-72 hours after plating onto the micropatterned substrate. In some cases, the method further comprises, about 24-72 hours after seeding cells onto the micropatterned substrate, exposing the seeded cells to RA and Sonic Hedgehog (SHH) or a SHH signaling agonist for about 1 to about 5 days, whereby the polarized rosette structure comprises Olig2+ motor neurons progenitors (pMNs). The SHH signaling agonist can be purmorphamine. The hPSCs can be seeded onto the micropatterned substrate at a density between about $75 \times 10^3$ cells/cm$^2$ and about $2.5 \times 10^5$ cells/cm$^2$.

In another aspect, provided herein is a method of producing a micropatterned biomimetic neural tissue having a singular rosette structure in vitro. The method can comprise culturing Oct4−/Sox2+/Brachyury−/Pax6+ neural stem cells (NSCs) on a micropatterned substrate configured to instruct biomimetic neural morphogenesis of cells cultured thereon for a culture period of about 3 to about 7 days under adherent culture conditions in the presence of a neural differentiation base medium, wherein the neural differentiation medium is a chemically defined medium comprising DMEM/F-12, ascorbic acid, sodium bicarbonate, selenium, insulin, and transferrin and is supplemented to further comprise RA and a Rho kinase inhibitor; thereby producing a singular biomimetic neural tissue having a polarized rosette structure in which at least 80% of cells of the structure are Pax6+/N-cadherin+ neuroepithelial cells, wherein greater than about 75% of the biomimetic neural tissue exhibits a singular rosette structure comparable to a developing human neural tube. The NSCs can be cultured on the micropatterned substrate for about 5 days. The neural differentiation medium can be E6. The NSCs can be seeded onto the micropatterned substrate at a density between about $75 \times 10^3$ cells/cm$^2$ and about $2.5 \times 10^5$ cells/cm$^2$.

In a further aspect, provided herein is a method of producing a micropatterned biomimetic neural tissue having a singular rosette structure in vitro. The method can comprise seeding Oct4−/Sox2+/Brachyury+/Pax6− neuromesodermal progenitors (NMPs) on a micropatterned substrate configured to instruct biomimetic neural morphogenesis of cells cultured thereon, and culturing the seeded NMPs for a culture period of about 2 to about 7 days under adherent culture conditions in the presence of a neural differentiation base medium, wherein the neural differentiation medium is supplemented with RA and a Rho kinase inhibitor; thereby producing a singular biomimetic neural tissue having a polarized rosette structure in which at least 80% of cells of the structure are Pax6+/N-cadherin+ neuroepithelial cells, wherein greater than about 75% of the biomimetic neural tissue exhibits a singular rosette structure comparable to a developing human neural tube. NMPs can be seeded onto the micropatterned substrate at a density between about $75 \times 10^3$ cells/cm$^2$ and about $2.5 \times 10^5$ cells/cm$^2$. The NMPs can be cultured on the micropatterned substrate for about 5 days. The neural differentiation medium can be E6. In some cases, the method further comprises transiently exposing cells on the micropatterned substrate to an activator of Wnt/β-catenin signaling about 24-72 hours after plating onto the micropatterned substrate. In some cases, the method further comprises, about 24-72 hours after seeding cells onto the micropatterned substrate, exposing the seeded cells to SHH or a SHH signaling agonist for about 1 to about 5 days, whereby the polarized rosette structure comprises Olig2+ spinal motor neurons progenitors (pMNs). The SHH signaling agonist can be purmorphamine. The micropatterned substrate can have a bounded geometry having at least one dimension of about 150 μm to 800 μm. The micropatterned substrate can have a circular bounded geometry having a diameter of about 150 μm to about 500 μm. The micropatterned substrate can comprise a singular or plurality of polyethylene glycol (PEG) brushes or peptide-immobilizing PEG brushes arranged in a user-defined, bounded geometry.

These and other features, objects, and advantages of the present invention will become better understood from the description that follows. In the description, reference is made to the accompanying drawings, which form a part hereof and in which there is shown by way of illustration, not limitation, embodiments of the invention. The description of preferred embodiments is not intended to limit the invention to cover all modifications, equivalents and alternatives. Reference should therefore be made to the claims recited herein for interpreting the scope of the invention.

INCORPORATION BY REFERENCE

All publications, patents, and patent applications mentioned in this specification are herein incorporated by reference to the same extent as if each individual publication, patent, and patent application was specifically and individually indicated to be incorporated by reference.

BRIEF DESCRIPTION OF THE DRAWINGS

The patent or patent application file contains at least one drawing in color. Copies of this patent or patent application publication with color drawings will be provided by the Office upon request and payment of the necessary fee.

The present invention will be better understood and features, aspects and advantages other than those set forth above will become apparent when consideration is given to the following detailed description thereof. Such detailed description makes reference to the following drawings, wherein:

FIGS. 3A-3F. (A) Schematic timeline for subculture (indicated by *) of hESCs (day minus 1, "D⁻1") and NSCs (day 4, "D4") onto micropatterned substrates. Rosette formation was analyzed 5 days post-seeding onto micropatterned substrates. (B) Expression of Pax6 and Otx2 (a deterministic marker of forebrain identity) in neural tissues derived on 200 µm diameter circular micropatterned substrates displaying single neural rosettes 5 days post-seeding. (C) Percentages of micropatterned tissues comprising >1, 1, or zero neural rosettes, where the 200 µm diameter circular micropatterned tissues are derived from hESCs (subcultured/seeded on DJ) or NSCs (subcultured/seeded on D4). (D) Cell density within micropatterned tissues 5 days post-seeding depending on the subculture/seeding time point (D$^-$1 hESC vs. D4 NSC). * indicates p<0.05 according to a Student's t-test. (E) The average area of an ellipse fitted to the N-cadherin polarized ring with D$^-$1 hESC versus D4 NSC-derived micropatterned tissues in FIG. 1E. (F) A set of images showing single neural rosettes within tissues derived on 200 µm diameter circular micropatterns (top) as well as a transverse slice (bottom) of each tissue's highlighted (red) region.

FIG. 4 (D) Quantification of Nkx6.1$^+$ and Olig2$^+$ pMNs within micropatterned spinal tissues depicted in FIG. 4C using the varied conditions of FIG. 4B (n=8 tissues per condition). (A) A heatmap of qRT-PCR analysis of the micropatterned neuroepithelial tissue's rostrocaudal (R/C) regional patterning.

FIGS. 15A-15B are tables presenting the results of human image analysis versus algorithm-based analysis of (A) 300 μm circular neuroepithelial tissues and (B) neuroepithelial tissues having variable morphologies.

Figures 1A, 1B, 1C, 1D, 1E, 1F, 1G, 1H, 1I:
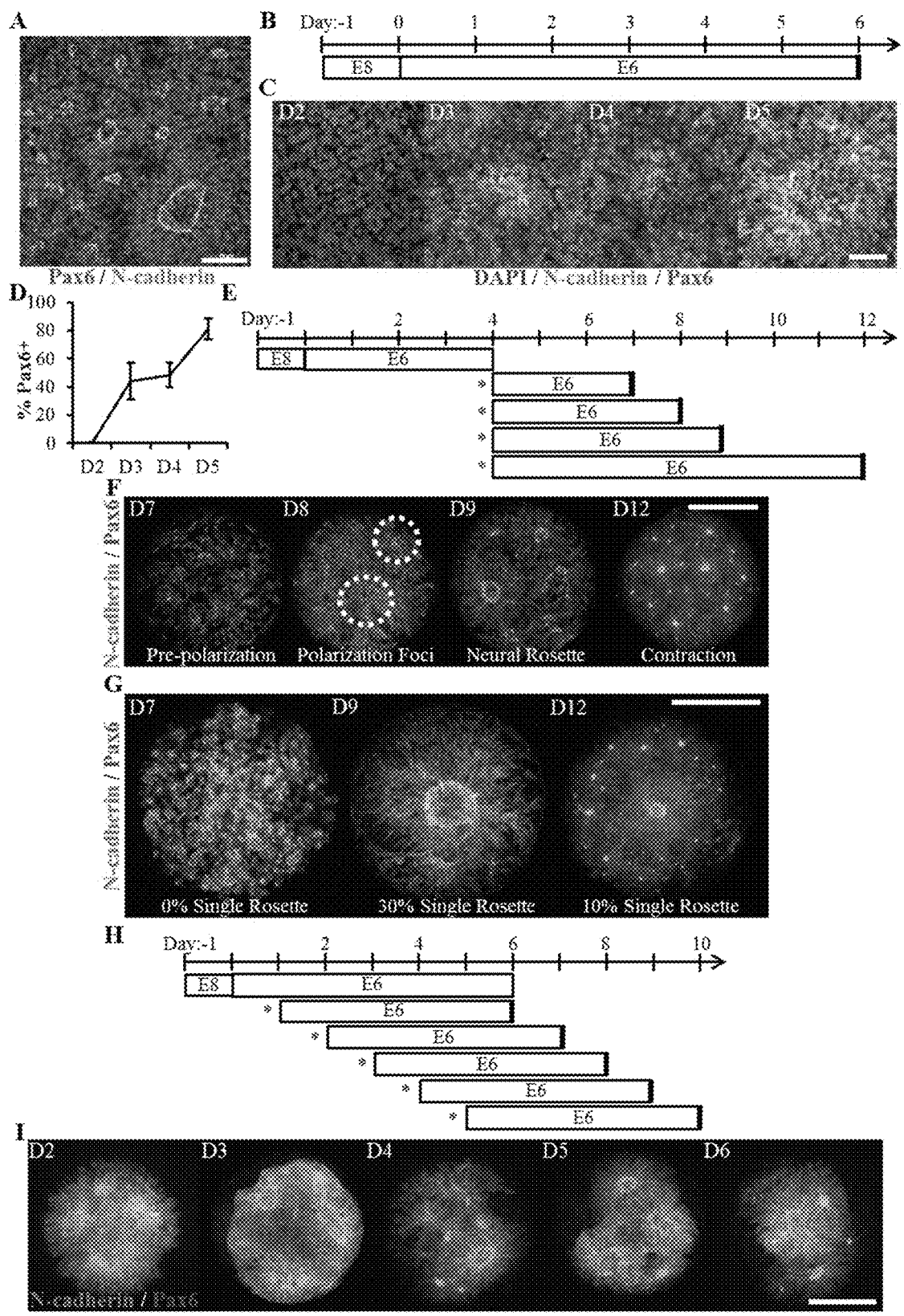
FIGS. 1A-1I. (A) Pax6 expression, a deterministic NSC marker, and N-cadherin polarization within NSC tissues derived from hESCs. Flower-like polarized structures are referred to neural rosettes. Scale bar is 50 μm. (B) Schematic timeline used in FIG. 1A to differentiate hESCs into NSCs in well plate culture using E6 media. (C) Pax6 expression and N-cadherin polarization over FIG. 1B's time course of hESCs differentiation into NSCs. Scale bar is 50 μm. (D) Flow cytometry quantification of Pax6 expression within neurally differentiating hESCs cultures on the indicated days (D) of FIG. 1B's timeline. (E) Schematic timeline for subculture (indicated by *) of day 4 (D4) NSCs onto micropatterned substrates and further cultured for various durations. (F) Polarization process of D4 NSC-derived tissues on single micropatterned regions at the indicated day corresponding to the FIG. 1E timeline. Scale bar is 200 μm. (G) Typical Pax6/N-cadherin staining of NSC tissues and the percentage (n=100) that contained singular neural rosette structure at the indicated day of FIG. 1E's timeline. Scale bar is 200 μm. (H) Schematic timeline for subculture (indicated by *) of neurally differentiating cultures onto micropatterned substrates at various derivation time points. (I) Polarized NSC tissues derived after 5 days of micropattern culture for each subculture time point indicated in FIG. 1H. Scale bar is 200 μm.

While the present invention is susceptible to various modifications and alternative forms, exemplary embodiments thereof are shown by way of example in the drawings and are herein described in detail. It should be understood, however, that the description of exemplary embodiments is not intended to limit the invention to the particular forms disclosed, but on the contrary, the intention is to cover all modifications, equivalents and alternatives falling within the spirit and scope of the invention as defined by the appended claims.

DETAILED DESCRIPTION

The present invention relates at least in part to the inventors' unexpected discovery of methods and an engineered culture system for in vitro generation of an engineered human neural tube—the embryonic predecessor of the brain and spinal cord—by directing differentiation of human cells under defined conditions. The present invention builds on the inventors' previous discovery that a defined set of cell culture conditions and components, e.g., xeno-free cell culture components, can be used to derive neuroepithelium/neural stem cells (NSCs) from hPSCs under chemically defined conditions and in the absence of TGFβ pathway antagonists or BMP pathway antagonists and without an embryoid body stage. As described herein, the inventors developed micropatterned substrates and cell culture parameters to reproducibly direct in vitro morphogenesis of neural stem cells and neurally differentiating hPSCs into neural tissues having microscale cellular organization (i.e., a singular neural rosette cytoarchitecture) mimetic of the developing neural tube, from which all central nervous system (CNS) tissues are derived in vivo. The micropatterned substrates and cell culture protocols allow for unprecedented control of neural tissue morphogenesis, which the current state-of-art methods lack. This discovery represents a significant advancement and universal basis for beginning to engineer anatomically biomimetic neural tissues and human CNS organoids in vitro. The inventors' discovery also provides an important opportunity to model patterning of the human CNS, to study neural development and disease in a biomimetic in vitro human model, and to identify materials and combinatorial strategies for in vitro tissue engineering.

I. Definitions

Unless defined otherwise, all technical and scientific terms used herein have the same meaning as commonly understood by one of ordinary skill in the art to which the invention pertains. Although any methods and materials similar to or equivalent to those described herein can be used in the practice or testing of the present invention, the preferred methods and materials are described herein.

In describing the embodiments and claiming the invention, the following terminology will be used in accordance with the definitions set out below.

As used herein, the term "pluripotent stem cell" (hPSC) means a cell capable of continued self-renewal and of capable, under appropriate conditions, of differentiating into cells of all three germ layers. hPSCs exhibit a gene expression profile that includes SOX2+ and OCT4+. Examples of human PSCs (hPSCs) include human embryonic stem cells (hESCs) and human induced pluripotent stem cells (hiPSCs). As used herein, "iPS cells" refer to cells that are substantially genetically identical to their respective differentiated somatic cell of origin and display characteristics similar to higher potency cells, such as ES cells, as described herein. The cells can be obtained by reprogramming non-pluripotent (e.g., multipotent or somatic) cells.

As used herein, "pluripotency" means a cell's ability to differentiate into cells of all three germ layers.

As used herein, "neural stem cell" (NSC) refers to a multipotent stem cell that is PAX6+/Sox2+ and is capable of differentiating into neurons or glia of the CNS or peripheral nervous system (PNS).

As used herein, the term "neuromesodermal progenitors" (NMPs) refers to human pluripotent stem cell-derived cells having the following gene expression profile: SOX2+/OCT4−/T+/PAX6−. NMPs are also referred to as caudal lateral epiblasts.

As used herein, the term "spinal motor neuron progenitors" (pMNs) refers to human pluripotent stem cell-derived cells positive for the expression of transcription factors including Olig2 and Nkx6.1. Olig2+ pMNs differentiate into spinal motor neurons (MNs) which are a highly specialized class of neurons that reside in the spinal cord and project axons in organized and discrete patterns to muscles to control their activity.

As used herein, the term "neural rosette" refers to a neural tube analog comprising polarized neural stem cells (NSCs) that forms when human pluripotent stem cells are differentiated in two-dimensional (2D) and three-dimensional (3D) culture.

A "biological molecule" or "biomolecule" as used in the context of this invention refers to a molecule that is substantially of biological origin. Such molecules may include non-naturally occurring components that mimic a naturally occurring component, e.g., a non-naturally occurring amino acid.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers, those containing modified residues, and non-naturally occurring amino acid polymer.

The term "chemically defined culture medium" or "chemically defined medium," as used herein, means that the chemical structure and quantity of each medium ingredient is definitively known.

As used herein, "a medium consisting essentially of" means a medium that contains the specified ingredients and those that do not materially affect its basic characteristics.

"Supplemented," as used herein, refers to a composition, e.g., a medium comprising a supplemented component (e.g., retinoic acid, FGF). For example a medium "further supplemented" with retinoic acid (RA) or an FGF, refers to the medium comprising RA or FGF, and not to the act of introducing the RA or FGF to the medium.

As used herein, "effective amount" means an amount of an agent sufficient to evoke a specified cellular effect according to the present invention.

As used herein, the terms "xenogen free" and "xeno-free" are used interchangeably and refer to a material that is free of or substantially free of xenogeneic material or undefined components that are derived from a non-human source.

"Neural differentiation base medium," as used herein, refers to a medium capable of promoting and supporting differentiation of human pluripotent stem cells towards a neural lineage, e.g., towards neuroectoderm and neuroepithelium. A neural differentiation base medium can include, but is not limited to E6 medium, as described herein and in U.S. Patent Publication No 2014/0134732.

The terms "purified" or "enriched" cell populations are used interchangeably herein, and refer to cell populations, ex vivo, that contain a higher proportion of a specified cell type or cells having a specified characteristic than are found en vivo (e.g., in a tissue).

As used herein, "serum-free" means that a medium does not contain serum or serum replacement, or that it contains essentially no serum or serum replacement. For example, an essentially serum-free medium can contain less than about 1%, 0.9%, 0.8%, 0.7%, 0.6%, 0.5%, 0.4%, 0.3%, 0.2% or 0.1% serum, wherein the culturing capacity of the medium is still observed.

As used herein, "substantially free of" means that a culture medium or other composition or solution is free or nearly free of a particular component. For example, "substantially free of putrescine" means no putrescine is added to a cell culture medium above and beyond any putrescine present in the base medium, e.g., DMEM/F12. Alternatively, "substantially free of putrescine" means a final putrescine concentration less than or equal to 0.08 mg/L.

As used herein, "viability" means the state of being viable. Pluripotent cells that are viable attach to the cell plate surface and do not stain with the dye propidium iodide absent membrane disruption. Short term viability relates to the first 24 hours after plating the cells in culture. Typically, the cells do not proliferate in that time.

As used herein, the term "about," when referring to a value or to an amount of mass, weight, time, volume, concentration, percentage or a physical dimension such as length, width, or diameter, is meant to encompass variations of in some embodiments ±20%, in some embodiments ±10%, in some embodiments ±5%, in some embodiments ±1%, in some embodiments ±0.5%, and in some embodiments ±0.1% from the specified value or amount, as such variations are appropriate to perform the disclosed methods.

II. Methods

The inventors discovered methods of using micropatterned substrates having particular features and particular cell culture parameters to control the differentiation of human pluripotent stem cells (hPSCs), neural stem cells (NSCs), or neuromesodermal progenitors (NMPs) to produce biomimetic neural rosette having advantageous properties. In particular, it was discovered that the size and shape of cell attachment-promoting regions of a micropatterned substrate influence the number of neural rosettes within a given cell culture. In some embodiments, micropatterned substrates are engineered (i.e., configured) to effectively and reliably derive biomimetic neural tissues comprising a particular number of rosette structures from neural morphogenesis of hPSCs, NMPs, or NSCs. As described herein and as demonstrated in the Examples that follow, the methods preferably yield a singular biomimetic neural tissue having a polarized rosette structure in which at least 80% of cells of the structure are Pax6+/N-cadherin+ neuroepithelial cells, wherein greater than about 75% of the biomimetic neural tissue exhibits a singular rosette structure comparable to a developing human neural tube.

Accordingly, in a first aspect, provided herein are in vitro methods for efficiently and robustly producing biomimetic neural tissue having a singular rosette structure in vitro, where the biomimetic neural tissue exhibits microscale cellular organization (i.e., cytoarchitecture) similar to that of the developing human neural tube. The term "biomimetic," as used in connection with a neural tissue containing a singular neural rosette structure produced on a cell culture substrate disclosed herein, refers to an aggregate of cells or a tissue having structural similarity to tissues found in nature, namely the anatomic structure and cytoarchitecture of the embryonic neural tube. Biomimetic neural tissues having a singular rosette structure are in vitro-derived (e.g., engineered) cell aggregates that mimic the polarized neural cytoarchitecture, with polarized NSCs displaying apical N-cadherin expression and basal extracellular matrix protein deposition, of an embryonic neural tube.

In certain embodiments, a method of producing a micropatterned biomimetic neural tissue having a singular rosette structure in vitro comprises or consists essentially of the following steps: (a) seeding human pluripotent stem cells (hPSCs) in the presence of a Rho kinase inhibitor onto a micropatterned substrate configured to instruct biomimetic neural morphogenesis of cells cultured thereon; (b) culturing the seeded cells of (a) on the micropatterned substrate for a first culture period of about one to two days in the presence of a first neural differentiation base medium to obtain a first cell population, wherein the first neural differentiation base medium comprises a Rho kinase inhibitor; and (c) culturing the cells of (b) for a second culture period of about 2 to about 6 days (e.g., 2, 3, 4, 5, 6 days, inclusive) under adherent culture conditions in a second neural differentiation base medium, whereby a singular biomimetic neural tissue having a polarized rosette structure in which at least 80% of cells of the structure are Pax6+/N-cadherin+ neuroepithelial cells is produced, wherein greater than about 75% of the biomimetic neural tissue exhibits a singular rosette structure comparable to a developing human neural tube.

The first neural differentiation medium can be a chemically defined medium comprising DMEM/F-12, ascorbic acid, sodium bicarbonate, selenium, insulin, transferrin, FGF2, and TGFβ1. The first neural differentiation medium can be E8 medium. The second neural differentiation medium can be a chemically defined medium comprising DMEM/F-12, ascorbic acid, sodium bicarbonate, selenium, insulin, transferrin. The second neural differentiation medium can be E6 medium. The second neural differentiation medium can further comprise one or more of an FGF and an activator of β-catenin pathway signaling. When the second culture period occurs in the presence of E6 medium, the resulting biomimetic neural tissue exhibits a singular rosette structure comprises cells having forebrain identity. Culturing the cells for about 2 to about 6 days in E6 media supplemented to further comprise an FGF and/or a Wnt/beta-catenin activator promotes the differentiation of cells having midbrain through spinal cord tissue identity within the resulting biomimetic neural tissue exhibits a singular rosette structure. The FGF can be FGF2, FGF8a, FGF8b, FGF8f, FGF17, or FGF18. The activator of β-catenin pathway signaling can be a GSK3 kinase inhibitor. The GSK3 kinase inhibitor can be CHIR99021. In some cases, the second neural differentiation medium comprises about 100 ng/ml to about 200 ng/ml FGF8b and about 3 μM to about 9 μM CHIR99021. The second culture period can be about 5 days. In some cases, the method further comprises transiently exposing cells on the micropatterned substrate to an activator of Wnt/β-catenin signaling about 24-72 hours after plating onto the micropatterned substrate. In some cases, the method further comprises, about 24-72 hours after seeding cells onto the micropatterned substrate, exposing the seeded cells to a retinoid RA and Sonic Hedgehog (SHH) or a SHH signaling agonist for about 1 to about 5 days, whereby the polarized rosette structure comprises Olig2+ motor neurons progenitors (pMNs). The SHH signaling agonist can be purmorphamine. The hPSCs can be seeded onto the micropatterned substrate at a density between about 75×10³ cells/cm² and about 2.5×10⁵ cells/cm².

In another aspect, provided herein is a method of producing a micropatterned biomimetic neural tissue having a singular rosette structure in vitro. The method can comprise culturing Oct4−/Sox2+/Brachyury−/Pax6+ neural stem cells (NSCs) on a micropatterned substrate configured to instruct biomimetic neural morphogenesis of cells cultured thereon for a culture period of about 3 to about 7 days (e.g., 3, 4, 5, 6, 7 days, inclusive) under adherent culture conditions in the presence of a neural differentiation base medium, wherein the neural differentiation medium is a chemically defined medium comprising DMEM/F-12, ascorbic acid, sodium bicarbonate, selenium, insulin, and transferrin and is supplemented to further comprise RA and a Rho kinase inhibitor; thereby producing a singular biomimetic neural tissue having a polarized rosette structure in which at least 80% of cells of the structure are Pax6+/N-cadherin+ neuroepithelial cells, wherein greater than about 75% of the biomimetic neural tissue exhibits a singular rosette structure comparable to a developing human neural tube. In certain embodiments, the NSCs are cultured on the micropatterned substrate for about 5 days. The NSCs can be seeded onto the micropatterned substrate at a density between about 75×10³ cells/cm² and about 2.5×10⁵ cells/cm².

In a further aspect, provided herein is a method of producing a micropatterned biomimetic neural tissue having a singular rosette structure in vitro, where the method comprises seeding Oct4−/Sox2+/Brachyury+/Pax6− neuromesodermal progenitors (NMPs) on a micropatterned substrate configured to instruct biomimetic neural morphogenesis of cells cultured thereon, and culturing the seeded NMPs for a culture period of about 2 to about 7 days (e.g., 2, 3, 4, 5, 6, 7 days, inclusive) under adherent culture conditions in the presence of a neural differentiation base medium, wherein the neural differentiation medium is supplemented with RA and a Rho kinase inhibitor; thereby producing a singular biomimetic neural tissue having a polarized rosette structure in which at least 80% of cells of the structure are Pax6+/N-cadherin+ neuroepithelial cells, wherein greater than about 75% of the biomimetic neural tissue exhibits a singular rosette structure comparable to a developing human neural tube. NMPs can be seeded onto the micropatterned substrate at a density between about 75×10³ cells/cm² and about 2.5×10⁵ cells/cm². In some embodiments, NMPs are cultured on the micropatterned substrate for about 5 days. In some cases, the method further comprises transiently exposing cells on the micropatterned substrate to an activator of Wnt/β-catenin signaling about 24-72 hours after plating onto the micropatterned substrate. In other cases, the method further comprises, about 24-72 hours after seeding cells onto the micropatterned substrate, exposing the seeded cells to an activator of the sonic hedgehog pathway for about 1 to about 5 days, whereby the polarized rosette structure comprises Olig2+ spinal motor neuron progenitors (pMNs). Suitable activators of the hedgehog pathway include, but are not limited to native or recombinant Sonic Hedgehog (SHH), purmorphamine (at a concentration from about 25 nM to about 2000 nM), smoothened agonist (SAG), or CUR61414. In certain embodiments, the SHH signaling agonist is purmorphamine at a concentration from about 25 nM to about 2000 nM.

The methods provided herein effectively (equal or greater than 80% efficiency) induce single neural rosette emergence within hPSC-derived forebrain and spinal tissues.

In some embodiments, the method employs a cell culture substrate comprising a micropatterned substrate configured to promote neural differentiation and controlled morphogenesis of hPSCs, NMPs, or NSCs cultured on the substrate into biomimetic neural tissues containing a singular rosette structure. Preferably, the micropatterned substrate comprises one or more regions resistant to cell attachment/adherence and one or more regions that promote cell attachment/adherence. For example, the methods of this disclosure can comprise culturing neural stem cells on one or more cell attachment-promoting regions of a micropatterned substrate, where the cell attachment-promoting regions are surrounded on some or all sides by regions that are resistant to cell attachment. In this manner, growth of the cultured neural stem cells is constrained and spread of cultured cells beyond the cell attachment-promoting regions is minimized or prevented. By the term "micropatterned" it is generally meant that a particular material (e.g., biomolecules, cell adhesion molecules) is arranged or ordered into a user-defined nano-to-microscale pattern.

In certain embodiments, the micropatterned substrate comprises an engineered, predetermined (i.e., user-defined) arrangement of one or more surface-grafted poly(ethylene glycol) ("PEG") brushes, which robustly resist protein adsorption and thereby cell adhesion. In such cases, a micropatterned substrate comprises a user-defined arrangement of one or more PEG brushes grafted onto a solid support (e.g., tissue culture polystyrene, glass slide, glass, or silica substrates). Micropatterned regions resistant to cell attachment can comprise a singular or a plurality of surface-grafted PEG brushes lacking any cell attachment peptides or other moieties that promote cell attachment. Micropatterned regions that promote adherence of cells cultured thereon can comprise a singular or a plurality of PEG brushes having a peptide-immobilizing moiety. In such cases, the arrangement of a singular or a plurality of peptide-immobilizing PEG brushes provides a user-defined, tunable substrate that can control cell adhesion and thereby the resulting tissue morphology. Furthermore, PEG brushes can be chemically modified to enable in situ conjugation of peptides, whose sequences are derived from extracellular matrix ("ECM") proteins. For example, a micropatterned substrate can comprise an arrangement of PEG brushes comprising peptides having one or more RGD (Arg-Gly-Asp) sequence motifs, which are also known as integrin binding motifs. A RGD sequence motif corresponds to a cell attachment site of a large number of adhesive ECM and cell surface proteins. RGD sequences are common in integrin-binding adhesion proteins such as fibronectin, collagen, and laminin. The integrin-binding activity of such adhesion proteins can be reproduced by short synthetic peptides containing the RGD sequence. Accordingly, to promote adherence of cells to particular regions of a micropatterned substrate, those regions can comprise one or more PEG brushes conjugated to RGD-containing peptides. For regions that are resistant to cell attachment, PEG brushes lacking any cell adhesion molecules (e.g., cell tethering moiety) are preferably used.

In some cases, a micropatterned substrate is obtained according to the synthesis protocols described by Knight et al., *Chem. Commun.*, 2015, 51, 5238-5241, which is incorporated by reference herein as if set forth in its entirety. As described therein, a micropatterned substrate can be an azide-functionalized poly(ethylene glycol) methacrylate (PEGMA) grafted substrate configured to undergo a 1,3-dipolar cycloaddition "click" reaction with peptides conjugated to high strain molecules such as dibenzocyclooctyne (DBCO). Other peptide immobilizing PEG brushes are described by Sha et al., *Biomacromolecules*, 2013, 14 (9): 3294-3303, which is incorporated by reference herein as if set forth in its entirety. As described therein, PEG brushes present dual orthogonal chemistries (i.e., azido and acetylene groups) for ligand (e.g., peptide) immobilization via versatile copper-free click reactions, which are useful for in situ surface modifications during cell culture and thereby spatiotemporal control of adherent tissue morphologies.

In some cases, a micropatterned substrate comprises one or more PEG brushes or poly(ethylene glycol) methacrylate (PEGMA)-azide brushes everywhere except for an array of circles having a diameter of about 100 μm, 200 μm, 250 μm, 300 μm, or more. In such cases, when seeded with hPSCs, NMPs, or NSCs, the cells will adhere within the circular brush-free regions. When further cultured, the cells differentiate into shaped tissues confined by the surrounding inert PEG or PEGMA-azide brushes. Advantageously, the micropatterned substrates provided herein can comprise a plurality of cell adhesion peptides arranged according to user-defined, tunable spatial parameters. User-defined parameters include spacing, diameter (also sometimes referred to herein as "width"), height (also sometimes referred to herein as "length"), and number of cell adhesion peptides per unit of surface area (also referred to herein as "cell adhesion peptide surface area density").

Accordingly, provided herein are micropatterned substrates comprising regions that promote adherence of cells cultured thereon, where these regions are engineered (i.e., configured) to have a bounded geometry to promote differentiation and morphogenesis of neural stem cells or human pluripotent stem cells cultured on or recruited to the matrix. For example, bounded geometries of a micropatterned substrate may be used to control the macroscale structuring of neural tissue during cell differentiation and morphogenesis of hPSCs or NMPs on the culture substrate. The bounded geometric shape can be any two-dimensional (2-D) shape (e.g., regular or irregular) having dimensions defined by the shape (e.g., pre-defined diameter, length, width etc.) (e.g., diameter, width, length and the like). In some embodiments, the bounded geometric shapes are circle, triangles, squares, rectangles, or ovals of varying dimensions (e.g., 36 μm, 100 μm, 490 μm, 4.8 mm, and 12.6 mm in diameter; typically about 200-800 μm). The dimensions will have a defined scale based upon their shape such that at least one distance from one side to a substantially opposite side is about 100-800 μm (e.g., where the shape is rectangular or oval, the distance between one side to an opposite side is 100-800 μm). In preferred embodiments, the bounded geometric shape of a micropatterned substrate is a circle measuring about 100 μm, 150 μm, 180 μm, 200 μm, about 300 μm, or about 400 μm in diameter. In some cases, it may be appropriate to use a circle or other shape having a diameter of less than 100 μm and, in some cases, as low as 50 μm (e.g., 50, 60, 70, 80, 90, or 100 μm), however proliferating cells grown on smaller micropatterned surfaces tend to lift off the surface as an aggregate or ball of cells. Accordingly, practical constraints may set a lower limit on micropatterned surface dimensions. In other embodiments, the geometric shape may comprise a 3-D shape (e.g., a spheroid, cube, pyramid). In such instances, the diameter/width and the like, will be from about 100 μm to 800 μm.

Any appropriate means of producing a micropatterned substrate can be used. In some cases, micropatterned substrates are produced by manually depositing peptide-immobilizing PEG brushes and cell adhesion peptides onto a solid support. In other cases, micropatterned substrates are produced using automated (e.g., robotic) techniques, microcontact printing, microfluidic etching, or deposition of various materials. In other cases, photolithography-based microfabrication techniques can be used. For example, photolithography-based microfabrication techniques can be used to produce templates or molds for micrometer-level patterning of a cell adhesion-resistant substance (e.g., a nonadherent agar) onto a substrate (e.g., glass slide, glass coverslip, elastomeric polymer (e.g., polydimethylsiloxane (PDMS)) coated with a cell adhesive material. In this manner, the methods yield a micropatterned substrate comprising well-defined adhesive and nonadhesive domains.

In a first step, a method for efficiently and robustly producing neural rosettes having microscale cellular organization (i.e., cytoarchitecture) similar to that of the developing human neural tube comprises culturing neural stem cells (NSCs) on a micropatterned substrate as described herein, where the micropatterned substrate preferably has a user-defined bounded geometry that promotes differentiation of neural stem cells or human pluripotent stem cells cultured thereon to produce a biomimetic neural rosette. The NSCs can be seeded onto the micropatterned substrate at a particular cell density and at a particular stage of differentiation from hPSCs. For example, neural stem cells (NSCs) or neuromesodermal progenitors (NMPs) can be seeded onto a micropatterned substrate having a user-defined bounded geometry at a density of about 50,000 cells/cm$^2$ to about 250,000 cells/cm$^2$ (e.g., about 50,000 cells/cm$^2$, about 60,000 cells/cm$^2$, about 70,000 cells/cm$^2$, about 75,000 cells/cm$^2$, about 80,000 cells/cm$^2$, about 90,000 cells/cm$^2$, about 95,000 cells/cm$^2$, about 100,000 cells/cm$^2$, about 150,000 cells/cm$^2$, about 200,000 cells/cm$^2$, about 250,000 cells/cm$^2$). In certain embodiments, NSCs are seeded onto a micropatterned substrate on day 4 of the in vitro differentiation protocol described in U.S. patent application Ser. No. 13/795,485 (published as U.S. Patent Pub. 2014/0134732), which is incorporated by reference herein as if set forth in its entirety. The '485 application provides a chemically defined, feeder-independent, and xenogeneic material-free protocol for directly differentiating hPSCs into pure neuroepithelial cultures (>90% Pax6$^+$/N-cadherin$^+$ neural stem cells having widespread rosette formation) within 6 days under adherent conditions, without small molecule inhibitors, and using only minimalistic medium consisting of DMEM/F12, sodium bicarbonate, selenium, ascorbic acid, transferrin, and insulin (i.e., E6 medium). Preferably, NSCs are seeded onto a micropatterned substrate having a user-defined bounded geometry at a density between about $75\times10^3$ cells/cm$^2$ and about $2.5\times10^5$ cells/cm$^2$ on day 4 of the E6 in vitro differentiation described in the '485 application.

In some cases, pluripotent stem cells that have been cultured in an adherent monolayer in a cell culture plate are subcultured onto a micropatterned surface and then cultured for a first culture period of about three (3) days to about six (6) days in a defined culture medium that supports differentiation of human pluripotent stem cells into neural stem cells, whereby PAX6-positive neural stem cells are obtained.

In some cases, the methods further comprise releasing geometric confinement to the bounded micropatterned surfaces. As described in the Examples that follow, release of geometric confinement is associated with radial outgrowth from the neural rosette tissues and with maintenance of a singular neuroepithelium and peripheral neuronal differentiation. In some cases, array substrates are configured to permit controllable release of micropatterned tissues from their geometric confinement ("bounded geography") and permit radial tissue outgrowth. In some cases, the micropatterned substrates is configured to comprise "clickable" bioconjugates in which a peptide such as heparin binding peptide that does not itself promote cell migration but can bind to polypeptide secreted by cells of the neural rosette tissue during extended culture.

In some cases, the differentiation method provided herein further includes exposing cultured cells (e.g., cultured NMPs) to a transient increase or "boost" of Wnt/β-catenin signaling by transiently exposing the cultured seeded NMPs cells to a Wnt/β-catenin signaling agonist following about 72 hours of culture, for example, as described in U.S. application Ser. No. 14/496,796, which is incorporated by reference as if set forth in its entirety. In some cases, cultured seeded NMPs cells are exposed to a Wnt/β-catenin signaling "boost" following about 72 hours of culture (i.e., about 72 hours following seeding onto a micropatterned substrate). As will be appreciated by those of ordinary skill in the art, Wnt/β-catenin signaling can be activated by modulating the function of one or more proteins that participate in the Wnt/β-catenin signaling pathway to increase β-catenin expression levels or activity, TCF and LEF expression levels, or β-catenin/TCF/LEF induced transcriptional activity. In some embodiments, activation of Wnt/β-catenin signaling is achieved by inhibiting Gsk3 phosphotransferase activity or Gsk3 binding interactions. While not wishing to be bound by theory, it is believed that inhibition of Gsk3 phosphorylation of β-catenin will inhibit tonic degradation of β-catenin and thereby increase the level of β-catenin and activity to drive differentiation of pluripotent stem cells. Gsk3 inhibition can be achieved in a variety of ways including, but not limited to, providing small molecules that inhibit Gsk3 phosphotransferase activity, RNA interference knockdown of Gsk3, and overexpression of dominant negative form of Gsk3. Dominant negative forms of Gsk3 are known in the art as described, e.g., in Hagen et al. (2002), 1 *Biol. Chem.*, 277(26):23330-23335, which describes a Gsk3 comprising a R96A mutation.

In some embodiments, Gsk3 is inhibited by contacting a cell with a small molecule that inhibits Gsk3 phosphotransferase activity or Gsk3 binding interactions. Suitable small molecule Gsk3 inhibitors include, but are not limited to, CHIR99021, CHIR98014, BIO-acetoxime, BIO, LiCl, SB 216763, SB 415286, AR A014418, 1-Azakenpaullone, Bis-7-indolylmaleimide, and any combinations thereof. In some embodiments, any of CHIR99021, CHIR98014, and BIO-acetoxime are used to inhibit Gsk3 in pluripotent stem cells in the differentiation methods described herein. In one embodiment, the small molecule Gsk3 inhibitor to be used is CHIR99021 at a concentration ranging from about 3 μM to about 12 μM, e.g., about 3 μM, 4 μM, 5 μM, 6 μM, 7 μM, 8 μM, 9 μM, 10 μM, 11 μM, 12 μM or another concentration of CHIR99021 from about 3 μM to about 12 μM. In another embodiment, the small molecule Gsk3 inhibitor to be used is CHIR98014 at a concentration ranging from about 0.1 μM to about 1 μM, e.g., about 0.1 μM, 0.2 μM, 0.3 μM, 0.4 μM, 0.5 μM, 0.6 μM, 0.7 μM, 0.8 μM, 0.9 μM or another concentration of CHIR98014 from about 0.1 μM to about 1 μM. In another embodiment, the small molecule Gsk3 inhibitor to be used is BIO-acetoxime at a concentration ranging from about 0.1 μM to about 1 μM, e.g., about 0.1 μM, 0.2 μM, 0.3 μM, 0.4 μM, 0.5 μM, 0.6 μM, 0.7 μM, 0.8 μM, 0.9 μM or another concentration of BIO-acetoxime from about 0.1 μM to about 1 μM.

In other embodiments, Gsk3 activity is inhibited by RNA interference knockdown of Gsk3. For example, Gsk3 expression levels can be knocked-down using commercially available siRNAs against Gsk3, e.g., SignalSilence® GSK-3α/β siRNA (catalog #6301 from Cell Signaling Technology®, Danvers, Mass.), or a retroviral vector with an inducible expression cassette for Gsk3, e.g., a commercially available Tet-inducible retroviral RNA interference (RNAi) system from Clontech (Mountain View, Calif., Catalog No. 630926), or a cumate-inducible system from Systems Biosciences, Inc. (Mountain View, Calif.), e.g., the SparQ® system, catalog no. QM200PA-2.

In other embodiments, the Wnt/β-catenin signaling pathway is activated by overexpressing β-catenin itself, e.g., human β-catenin (exemplary nucleotide and amino acid sequences are found at GenBank Accession Nos: X87838 and CAA61107.1, respectively). In one embodiment, β-catenin overexpression is achieved using an inducible expression system, e.g., any of the just-mentioned inducible expression systems. Alternatively, a constitutively active, stabilized isoform of β-catenin is used, which contains point mutations S33A, S37A, T41A, and S45A as described, e.g., in Baba et al. (2005), *Immunity* 23(6):599-609.

In yet other embodiments, Wnt/β-catenin signaling pathway activation in pluripotent stem cells is achieved by contacting the cells with an agent that disrupts the interaction of β-catenin with Axin, a member of the β-catenin destruction complex. Disruption of the Axin/β-catenin interaction allows β-catenin to escape degradation by the destruction complex thereby increasing the net level of β-catenin to drive β-catenin signaling. For example, the Axin/β-catenin interaction can be disrupted in pluripotent cells by contacting the cells with the compound 5-(Furan-2-yl)-N-(3-(1H-imidazol-1-yl)propyl)-1,2-oxazole-3-carboxamide ("SKL2001"), which is commercially available, e.g., as catalog no. 681667 from EMD Millipore. An effective concentration of SKL2001 to activate Wnt/β-catenin signaling ranges from about 10 μM to about 100 μM, about 20 µM, 30 µM, 40 µM, 50 µM, 60 µM, 70 µM, 80 µM, 90 µM or another concentration of SKL2001 from about 10 µM to about 100 µM.

In some cases, neural stem cells for use in the methods provided herein are obtained by directed differentiation of human pluripotent stem cells (hPSCs). As used herein, "pluripotent stem cells" appropriate for use according to a method of the invention are cells having the capacity to differentiate into cells of all three germ layers. Suitable pluripotent cells for use herein include human embryonic stem cells (hESCs) and human induced pluripotent stem (iPS) cells. As used herein, "embryonic stem cells" or "ESCs" mean a pluripotent cell or population of pluripotent cells derived from an inner cell mass of a blastocyst. See Thomson et al., *Science* 282:1145-1147 (1998). These cells express Oct-4, SSEA-3, SSEA-4, TRA-1-60 and TRA-1-81, and appear as compact colonies having a high nucleus to cytoplasm ratio and prominent nucleolus. ESCs are commercially available from sources such as WiCell Research Institute (Madison, Wis.). As used herein, "induced pluripotent stem cells" or "iPS cells" mean a pluripotent cell or population of pluripotent cells that may vary with respect to their differentiated somatic cell of origin, that may vary with respect to a specific set of potency-determining factors and that may vary with respect to culture conditions used to isolate them, but nonetheless are substantially genetically identical to their respective differentiated somatic cell of origin and display characteristics similar to higher potency cells, such as ESCs, as described herein. See, e.g., Yu et al., *Science* 318:1917-1920 (2007).

Induced pluripotent stem cells exhibit morphological properties (e.g., round shape, large nucleoli and scant cytoplasm) and growth properties (e.g., doubling time of about seventeen to eighteen hours) akin to ESCs. In addition, iPS cells express pluripotent cell-specific markers (e.g., Oct-4, SSEA-3, SSEA-4, Tra-1-60 or Tra-1-81, but not SSEA-1). Induced pluripotent stem cells, however, are not immediately derived from embryos. As used herein, "not immediately derived from embryos" means that the starting cell type for producing iPS cells is a non-pluripotent cell, such as a multipotent cell or terminally differentiated cell, such as somatic cells obtained from a post-natal individual.

Human iPS cells can be used according to a method described herein to obtain primitive macrophages and microglial cells having the genetic complement of a particular human subject. For example, it may be advantageous to obtain neural tissue organoids that exhibit one or more specific phenotypes associated with or resulting from a particular disease or disorder of the particular mammalian subject. In such cases, iPS cells are obtained by reprogramming a somatic cell of a particular human subject according to methods known in the art. See, for example, Yu et al., *Science* 324(5928):797-801 (2009); Chen et al., *Nat. Methods* 8(5):424-9 (2011); Ebert et al., *Nature* 457(7227):277-80 (2009); Howden et al., *Proc. Natl. Acad. Sci. U.S.A.* 108(16):6537-42 (2011).

Prior to plating onto a micropatterned substrate, hPSCs (e.g., hESCs or hiPSCs), can be cultured in the absence of a feeder layer (e.g., a fibroblast layer) on a substrate suitable for proliferation of hPSCs, e.g., MATRIGEL™, vitronectin, a vitronectin fragment, or a vitronectin peptide, or Synthemax®. In some cases, the hPSCs are passaged at least 1 time to at least about 5 times in the absence of a feeder layer. Suitable culture media for passaging and maintenance of hPSCs include, but are not limited to, mTeSR® and E8™ media. In some embodiments, the hPSCs are maintained and passaged under xeno-free conditions, where the cell culture medium is a defined medium such as E8 or mTeSR, but the cells are maintained on a completely defined, xeno-free substrate such as vitronectin or Synthemax® (or another type-of self-coating substrate). In one embodiment, the hPSCs are maintained and passaged in E8 medium on vitronectin, a vitronectin fragment, or a vitronectin peptide or a self-coating substrate such as Synthemax®.

In preparation for differentiation into neural stem cells, hPSCs are typically plated onto a micropatterned substrate at a density of at least about $50 \times 10^3$ cells/cm$^2$ to about $2 \times 10^5$ cells/cm$^2$ (e.g., at least about $50 \times 10^3$ cells/cm$^2$, $75 \times 10^3$ cells/cm$^2$, $1 \times 10^5$ cells/cm$^2$, $1.5 \times 10^5$ cells/cm$^2$, $2 \times 10^5$ cells/cm$^2$, $2.5 \times 10^5$ cells/cm$^2$. While not wishing to be bound by theory, it is believed that the density of hPSCs is an important factor affecting the efficiency of the methods described herein. In some embodiments, plated hPSCs will be at least about 95% confluent upon changing the culture medium from one suited for hPSC proliferation to one that sustains differentiation of the hPSCs as described herein.

In various embodiments, the differentiation of hPSCs into neural stem cells is affected by culturing the pluripotent stem cells (PSCs) in any of a number of serum-free media that support differentiation of human pluripotent stem cells into neural stem cells, collectively referred to herein as ("neural differentiation media"). "Neural differentiation medium," as used herein, refers to a medium capable of promoting and supporting differentiation of human pluripotent stem cells towards a neural lineage, e.g., towards neuroectoderm and neuroepithelium. A neural differentiation base medium can include, but is not limited to E6 medium, as described herein and in U.S. Patent Publication No. 2014/0134732. In some embodiments, the neural differentiation medium to be used in the neural differentiation method is "E4" medium, which consists essentially of a base medium (e.g., DMEM/F12 or a similar base medium as described herein) containing water, salts, amino acids, vitamins, a carbon source, a buffering agent; plus selenium and insulin. Optionally, the neural differentiation medium to be used may also include ascorbate (referred to herein as an "E5" medium). In some embodiments, the neural differentiation medium to be used in the neural differentiation method is "E6" medium, which consists essentially of a carbonate-buffered E5 medium plus transferrin.

As used herein, the terms "E6 culture medium" and "E6" are used interchangeably and refer to a chemically defined culture medium comprising or consisting essentially of DF3S supplemented to further comprise insulin (20 µg/mL), transferrin (10.67 ng/mL). The medium can be prepared based on the formula in previous publication (Chen et al., (2011) *Nature Methods*. 8(4), 424-429). Similar medium is available from Thermal Fisher/Life Technologies Inc. as Essential 6, or from Stem Cell Technologies as TeSR-E6. As used herein, the terms "E8 culture medium" and "E8" are used interchangeably and refer to a chemically defined culture medium comprising or consisting essentially of DF3S supplemented by the addition of insulin (20 µg/mL), transferrin (10.67 ng/mL), human FGF2 (100 ng/mL), and human TGFβ1 (Transforming Growth Factor Beta 1) (1.75 ng/mL). The medium can be prepared based on the formula in previous publication (Chen et al., (2011) *Nature Methods*. 8(4), 424-429). As an alternative, the medium is also available from Thermal Fisher/Life Technologies Inc. as Essential 8, or from Stem Cell Technologies as TeSR-E8.

In other embodiments, the medium to be used includes at least the same components as a neural differentiation medium mentioned above, but the medium is substantially free of: a TGFβ superfamily agonist (e.g., Nodal); an albumin, and at least one of putrescine and progesterone. Optionally, a fibroblast growth factor (e.g., FGF2) may also be included in the medium to be used. In other embodiments, the medium to be used does not include a fibroblast growth factor. In some embodiments, a retinoic acid receptor agonist is also included to facilitate neural differentiation into certain neuronal lineages depending on the concentration of retinoid used. An exemplary class of suitable retinoic acid receptor agonists are the retinoids and retinoid analogs, which include without limitation All-Trans Retinoic Acid (ATRA), Retinol Acetate, EC23 (4-[2-(5,6,7,8-Tetrahydro-5,5,8,8-te-tramethyl-2-naphthalenyl)ethynyl)-benzoic acid; CAS No: 104561-41-3), BMS453 (4-[(1E)-2-(5,6-Dihydro-5,5-dimethyl-8-phenyl-2-naphthalenyl)ethenyl]-benzoic acid; CAS No: 166977-43-10), Fenretinide (N-(4-Hydroxyphenyl)retinamide; CAS No: 65646-68-6), AM580 (4-[(5,6,7,8-Tetrahydro-5,5,8,8-tetramethyl-2-naphthalenyl)carboxamido]benzoic acid; CAS No: 102121-60-8), Tazarotene (6-[2-(3,4-Dihydro-4,4-dimethyl-2H-1-benzothiopyran-6-yl)ethynyl]-3-pyridinecarboxylic acid ethyl ester; CAS No: 118292-40-3), and TTNPB (4-[(E)-2-(5,6,7,8-Tetrahydro-5,5,8,8-tetramethyl-2-naphthalenyl)-1-propenyl]benzoic acid; CAS No: 71441-28-6). Other exemplary retinoic acid receptor agonists that could be used include AC261066 (4-[4-(2-Butoxyethoxy-)-5-methyl-2-thiazolyl]-2-fluorobenzoic acid; CAS No: 870773-76-5), AC55649 (4'-Octyl-[1,1'-biphenyl]-4-carboxylic acid; CAS No: 59662-49-6), Adapalene (6-(4-Methoxy-3-tricyclo[3.3.1.13,7]dec-1-ylphenyl)-2-naphthalenecarboxylic acid; CAS No: 106685-40-9), AM80 (4-[[(5,6,7,8-Tetrahydro-5,5,8,8-tetramethyl-2-naphthalenyl)amino]carbonyl]benzoic acid; CAS No: 94497-51-5), BMS753 (4-[[(2,3-Dihydro-1,1,3,3-tetramethyl-2-oxo-1H-inden-5-yl)carbonyl]amino]benzoic acid; CAS No: 215307-86-1), BMS961 (3-Fluoro-4-[[2-hydroxy-2-(5,5,8,8-tetramethyl-5,6,7,8,-tetrahydro-2-naphthalenyl) acetyl]amino]-benzoic acid; CAS No: 185629-22-5), CD1530 (4-(6-Hydroxy-7-tricyclo[3.3.1.13,7]dec-1-yl-2-naphthalenyl)benzoic acid; CAS No: 107430-66-0), CD2314 (5-(5,6,7,8-Tetrahydro-5,5,8,8-tetramethyl-2-anthracenyl)-3-thiophenecarboxylic acid; CAS No: 170355-37-0), CD437 (6-(4-Hydroxy-3-tricyclo[3.3.1.13,7]dec-1-ylphenyl)-2-naphthalenecarboxylic acid; CAS No: 125316-60-1), and Ch55 (4-[(1E)-3-[3,5-bis(1,1-Dimethylethyl) phenyl]-3-oxo-1-propenyl]benzoic acid; CAS No: 110368-33-7). In some embodiments, the concentration of the retinoic acid receptor agonist (e.g., all-trans retinoic acid (ATRA) is about 0.1 µM to about 1.0 µM. A suitable concentration of retinoic acid receptor agonist ranges from about 0.1 µM to about 20 µM, e.g., about 0.2 µM, 0.3 µM, 0.5 µM, 1.0 µM, 2.5 µM, 3.0 µM, 3.5 µM, 4.0 µM, 5 µM, 7 µM, 10 µM, 12 µM, 15 µM, 17 µM or another concentration of ATRA from about 0.1 µM, to about 20 µM. In some embodiments, the concentration of ATRA is about 3.0 µM.

Directed differentiation of human pluripotent stem cells into neural stem cells is carried out by culturing pluripotent stem cells on a substrate that supports proliferation of pluripotent stem cells (e.g., vitronectin or MATRIGEL™), and in a serum-free medium comprising water, salts, amino acids, vitamins, a carbon source, a buffering agent, selenium and insulin, wherein human pluripotent stem cells are cultured in the substantial absence of embryoid bodies, a transforming growth factor β (TGFβ) superfamily agonist, a TGFβ signaling antagonist, or a bone morphogenetic protein (BMP) signaling antagonist. In other embodiments, cells are cultured in a medium described herein and further supplemented to include, for example, a TGFβ signaling antagonist (e.g., SB431542, Sigma; at about 10 µM) and/or a BMP signaling antagonist (e.g., noggin at about 200 ng/ml or dorsomorphin at about 1 µM).

In some embodiments, the hPSCs are cultured in the presence of one of the neural differentiation media described herein to obtain a population of cells that is at least about 90% PAX6-positive (by protein expression) within a period of at least about four days to about 12 days, e.g., about 5 days, 6 days, 7 days, 8 days, 9 days, 10 days, 11 days, or another period from at least about 4 days to about 12 days. In some embodiments, the cultured cells are at least 90% PAX6-positive at any period from about four days to about six days after initiating neural differentiation of the hPSCs.

The expression (or lack thereof) of a number of cell type-associated markers can be used to characterize the differentiation of hPSCs or NMPs into neural stem cells over the course of the methods described herein. For example, the expression of some markers associated with pluripotency in hPSCs decline over the course of differentiation of the hPSCs into neural stem cells. Such pluripotency markers include Oct4, Nanog, SSEA-3, SSEA-4, TRA-1-60, and TRA-1-81. Neuromesodermal progenitors (NMPs) have the following expression profile: $SOX2^+/OCT4^-/T/PAX6^-$. During differentiation of NMPs to neural stem cells or neuronal cell types, expression of these NMP markers and other markers associated with mesoderm or endoderm also decline over time or are absent, e.g., T (Brachyury) and Sox 17. Conversely the expression of markers associated with neural stem cells increases over the course of differentiation. Suitable markers (at the RNA or protein level) for neural stem cells and neural differentiation include, but are not limited to, PAX6, SOX2, Nestin, N-Cadherin, and SOX1.

Typically, the populations of neural stem cells obtained by the methods described herein comprise at least 90% PAX6-positive neural stem cells. Such populations may then be patterned and adopt the identity of progenitors of various cell types within the CNS. For example, the neural stem cells can be differentiated into motor neurons, forebrain cortical glutamatergic neurons, GABAergic neurons, cholinergic neurons, and astrocytes. Alternatively, the neural stem cells may be passaged and expanded in the presence of FGF and/or frozen in a freezing medium (e.g., Synth-A-Freeze® medium) at high density (e.g., about $1 \times 10^6$ cells/ml).

Any appropriate method can be used to detect expression of biological markers characteristic of cell types described herein. For example, the presence or absence of one or more biological markers can be detected using, for example, RNA sequencing, immunohistochemistry, polymerase chain reaction, qRT-PCR, or other technique that detects or measures gene expression. Suitable methods for evaluating the above-markers are well known in the art and include, e.g., qRT-PCR, RNA-sequencing, and the like for evaluating gene expression at the RNA level. Quantitative methods for evaluating expression of markers at the protein level in cell populations are also known in the art. For example, flow cytometry is typically used to determine the fraction of cells in a given cell population that express (or do not express) a protein marker of interest (e.g., PAX6). As described in the Examples section below, differentiation of human pluripotent stem cells into biomimetic neural rosettes according to methods of the present invention can be confirmed based on the absence of non-neural cell types such as and the presence of cells having neural identity. Differentiated cell identity is also associated with downregulation of pluripotency markers such as NANOG and OCT4 (relative to human ES cells or induced pluripotent stem cells).

Induced pluripotent stem cell-derived biomimetic neural tissues comprising one or more rosette structures allow modeling of drug responses in tissue constructs that recapitulate neural development in an individual having, for example, a particular genetic background or detectable phenotype. Accordingly, subject-specific human iPS cell-derived biomimetic neural tissues comprising one or more rosette structures are useful to identify genetic factors and epigenetic influences that contribute to variable effects of a known or unknown drug on neural development/neural differentiation.

Subject-specific somatic cells for reprogramming into induced pluripotent stem cells can be obtained or isolated from a target tissue of interest by biopsy or other tissue sampling methods. In some cases, subject-specific cells are manipulated in vitro prior to use in a three-dimensional tissue construct of the invention. For example, subject-specific cells can be expanded, differentiated, genetically modified, contacted to polypeptides, nucleic acids, or other factors, cryo-preserved, or otherwise modified prior to introduction to a micropatterned substrate to obtain biomimetic neural tissues comprising one or more rosette structures.

Preferably, human pluripotent stem cells (e.g., human ESCs or iPS cells) are cultured in the absence of a feeder layer (e.g., a fibroblast layer), a conditioned medium, or a culture medium comprising poorly defined or undefined components. As used herein, the terms "chemically defined medium" and "chemically defined cultured medium" also refer to a culture medium containing formulations of fully disclosed or identifiable ingredients, the precise quantities of which are known or identifiable and can be controlled individually. As such, a culture medium is not chemically defined if (1) the chemical and structural identity of all medium ingredients is not known, (2) the medium contains unknown quantities of any ingredients, or (3) both. Standardizing culture conditions by using a chemically defined culture medium minimizes the potential for lot-to-lot or batch-to-batch variations in materials to which the cells are exposed during cell culture. Accordingly, the effects of various differentiation factors are more predictable when added to cells and tissues cultured under chemically defined conditions. As used herein, the term "serum-free" refers to cell culture materials that are free of or substantially free of serum obtained from animal (e.g., fetal bovine) blood. In general, culturing cells or tissues in the absence of animal-derived materials (i.e., under conditions free of xenogeneic material) reduces or eliminates the potential for cross-species viral or prion transmission.

To increase plating efficiency and cell viability, cells are preferably plated onto a micropatterned substrate in one of the above-mentioned media in the presence of a Rho-Kinase (ROCK) inhibitor, e.g., Y-27632 (R&D Systems) at a concentration of about 10 μM and cultured overnight prior to initiating neural differentiation. Kinase inhibitors, such as ROCK inhibitors, are known to protect single cells and small aggregates of cells. See, e.g., US Patent Application Publication No. 2008/0171385, incorporated herein by reference as if set forth in its entirety; and Watanabe K, et al., "A ROCK inhibitor permits survival of dissociated human embryonic stem cells," Nat. Biotechnol. 25:681-686 (2007). ROCK inhibitors are shown below to significantly increase pluripotent cell survival on chemically defined surfaces. ROCK inhibitors suitable for use herein include, but are not limited to, (S)-(+)-2-methyl-1-[(4-methyl-5-isoquinolinyl)sulfonyl]homopiperazine dihydrochloride (informal name: H-1152), 1-(5-isoquinolinesulfonyl)piperazine hydrochloride (informal name: HA-100), 1-(5-isoquinolinesulfonyl)-2-methylpiperazine (informal name: H-7), 1-(5-isoquinolinesulfonyl)-3-methylpiperazine (informal name: iso H-7), N-2-(methylamino) ethyl-5-isoquinoline-sulfonamide dihydrochloride (informal name: H-8), N-(2-aminoethyl)-5-isoquinolinesulphonamide dihydrochloride (informal name: H-9), N-[2-p-bromo-cinnamylamino)ethyl]-5-isoquinolinesulfonamide dihydrochloride (informal name: H-89), N-(2-guanidinoethyl)-5-isoquinolinesulfonamide hydrochloride (informal name: HA-1004), 1-(5-isoquinolinesulfonyl)homopiperazine dihydrochloride (informal name: HA-1077), (S)-(+)-2-Methyl-4-glycyl-1-(4-methylisoquinolinyl-5-sulfonyl)homopiperazine dihydrochloride (informal name: glycyl H-1152) and (+)-(R)-trans-4-(1-aminoethyl)-N-(4-pyridyl)cyclohexanecarboxamide dihydrochloride (informal name: Y-27632). The kinase inhibitor can be provided at a concentration sufficiently high that the cells survive and remain attached to the surface. An inhibitor concentration between about 3 μM to about 10 μM can be suitable. At lower concentrations, or when no ROCK inhibitor is provided, undifferentiated cells typically detach, while differentiated cells remain attached to the defined surface.

In a further aspect, provided herein is a method of generating a series of biomimetic neural tissues, each comprising a singular rosette structure, where the series of engineered biomimetic neural tissues comprise neurons and neuron-supporting cells found at particular stages of development of the human neural tube. In some cases, the method comprises culturing a cell culture substrate comprising biomimetic neural tissues having a singular rosette structure under conditions that promote further differentiation of cells of the neural rosettes into various cell types of the human central nervous system. For example, the neural rosettes can be cultured under conditions that promote differentiation of the stem cells into different types of neurons and neuron-supporting cells. In some cases, microfluidics technology is used to create a gradient of signaling molecules whose variable concentration instructs the stem cells to turn into different types of neurons and neuron-supporting cells including, for example, motor neurons, forebrain cortical glutamatergic neurons, GABAergic neurons, cholinergic neurons, and astrocytes.

Any appropriate method can be used to analyze biomimetic neural tissues comprising one or more or, preferably, a singular rosette structure. In preferred embodiments, the analysis method(s) are useful to detect the presence and identity of neurons and neuron-supporting cells (e.g., glia) in a biomimetic micropatterned neural tissue comprising a singular rosette structure. For example, confocal microscopy and other microscopy-based imaging methods can be used. In some cases, an automated method of detecting and analyzing singular rosette structures in biomimetic micropatterned neural tissues is used. In such cases, confocal microscopy can be used to collect multiple images of single micropatterned tissues that have been treated with detectably labeled antibodies or stains having specificity for various cell types present at particular stages of development of the human neural tube. As described in the Examples that follow, confocal images can be obtained of single micropatterned tissues fluorescently labeled to detect N-cadherin expression. For example, an exemplary protocol for detecting and analyzing singular rosette structures includes acquiring a series of confocal images using a 60× objective at 1024×1024 pixels to scan through the tissue vertically in user-defined increments or steps, and analyzing a stack of the acquired confocal images to detect rosette structures and cell types present in or adjacent to the rosette structures using, for example, a machine learning program for image classification.

II. Compositions

In a first aspect, provided herein is a cell culture substrate useful for producing biomimetic neural rosettes, preferably wherein a single biomimetic neural rosette is obtained. In some embodiments, the cell culture substrate comprises a solid support, and a micropatterned substrate configured to promote neural differentiation and morphogenesis of human pluripotent stem cells cultured on or recruited to the substrate, where the substrate is configured to promote differentiation of human pluripotent stem cells or neural stem cells into one or more biomimetic neural rosettes relative to control stem cells cultured on solid support lacking the micropatterned substrate.

In some cases, the micropatterned substrate comprises a plurality of peptide-immobilizing PEG brushes arranged in a user-defined, bounded geometry. Preferably, the bounded geometry has at least one dimension from side to side of the bounded geometry of about 100 µm to 800 µm. In some cases, the bounded geometry is a circle having a diameter of about 100 µm to about 500 µm. Preferably, the micropatterned substrate is configured to mimic the extracellular matrix and basement membrane of a mammalian cell.

In some cases, a micropatterned substrate is covered by or coated in a cell culture substrate. In some cases, the cell culture substrate can be an undefined extracellular matrix protein substrate such as Matrigel®. In other embodiments, a defined, xenogen-free cell culture substrate is used. Such substrates include, but are not limited to, vitronectin, a vitronectin fragment, a vitronectin peptide, and self-coating substrates such as Synthemax® (Corning). Other substrates include, without limitation, collagen, fibronectin, laminin, Arg-Gly-Asp (RGD) peptide, Tyr-Ile-Gly-Ser-Arg (YIGSR) peptide, gycosaminoglycans (GAGs), hyaluronic acid (HA), integrins, ICAMs, selectins, cadherins, and cell surface protein-specific antibodies.

In some cases, the micropatterned culture substrate is on a solid support. The solid support can be made of any material suitable for culturing mammalian cells. For example, the solid support can be a material that can be easily sterilized such as plastic or other artificial polymer material, so long as the material is biocompatible. A solid support can be made of any material that allows cells and/or tissue to adhere (or can be modified to allow cells and/or tissue to adhere or not adhere at select locations) including, but not limited to, polyamides; polyesters; polystyrene; polypropylene; polyacrylates; polyvinyl compounds (e.g. polyvinylchloride); polycarbonate (PVC); polytetrafluoroethylene (PTFE); nitrocellulose; cotton; polyglycolic acid (PGA); cellulose; dextran; gelatin, glass, fluoropolymers, fluorinated ethylene propylene, polyvinylidene, polydimethylsiloxane, polystyrene, and silicon substrates (such as fused silica, polysilicon, or single silicon crystals), and the like. Also metals (gold, silver, titanium films) can be used. The solid support can be chosen from any number of rigid or elastic supports. For example, solid supports can comprise glass or polymer microscope slides. In some aspect, the solid support may be selected based upon a cell type's propensity to bind to the support.

As will be recognized in the art, the micropatterned substrates disclosed herein may be used in any culture system including static (e.g., tissue culture plates) and fluid flow reactor systems (e.g., microfluidic devices). Such microfluidic devices are useful in the rapid screening of agents where small flow rates and small reagent amounts are required. Microfluidic devices are also useful for in vitro exposure of a micropatterned substrate to one or more gradients of transcription factors or other factors capable of directing neural differentiation.

In another aspect, provided herein are two-dimensional (2D) preparations of biomimetic neural tissues comprising a single rosette structure or multiple rosette structures. In some cases, the two-dimensional preparations are in vitro cellular compositions comprising polarized Pax6$^+$/N-cadherin$^+$ neural stem cells (NSCs) in a biomimetic neural tissue. In some embodiments, the in vitro cell composition comprises a single ring of polarized Pax6$^+$/N-cadherin$^+$ NSCs mimetic of the developing neural tube. Applications of in vitro cellular compositions provided herein include in vitro screening of agents for those that modulate neural tube or CNS development. For example, in vitro-derived compositions comprising one or more biomimetic neural rosettes can be used for high throughput screening of candidate agents.

In another aspect, provided herein is a plurality of two-dimensional (2D) preparations of biomimetic neural tissues having cellular architecture analogous to developing neural tube slice cultures. In particular, provided herein is a plurality of 2D preparations of biomimetic neural tissues that collectively provide an engineered, standardized model of the developing human CNS, in whole or in part. As described herein, micropatterned substrates are used to reproducibly obtain preparations of biomimetic neural tissues comprising a singular neural rosette structure with at least 80% efficiency and to further differentiate cells within the neural rosettes to produce biomimetic neural tissues having diverse neuronal cell types. In preferred embodiments, the biomimetic neural tissue preparations comprise diverse regional phenotypes found along the rostrocaudal (head-to-tail) axis and dorsoventral (back-to-front) axis of the central nervous system (CNS). These regional CNS phenotypes are described in U.S. application Ser. Nos. 13/795,485 and 14/496,796, each of which is incorporated herein by reference as if set forth in its entirety. For example, NMPs of various HOX expression profiles can be micropatterned to form a biomimetic neural tissue with a singular rosette structure as described herein. It can then be exposed to a transient boost of Wnt/β-catenin signaling followed by SHH signaling in order to "ventralize" its differentiation to produce a spinal motor neuron progenitor phenotype within its constituent cells as described in U.S. application Ser. No. 15/475,831, which is incorporated herein by reference as if set forth in its entirety.

In this manner, the micropatterned substrates described herein allow unprecedented control of neural stem cell tissue morphogenesis, which the current state-of-the-art methods lack. This discovery represents a significant advancement and universal basis for engineering anatomically biomimetic in vitro tissues that recapitulate stages of human CNS development. Standardized production of such biomimetic in vitro tissues provide a revolutionary experimental paradigm for conducting personalized neuroscience studies. For example, neural organoid tissues are useful to study the effects of genetic mutations on development and function across the human CNS, to conduct personalized neuroscience studies using neural stem cells derived from induced pluripotent stem cells (iPS cells) of a particular human subject, and to assess neurotoxicity of various agents or other effects on neural development. In some cases, engineered, micropatterned substrates of the invention are useful in drug discovery and development including screening for metabolic stability, drug-drug interactions, toxicity and infectious disease. Exemplary test agents include, without limitation, infectious agents, proteins, peptides, antibodies, small molecules, oligonucleotides, polynucleotides, peptidomimetics, cytotoxic agents, pharmaceutical agents, and xenobiotics (e.g., environmental toxin, chemical/biological warfare agent, a natural compound, and a nutraceutical).

In some cases, 2D preparations of biomimetic neural tissues as described herein can be screened to identify agents that modulate neural tube development and development of the human central nervous system (CNS). Screening methods can comprise or consist essentially of (a) contacting a test agent to one or more in vitro derived biomimetic neural rosettes; and (b) detecting an effect of the agent on biomimetic neural rosettes or cells derived therefrom (e.g., disrupt or otherwise alter development of the neural tube or differentiation of neural cell types from biomimetic neural rosettes). In some cases, screening methods include screening candidate compounds to identify test agents that promote the development of the human CNS. In other cases, candidate compounds can be screened for toxicity to human neural cell types or tissues. In some cases, detecting comprises detecting at least one positive or negative effect of the agent on morphology or life span of such cells and tissues, whereby an agent that increases or reduces the life span of human neural cell types or tissues, or has a positive or negative impact on the morphology of human neural cell types or tissues, is identified as having an effect on development of the human neural tube or neural tissues. In some cases, detecting comprises performing a method selected from the group consisting of RNA sequencing, gene expression profiling, transcriptome analysis, cell proliferation assays, metabolome analysis, detecting reporter or sensor, protein expression profiling, Förster resonance energy transfer (FRET), metabolic profiling, and microdialysis. In some cases, the agent can be screened for an effect on gene expression, and detecting can comprise assaying for differential gene expression relative to an uncontacted biomimetic neural rosettes or cells derived therefrom.

In exemplary embodiments, detecting and/or measuring a positive or negative change in a level of expression of at least one gene following exposure (e.g., contacting) of a test compound to one or more biomimetic neural rosettes comprises whole transcriptome analysis using, for example, RNA sequencing. In such cases, gene expression is calculated using, for example, data processing software programs such as Light Cycle, RSEM (RNA-Seq by Expectation-Maximization), Excel, and Prism. See Stewart et al., *PLoS Comput. Biol.* 9:e1002936 (2013). Where appropriate, statistical comparisons can be made using ANOVA analyses, analysis of variance with Bonferroni correction, or two-tailed Student's t-test, where values are determined to be significant at P<0.05. Any appropriate method can be used to isolate RNA or protein from neural constructs. For example, total RNA can be isolated and reverse transcribed to obtain cDNA for sequencing.

Test compounds can be dissolved in a solvent such as, for example, dimethyl sulfoxide (DMSO) prior to contacting to one or more biomimetic neural rosettes provided herein. In some cases, identifying agents comprises analyzing the contacted biomimetic neural rosettes for positive or negative changes in biological activities including, without limitation, gene expression, protein expression, cell viability, and cell proliferation. For example, microarray methods can be used to analyze gene expression profiles prior to, during, or following contacting the plurality of test compounds to the biomimetic neural rosettes. In some cases, a method of the present invention further comprises additional analyses such as metabolic assays and protein expression profiling.

IV. Article of Manufacture

In another aspect, provided herein is a kit comprising one or more components useful for obtaining an in vitro cellular composition. Components of the kit can include one or more micropatterned substrates as described herein. The kit can also contain a chemically defined culture medium and one or more medium additives. In another aspect, provided herein is a kit comprising one or more components useful to prepare a 2D model of the developing human neural tube according to the methods provided herein. Components of the kit can include one or more micropatterned substrates as described herein.

The invention will be more fully understood upon consideration of the following non-limiting Examples.

EXAMPLES

Example 1—Controlled Neural Rosette Induction

The derivation of organoids from human pluripotent stem cells (hPSCs) or their early-stage germ layer progenitors has redefined the possibilities of in vitro tissue engineering. Human PSCs have traditionally been characterized by their ability to spontaneously recapitulate facets of developmental tissue morphogenesis upon ectopic implantation in vivo, i.e. the teratoma assay[1]. However, recent discovery of their ability to also self-organize emergence of organotypic tissues ex vivo, e.g., cortical[2], retinal[3], cerebral[4], and intestinal organoids[5], has spurred the creation of novel developmental and disease models with unprecedented biomimicry of microscale cytoarchitectures and cell phenotype diversity[6,7]. These innate emergent properties of hPSCs could one day serve as the basis for advanced biomanufacture of functional tissue and organ models or transplants[5,8]. Yet, it remains a challenge to engineer reproducible hPSC morphogenesis in vitro and thereby enable controlled emergence of organotypic tissues with consistent and standardized cytoarchitecture[9,10].

Human central nervous system (CNS) and hPSC-derived neural organoid morphogenesis both commence with neurulation of columnar neuroepithelial cells (NECs), also known as polarized NSCs. In this dynamic process, NSCs polarize adherens, e.g., N-cadherin, and tight junction proteins towards an apical lumen while depositing extracellular matrix (ECM) proteins at their basal surface. In vivo, neurulation results in emergence of a singular neuroepithelial tube that spans the entire rostrocaudal (R/C) axis of the embryo's dorsal plane and serves as the primordium of all brain, retinal, and spinal cord tissues. This singular polarized neuroepithelium serves as a critical morphogenesis center for organizing development of lamellar tissue cytoarchitectures during subsequent stages of CNS morphogenesis. For example, it localizes waves of mitotic NEC proliferation at the tube's apical surface while daughter cells migrate radially towards the basal surface to complete differentiation and functional maturation and expand the CNS parenchyma. Disruption of the neuroepithelial tube's N-cadherin polarized cytoarchitecture eliminates the sole neurogenic source of embryonic CNS development[11]. Alternatively, the presence of multiple neural tubes during development causes congenital abnormalities such as dipolmyelia and diastematomyelia[12,13] or anencephaly as observed in diprosopic parapagus twins[14]. Therefore, formation of singular neuroepithelial tissues within hPSC-derived organotypic tissues is an important cytoarchitectural feature for generating biomimetic CNS tissue models[15].

In current 2- and 3-D hPSC-derived cultures, neurulation occurs spontaneously yielding uncontrolled emergence of numerous polarized neuroepithelial tissues, a.k.a neural rosettes[4,16]. Integration of engineering techniques such as stirred-tank bioreactor culture during neural organoid derivation can induce the formation of larger and more contiguous neuroepithelial tissues[4]. Likewise, derivation of neural organoids around filamentous biomaterial scaffolds was shown to induce elongated neuroepithelial tissues within 3-D organoids[17]. Yet, the persistent presence of multiple neural rosettes of indiscriminate shapes and sizes within a single tissue inevitably confounds subsequent morphogenesis events, potentially limits tissue maturation, and produces significant variability in the resulting cytoarchitecture[4]. Interestingly, singular neural rosette emergence was routinely observed upon derivation of neuroepithlelial cysts, which have considerably smaller dimensions than hPSC-derived organoids, from a single cell suspension of mouse embryonic stem cells (mESCs)[18,19]. However, manual isolation and re-plating of singular neural rosettes remains the only reliable in vitro method for generating such critical biomimetic cytoarchitecture within hPSC-derived organotypic CNS tissues[20].

Geometric confinement of hPSC tissues on 2-D micropatterned substrates was recently shown to induce self-organized embryonic patterning, i.e., gastrulation, in a morphology dependent manner[21,22]. Based on this and previously discussed mESCs studies, we investigated whether engineering the morphology of neurally differentiating hPSC tissues could similarly regulate their morphogenesis including neural rosette emergence. Neural rosette formation was observed to be a function of local cell density and acquisition of a Pax6$^+$/N-cadherin$^+$ neuroectodermal fate in both standard well-plate and 2-D micropatterned culture. Using an automated workflow consisting of a custom image analysis algorithm and machine learning classifier, screens of hPSC-derived NSC tissues of various morphologies revealed an indirect correlation between the tissue's surface area the propensity for singular neural rosette emergence. Circular micropatterns of 200-250 μm diameter (0.03-0.049 mm$^2$) were observed to most effectively induce singular neural rosette emergence within forebrain neuroepithelial tissues reaching levels of 80-85% efficiency when initially seeded as hPSCs. These studies were further extended to develop an analogous protocol for neuroepithelial tissues of a ventral spinal cord regional phenotype. This revealed that spinal neuroepithelial tissues, unlike there forebrain counterparts, preferentially formed singular neural rosettes (73.5%) on circular micropatterns of 150 μm diameter (0.018 mm$^2$), indicating unique biophysical differences between NECs of varying regional phenotypes. During the rosette emergence period, the proliferative neural tissues morphed from a 2-D monolayer to a 3-D multilayered, disk morphology of the prescribed micropatterned diameter. Upon release from micropattern confinement, the tissue slices expanded radially while maintaining a singular neuroepithelial rosette as the morphogenesis center, depositing a basal lamina, and displaying neuronal differentiation at the tissues' periphery. Thus, we have developed a culture platform for engineering controlled neural rosette emergence within hPSC-derived organotypic CNS tissues. Reproducible induction of this nascent cytoarchitecture is a prerequisite for advanced biomanufacture of human CNS organoids with consistent, biomimetic anatomy.

Results

Characterization of Neural Rosette Emergence in Well Plate Culture:

Forebrain NECs were derived from hPSCs using our previously published, chemically defined E6 protocol[23]. In six days and without the use of SMAD inhibitors[24], the E6 protocol generates near homogenous monolayers of Pax6$^+$/Sox2$^+$/N-cadherin$^+$ NECs that undergo spontaneous neurulation to produce cultures densely populated with neural rosettes of varying shapes and sizes (FIG. 1A). To better characterize neural rosette emergence, we conducted a time course analysis using Pax6 and N-cadherin immunostaining (FIG. 1B). In agreement with previous studies[23], the onset of Pax6 expression, a human neuroectodermal fate determinant[25], began between days 2 (0%) and 3 (44±15%) of the E6 protocol (FIGS. 1C-D). By day 3 and concurrent with increasing Pax6 expression, the presence of polarized N-cadherin$^+$ foci were observed. By day 5, Pax6 expression had reached 81±5% and N-cadherin$^+$ polarization foci had both increased in prevalence and morphed into coherent rings surrounded by contiguous alignment of polarized NECs, which is characteristic of neural rosettes. Thus, neural rosette emergence occurs over five days after commencing E6 culture in 6-well plates with correlated and progressive increases in Pax6 expression and N-cadherin polarization.

Characterization of Neural Rosette Emergence within Micropatterned Tissues:

Hundreds of neural rosettes form spontaneously and randomly upon NEC derivation in vitro (FIG. 1A). We hypothesized that the prevalence of neural rosettes could be regulated by controlling tissue size and geometry. This was corroborated by our previous observation that ~0-4 neural rosettes routinely form within micropatterned, 300 μm diameter circular NEC tissues[26]. Based on the temporal dynamic of rosette formation observed in well plate culture (FIGS. 1B-1D), we first characterized the time of neural rosette emergence within micropatterned neural tissues. NECs were harvested on day 4 of the E6 protocol (D4 NSCs), which corresponded with increasing Pax6 expression and rosette formation capacity (FIG. 1E). Next, they were seeded at 75,000 cells/cm$^2$ onto micropatterned, poly(ethylene glycol methyl ether)-grafted substrates presenting arrays of 300 μm diameter circular regions (0.071 mm$^2$) coated with MATRIGEL™ (FIG. 13A)[27,28]. Time course analysis over the next 8 days using Pax6 and N-cadherin immunostaining revealed several distinct stages of rosette emergence that we classified as pre-polarization (~day 7), polarization foci (~day 8), neural rosette (~day 9), and contraction (~day 13) (FIG. 1F). Interestingly, despite being D4 NECs upon seeding onto micropatterned substrates, ~5 days of additional E6 culture was still required for neural rosette emergence similar to well plate culture (FIG. 1C). The 5 day time point also correlated with the highest occurrence (30%, n=100 tissues) of singular rosette emergence within micropatterned NEC tissues (FIG. 1G). Additionally, the NECs appeared to proliferate within micropatterned tissues after seeding as indicated by increased Pax6$^+$ cell density (e.g., day 7 vs 9, FIG. 1F).

Figures 13A, 13B, 13C:
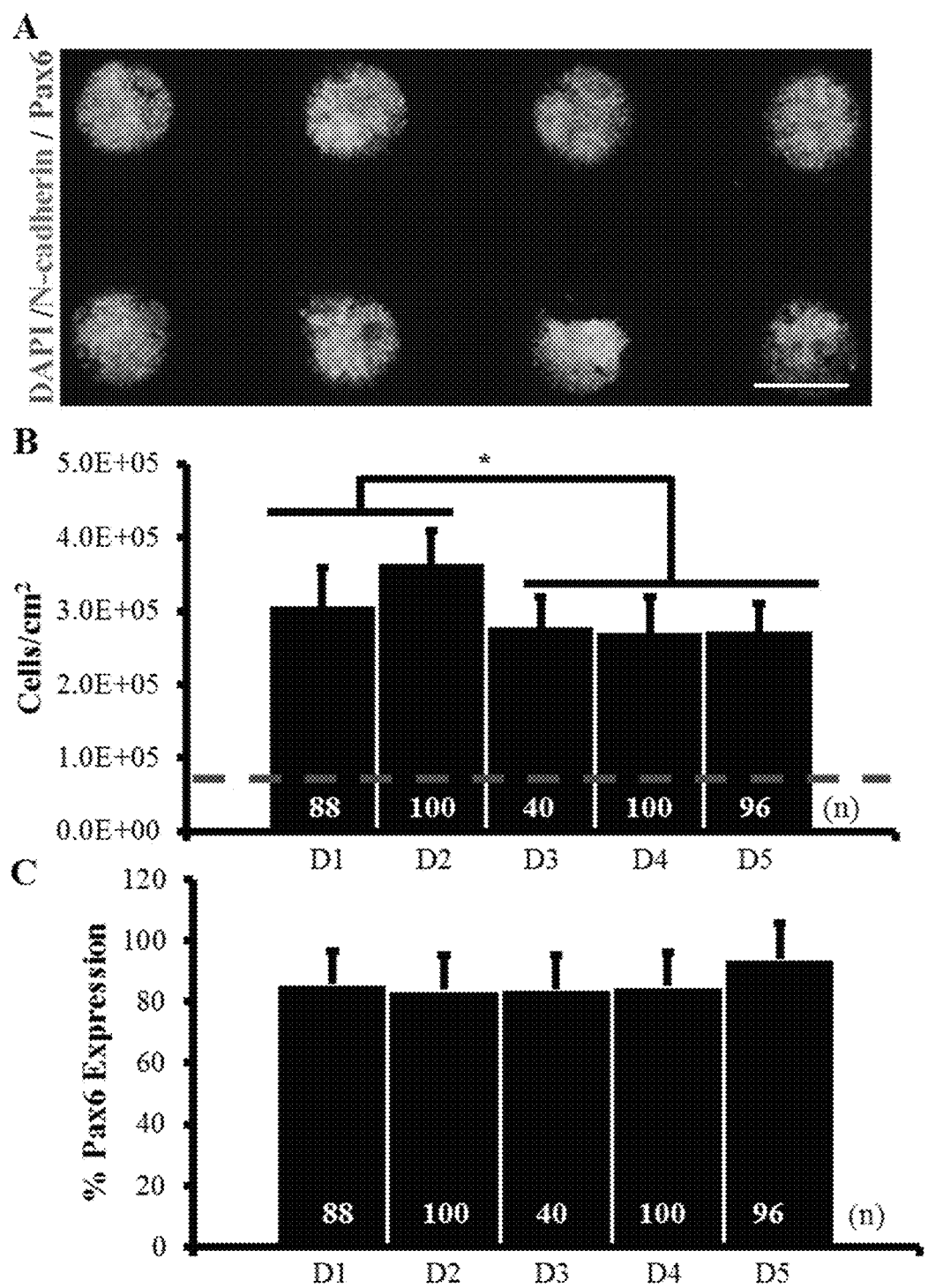
FIGS. 13A-13C. (A) A low magnification image of a micropatterned NSC tissue array. Scale bar is 300 μm. (B) The average cell density within micropatterned neural tissues from the same arrays as those shown in FIG. 1I. The number of analyzed tissues per microarray/condition is indicated within each bar. * indicates p<0.05 according to a one-tailed ANOVA. (C) The average percentage of Pax6+ cells per micropatterned neural tissue from the same arrays as those shown in FIG. 1I. The number of analyzed tissues per microarray/condition is indicated within each bar.

Persistence of the approximate 5 day time course for neural rosette emergence in E6 media, whether seeding hESCs at 150,000 cells/cm$^2$ in well plates or D4 NECs at 75,000 cells/cm$^2$ on micropatterned substrates, indicates that temporal aspects of rosette emergence may rely on a conserved aspect of E6 culture. As a final test of the 5-day paradigm, we investigated whether seeding Pax6$^+$ cultures on micropatterned substrates was requisite for adherence to the 5 day neural rosette emergence time course. Neurally differentiating cultures were subcultured at day 1, 2, 3, 4, and 5 of the E6 protocol, i.e., Pax6 expression being absent in D1-2 and present in D3-5 cultures. The cells were re-seeded onto 300 um diameter (0.071 mm$^2$) circular micropattern arrays. Cultures were maintained in E6 media for 5 days prior to fixation and immunostaining (FIG. 1H). In all conditions, the cells proliferated and produced neuroepithelial tissues with at least a 2-fold increase in cell density, >80% Pax6 expression, and consistent neural rosette formation (FIG. 1I and FIGS. 13B-13C). Of note, all tested cell phenotypes were observed to initially adhere as monolayers in well plates or on micropatterned substrates even when the seeding density was increased by several folds (data not shown). These results indicate that a 5 day paradigm for neural rosette emergence in E6 media holds for cultures seeded at all stages of hESC neural induction and appears to be a function of Pax6 expression and local cell density. From here onward, a 5 day culture period was used to assess neural rosette emergence.

Neural Rosette Emergence is Regulated by Tissue Morphology:

The previous experiments demonstrate that switching from a 9.6 cm$^2$ (a well in a 6-well plate) to a 0.071 mm$^2$ (300 μm diameter) circular neuroepithelial tissue can substantially reduce the number of emerging neural rosettes. However, formation of neuroepithelial tissues with a biomimetic, singular rosette was not highly reproducible (about 30%, FIG. 1G). Biophysical studies have inextricably linked developmental morphogenesis events such as neural tube formation with tissue biomechanics[28,29]. Specifically, studies on micropatterned cultures have observed that muticellular tissues contract as a unit, generating gradients of mechanical stresses with maximal cytoskeletal forces arising at their periphery and in spatial distributions dependent upon tissue morphology[30]. Therefore, we hypothesized that the reproducibility of singular rosette emergence could be further improved by varying neuroepithelial tissue morphology, i.e., size and geometry.

Figures 2A, 2B, 2C, 2D:
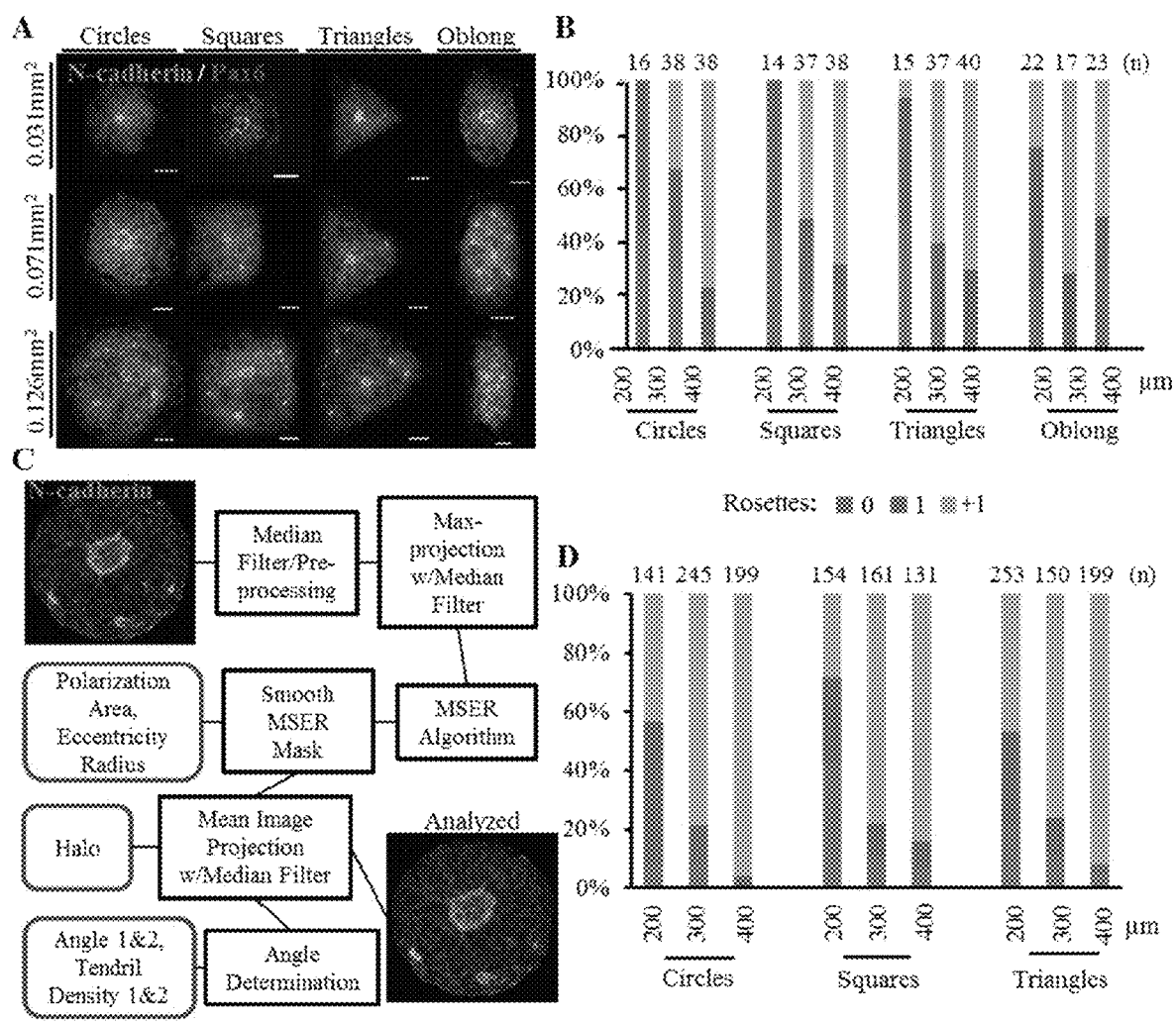
FIGS. 2A-2D. (A) Polarized NSC tissues on single micropatterned regions of various geometry and dimension 5 days post-seeding. Scale bars are 50 μm. (B) Representation of manually analyzed single neural rosette efficiency corresponding to micropattern morphology. (C) Exemplary algorithm for automated analysis of micropatterned NSC tissues. (D) Representation of single neural rosette efficiency generated from automated analysis of 1633 images of NSC-derived tissues of various micropatterned morphology.

This hypothesis was tested by assessing singular rosette induction efficiency within micropatterned neuroepithelial tissues of circular, triangle, square, and oblong morphologies of varying sizes (FIG. 2A). Culture substrates were designed to normalize the surface area of all tissue morphologies of a given size scale to 200 (0.031 mm$^2$), 300 (0.071 mm$^2$), or 400 μm (0.126 mm$^2$) diameter circular micropatterns. In this manner, the cell seeding density would be constant amongst tissues of differing morphologies within the same size scale. Day 4 NECs were seeded onto 0.031, 0.071, and 0.126 mm$^2$ micropattern arrays at 33,300, 75,000, and 133,000 cells/cm$^2$, respectively, to correspond with changes in micropattern cell-adhesive area across each size scale. After 5 days in E6 media, the cultures were fixed, immunostained for Pax6 and N-cadherin, and analyzed manually to quantify the number of N-cadherin$^+$ polarization foci and rosettes (FIG. 2B). Each tissue was categorized as follows: the presence of 0 or 1 polarization foci were '0 Rosette'; 1 rosette and 0 polarization foci were '1 Rosette'; >1 rosette with >1 additional polarization foci were '+1 Rosette". Although all micropatterned tissue morphologies exhibited the capacity to induce '1 Rosette' neuroepithelial tissues, 200 μm (0.031 mm$^2$) circular (56%) and square (57%) morphologies were the most efficient. Yet, manual analysis of each image limited our ability to screen larger sample sizes per tissue morphology.

To increase sample size, an automated workflow consisting of an image analysis algorithm and machine learning classifier was developed to quantitatively characterize and classify N-cadherin polarization foci and rosettes within micropatterned tissues (FIG. 2C and FIG. 6). The automated workflow was used to analyze a total of 1633 images of neuroepithelial tissues with circular, triangle, and square morphologies across 0.031, 0.071, and 0.126 mm$^2$ surface area size scales. Compared to manual assessment, image analysis using the automated workflow estimated lower percentages of singular rosette emergence efficiency across all tissue morphologies. This was expected since the classifiers rosette identification error rate is primarily due to false positive (i.e., erroneously classifying a polarization foci as rosette). However, the trends in single rosette emergence efficiency were consistent with manual assessment in FIG. 2B. The probability of biomimetic, singular rosette emergence increased as the neuroepithelial tissue's surface area decreased. Interestingly, the automated analysis of increased sample size suggests that 200 μm diameter (0.031 mm$^2$) circular versus square or triangle morphologies is more efficient at inducing singular rosette emergence, i.e., 48.9% vs. 29.9% vs. 31.2%, respectively (FIG. 2D).

The MATLAB® Machine Learning Toolbox was used to develop a classifier function based on 76 randomly selected images of 300 μm diameter (0.071 mm$^2$) circular tissues. In addition to the image analysis algorithm's descriptor data, these images were also examined independently by five NSC culture experts, who were asked to quantify the total number of N-cadherin$^+$ polarization areas (i.e., foci) and determine which should also be classified as rosettes. Agreement between 4 out 5 experts was required to designate any polarization foci or rosette as a 'ground truth'. Then, the human ground truth and the algorithm's descriptor data for each identified N-cadherin polarization area in the 76 images (235 total identified areas) was used to develop a classifier function in MATLAB®. Analysis of each human expert's image data versus the consensus ground truth revealed a human polarization and rosette identification error rate of 11.90±5.80% and 9.20±3.91%, respectively (FIG. 15A). In comparison, the classifier function exhibited similar error rates of 14.35% and 8.86%, respectively. To further validate the classifier, a second round of human expert and algorithm analyses was conducted on an additional 36 images selected randomly and distributed evenly across all NSC tissue morphologies. The human experts and automated image analysis algorithm identified 149 N-cadherin polarization areas total. The human versus classifier polarization and rosette error rates were 19.05±14.61% vs. 20.27% and 9.93±6.96% vs. 19.56% (FIG. 15B). Despite the increase in the classifier's rosette identification error rate, the automated image analysis and classifier workflow was deemed acceptable for detecting trends in singular rosette emergence given the magnitude of differences observed in FIG. 2B.

Seeding at the hESC State Increases Singular Neural Rosette Emergence with Forebrain Neuroepithelial Tissues:

A significant increase in neuroepithelial cell density was noted between tissues formed using Pax6– D1-2 cultures versus Pax6+D3-5 cultures (FIG. 5B). Thus, we hypothesized that rosette emergence could be affected by the micropatterned cells' proliferative capacity over 5 days of E6 culture. This was tested using the disparate cell phenotypes encountered during E6 neural induction, i.e., Pax6– hESCs (D$^-$1) and Pax6$^+$D4 NECs (FIG. 3A). Both cell types were seeded onto 200 μm diameter (0.031 mm$^2$) circular micropatterned arrays at 75,000 cells/cm$^2$ in biological duplicate, fixed, and immunostained after 5 days (FIG. 3B). In all tissues, the cells obtained a Pax6+/Otx2+ dorsal forebrain phenotype (23) with near uniformity. Manual analysis of over 100 neuroepithelial tissues in each experiment revealed a singular neural rosette emergence efficiency of 80.0±0.05% vs. 38.6±4.7% for neuroepithelial tissues formed by seeding hESCs vs. D4 NECs, respectively (FIG. 3C). The average cell density of neuroepithelial tissues formed using hESC vs. D4 NECs was ~1.25 fold higher after 5 days of E6 culture or ~30 more cells per tissue, i.e., 149±23 vs. 119±18 cells respectively (FIG. 3D). Although all tissues were multilayered, this change in cell density correlated with differences in neuroepithelial tissue morphology. Singular rosettes tissues derived from D⁻1 hESCs exhibited apico-basal polarity from a wider, central N-cadherin ring, while D4 NEC-derived singular rosette tissues had a tighter N-cadherin ring and appeared to have contracted slightly from their initial boundary (FIGS. 3B, 3E, and 3F). Hence, E6 culture of hESCs on 200 µm diameter (0.031 mm²) circular micropatterns induces highly reproducible, singular rosette emergence within forebrain neuroepithelial tissues in part due to their increased proliferative capacity.

Controlled Induction of Region-Specific, Singular Neural Rosette Tissues:

The NEC polarized morphology is consistent throughout all regions of the primordial neural tube. However, their gene expression profile induced by morphogenetic patterning varies along both the neural tubes' rostrocaudal (R/C)[33] and dorsoventral (D/V)[34,35] axes. NECs derived using the E6 protocol patterns a default Pax6⁺/Otx2⁺ dorsal forebrain phenotype both in well plate and micropatterned tissue culture (FIG. 3B). We have also published a protocol for deriving NECs of discrete hindbrain through spinal cord regional phenotypes via deterministic patterning of their HOX expression profiles (FIG. 4A)[36]. The protocol begins with high density seeding of hPSCs on day -1 (D⁻1) followed by induction of a stable neuromesodermal progenitor (NMP) phenotype using sequential activation of FGF8b and Wnt signaling. Upon addition of the Wnt agonist (CHIR), HOX expression proceeds in a colinear and combinatorial manner over 7 days. At any time point within those 7 days, the NMPs can be differentiated into NECs by transitioning from a FGF8b/CHIR-supplemented medium to a retinoic acid (RA)-supplemented E6 media. Based on the time point at which this transition is made, the resulting NECs will express a distinct HOX profile indicative of phenotypical patterning to a discrete hindbrain thru spinal cord R/C region. To enable highly reproducible derivation of biomimetic neural tissues from forebrain through spinal cord regions, we investigated how to integrate the HOX patterning protocol with the micropatterning methodology for inducing singular neural rosette emergence.

Figures 4A, 4B, 4C, 4D, 4E:
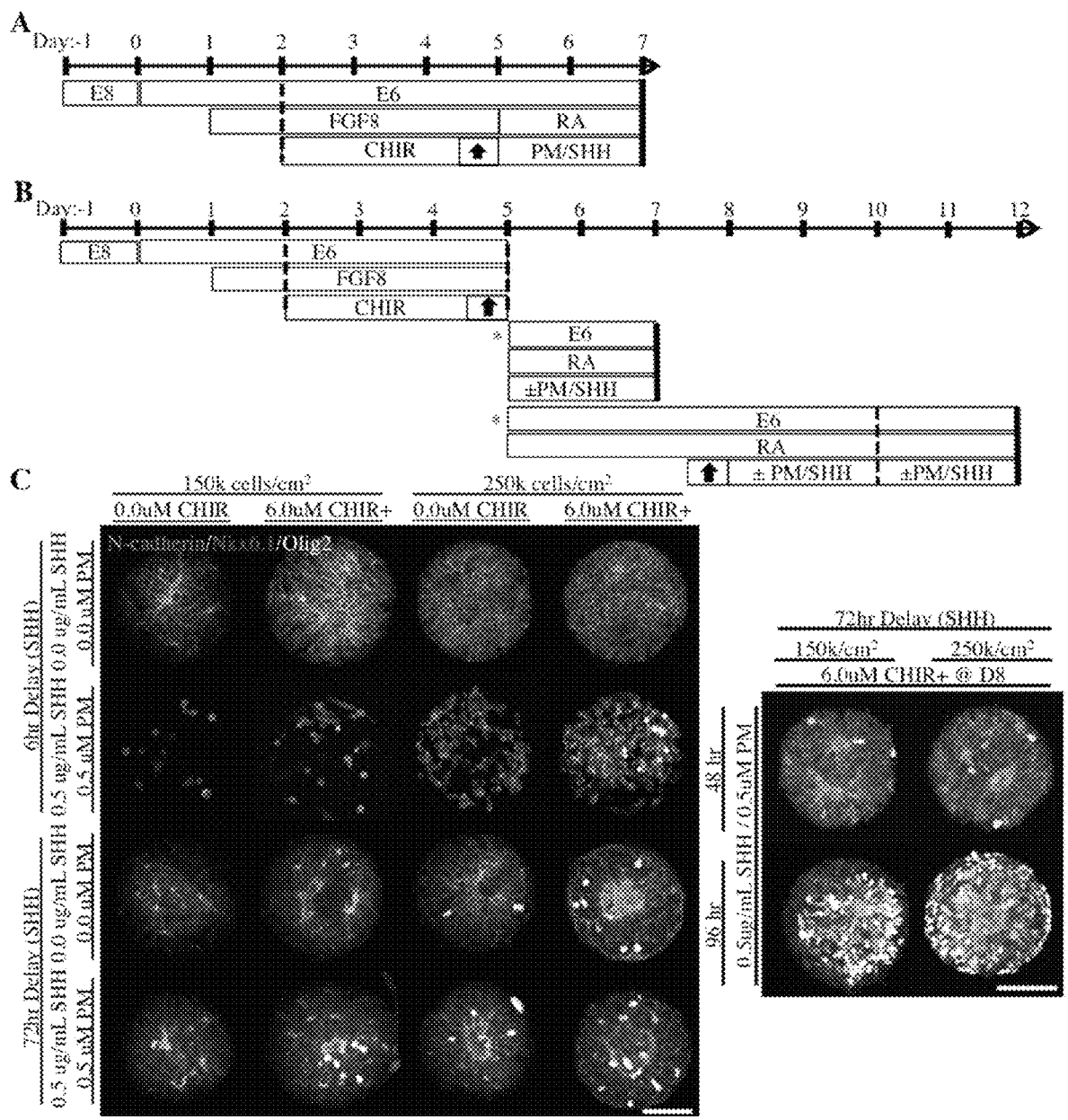
FIGS. 4A-4E. (A) Schematic timeline for derivation of spinal motor neurons progenitors (pMNs) from hESCs in well plate culture. (B) Schematic timeline depicting experimental translation of FIG. 4A's well plate timeline into one suitable for derivation of spinal tissues containing a singular rosette and motor neurons progenitors on micropatterned culture substrates. Timing of subculture onto micropatterned substrates indicated by *. (C) Nkx6.1 and Olig2 expression in spinal tissues derived on 200 µm diameter circular micropatterned substrates in response to varied timing, concentration, and duration of exposure to Sonic Hedgehog (SHH) or a small molecule agonist of SHH signaling (Purmorphamine (PM)) and a transient increase ("boost") in Wnt (CHIR) signaling as indicated in FIG. 4B. Scale bars are 100 µm.

The mitogenic properties of FGF8 and Wnt prevent direct transfer of the HOX patterning protocol to D⁻1 hESC-seeded micropatterned substrates. After only a few days, the cells would proliferate to such a great extent that they would form spheroids that detached from the culture surface. Given our prior positive results with seeding Pax6⁻ cells (FIGS. 1H-1I and FIG. 3), we explored whether seeding Pax6⁻/Sox2⁺/T⁺ NMPs instead would still permit highly robust neural induction and singular rosette emergence. In this manner, the NMP culture could be caudalized to the desired R/C position using standard 6-well plate culture, and then seeded onto micropatterned substrates concurrent with transitioning to RA supplemented media to generate NECs (FIG. 4B). For these experiments, we targeted derivation of HoxB4⁺, cervical spinal cord NECs using a 72-hour caudalization (i.e., CHIR exposure) period, which is known to pattern a lower brachial cervical/thoracic regional phenotype (36). Regional patterning was confirming by qRT-PCR (FIG. 4E). Additionally, the ability to induce dorsoventral patterning with a transient spike in Wnt followed by sustained Sonic Hedgehog (SHH) signaling during neural induction was also tested. SHH signaling can be sustained using SHH or a small molecule agonist of SHH signaling (Purmorphamine (PM)). Both the transient Wnt[37] and sustained SHH[38] signaling are known regulators of ventral spinal patterning in vivo.

Figure 5:
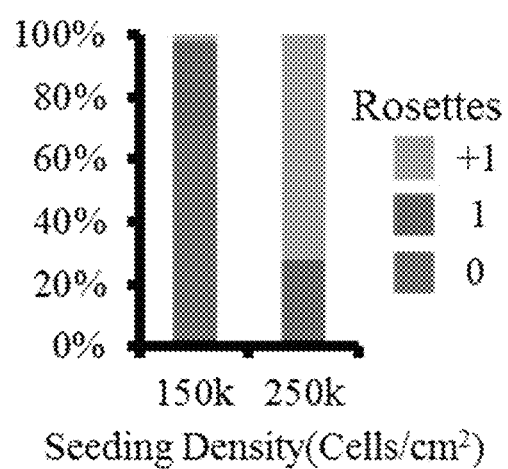
FIG. 5 demonstrates quantification of polarization foci/rosettes per tissue with the number of tissues (technical replicates) analyzed per condition indicated above each bar.

Using a combinatorial experimental design, the following variables were tested with cervical NMPs on 200 µm diameter (0.031 mm²) circular micropatterns: (1) NMP seeding density; (2) timing of initiating ventral patterning, i.e., adding SHH and Purmorphamine (PM), a SHH agonist; (3) the application and timing of a transient Wnt (CHIR) boost; (4) the duration of SHH ventralization (FIGS. 4B-4C). Rosette formation and ventralization were assessed by N-cadherin and Nkx6.1/Olig2, co-markers of spinal motor neuron progenitors, immunostaining, respectively[23]. Manual tissue analysis of neuroepithelial tissues in each condition revealed that the optimal protocol regimen included seeding cervical patterned NMPs at 2.5×10⁵ cells/cm² onto micropatterned substrates, culturing in RA supplemented E6 media for 72 hours, and applying a 6 hour, 6.0 µM Wnt boost immediately prior to 96 hours of 0.5 µg/mL SHH and 0.5 µM PM exposure (FIG. 4C). Waiting 72 hours after NMP seeding before applying the Wnt boost followed by SHH/PM exposure was the only tested regimen that consistently yielded both good cell viability and tissue formation as well as effective ventral patterning, i.e., 86±11% (n=8) Nkx6.1+/Olig2+(FIGS. 4C-4D). Yet, only ~12% (n=97) of neuroepithelial tissues on 200 µm diameter (0.031 mm²) circular micropatterns displayed singular neural rosette emergence (FIG. 5).

Figures 6A, 6B, 6C:
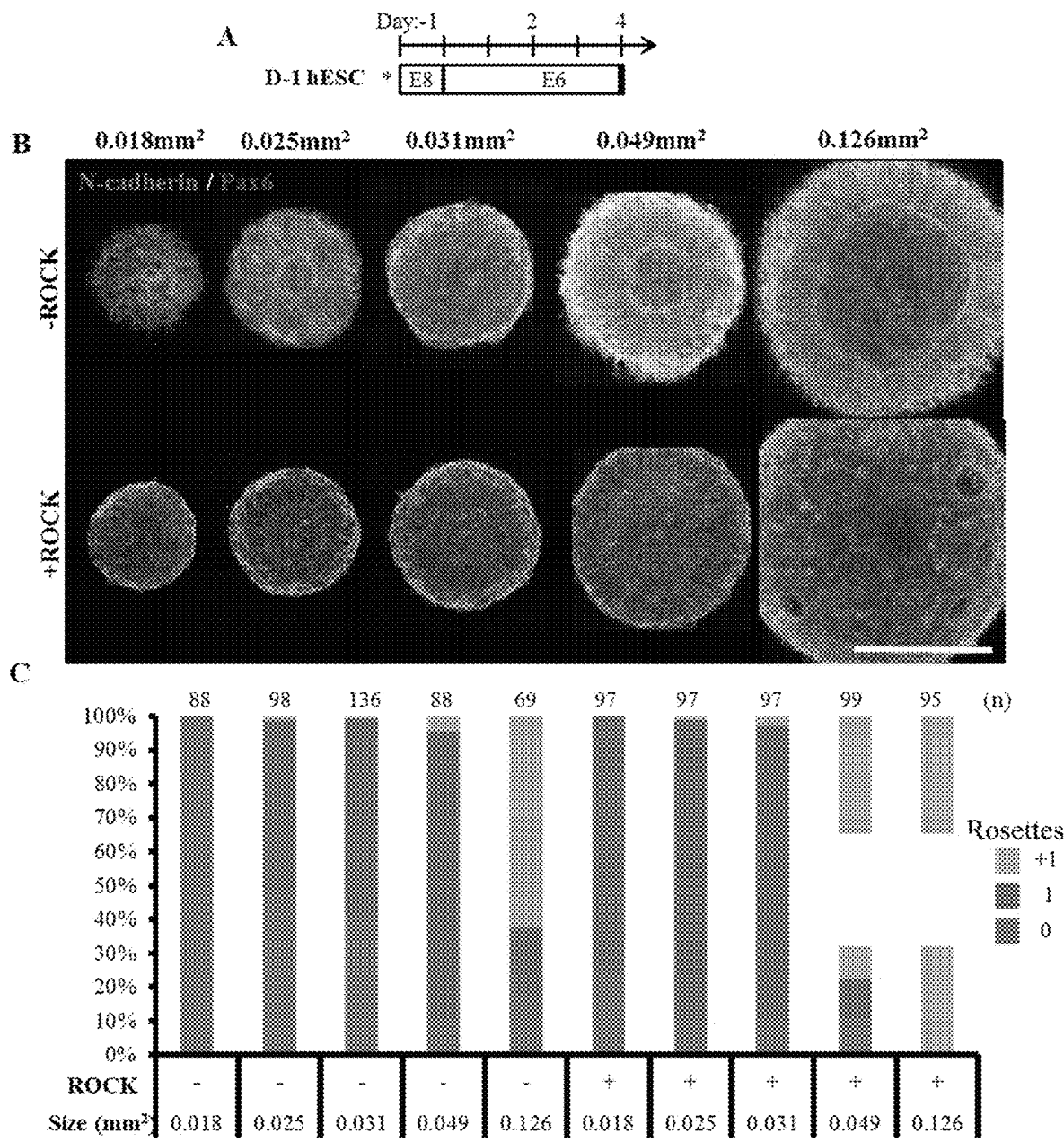
FIGS. 6A-6F demonstrate singular neural rosette emergence within forebrain and spinal neuroepithelial tissues. (A) Schematic for derivation of micropatterned forebrain neuroepithelial tissues; subculture/seeding onto micropatterned substrates indicated by (*). (B) Representative images of neural rosette emergence in micropatterned forebrain neuroepithelial tissues of various areas with and without ROCK inhibitor. (C) Quantification of polarization foci/rosettes per forebrain tissue with the number of tissues analyzed per condition above each bar. (D) Schematic for derivation of micropatterned spinal neuroepithelial tissues; subculture/seeding onto micropatterned substrates indicated by (*). (E) Representative images of neural rosette emergence in micropatterned spinal cord neuroepithelial tissues of various areas with and without ROCK inhibitor. (F) Quantification of polarization foci/neural rosettes per spinal tissue with the number of tissue (technical replicates) analyzed per condition above each bar. Scale bars are (B, F) 200 µm.
Figures 6D, 6E, 6F:
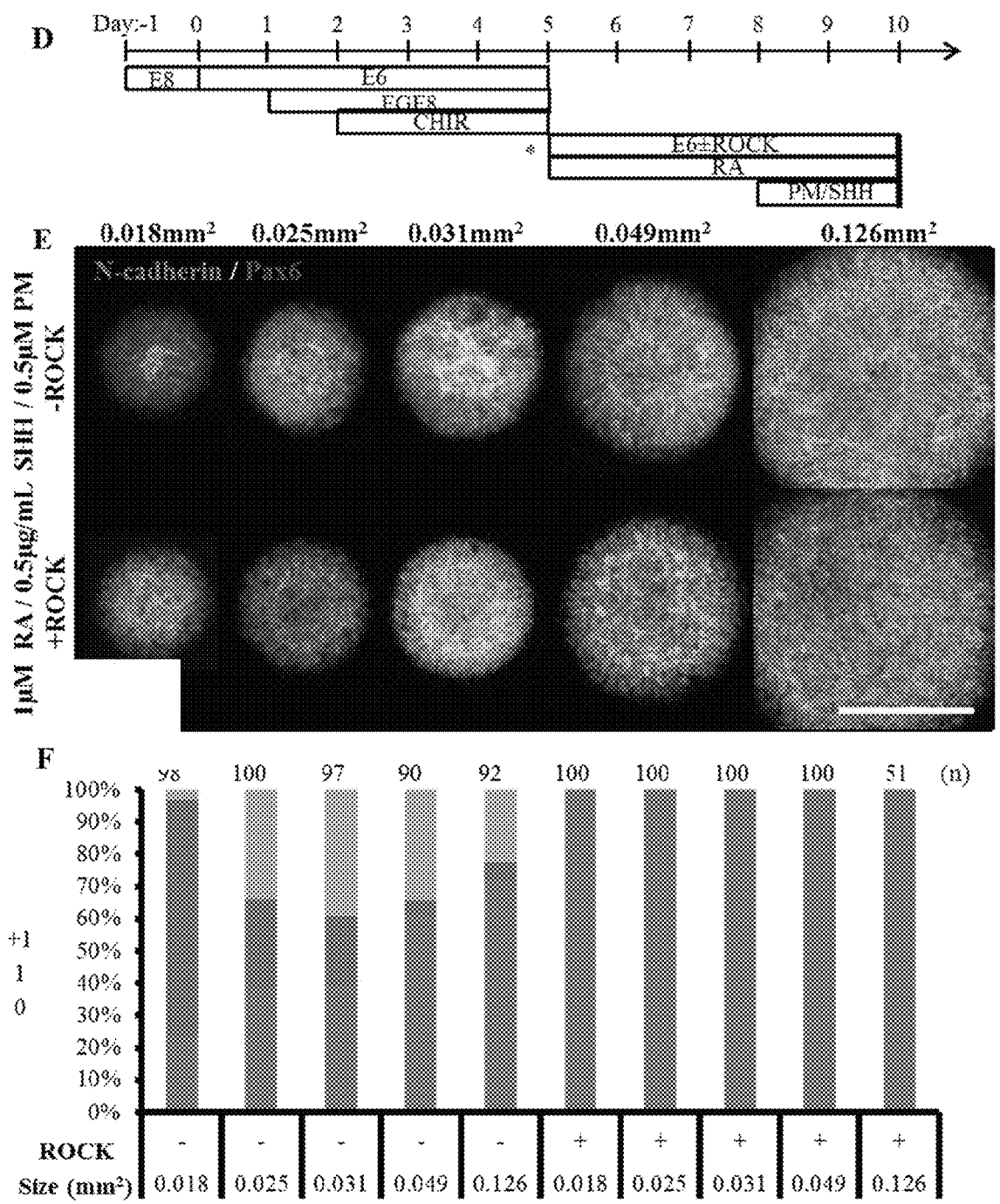
Figure 7:
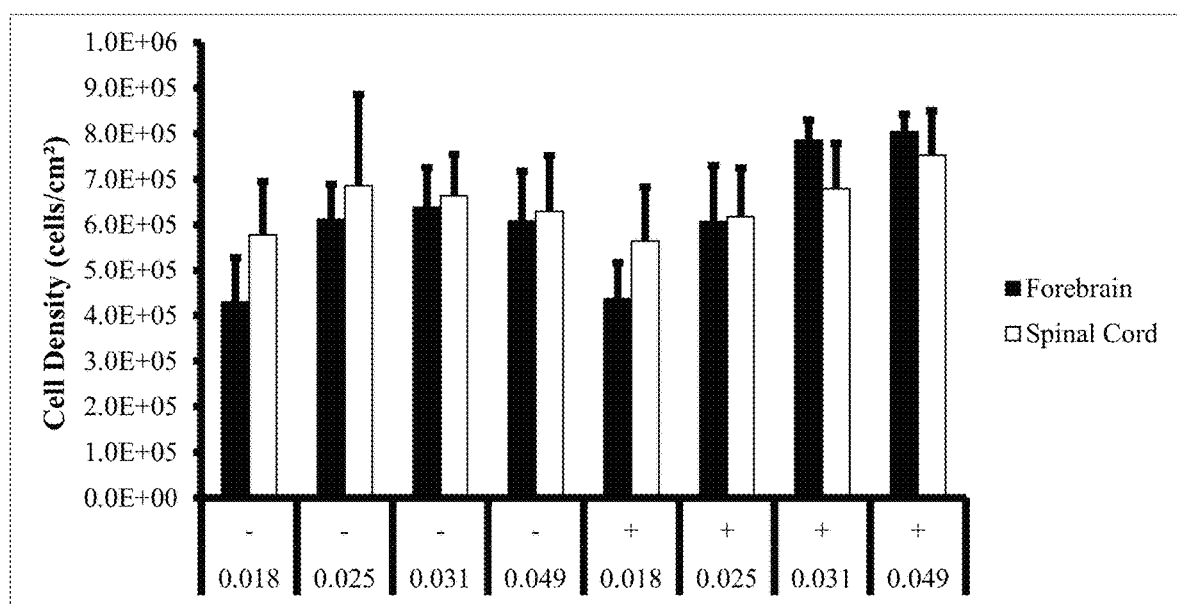
FIG. 7 demonstrates cell density analysis of forebrain and spinal cord neuroepithelial tissues. Average NEC density compared between forebrain and spinal cord tissues on 150, 180, 200, and 250 um diameter circular micropatterns in the absence or presence of ROCK inhibition. Number of tissues (technical replicates) analyzed presented above each condition. Pairwise Student's t-Test indicated no significant differences between tissues of equivalent dimensions in the absence or presence of ROCK inhibition or between forebrain and spinal cord tissues in each condition. Error bars represent standard deviation.

NEC Biomechanical Properties Vary by Regional Phenotype and Affect Rosette Emergence Behavior:

The inefficient induction of singular rosette emergence in spinal neuroepithelial tissues under micropatterning conditions that were highly efficient for forebrain NECs prompted a re-examination of the optimal circular micropattern size for each regional phenotype. Moreover, we investigated how altering the biomechanical properties of each regional neuroepithelial tissue, by partial inhibition of the Rho-associated protein kinase (ROCK), would affect which micropattern size induced optimal singular rosette emergence. D-1 hESCs and 72-hr caudalized NMPs were seeded at 100,000 and 250,000 cells/cm², respectively, onto 150 (0.018 mm²), 180 (0.025 mm²), 200 (0.031 mm²), 250 (0.049 mm²), and 400 µm (0.126 mm²) diameter circular micropattern arrays to generate forebrain and spinal neuroepithelial tissues (FIGS. 6A-6B and 6D-6E). After 5 days of culture in the absence or presence of 10 µM ROCK inhibitor, manual analysis of rosette emergence revealed stark differences in the emergent behavior of forebrain vs. spinal neuroepithelial tissues. Similar to our previous results, the efficiency of singular neural rosette emergence for forebrain tissues peaked at 85% on 250 µm (0.049 mm²) diameter circular micropatterns (FIG. 6C). However, in the presence vs. absence of ROCK inhibitor, the efficiency curve shifted leftward inducing singular rosette emergence in 75% vs. 0% of 150 µm (0.018 mm²), 89% vs. 50% of 180 µm (0.025 mm²), 87% vs. 58% of 200 µm (0.031 mm²), and 11% vs. 85% of 250 µm (0.049 mm²) diameter forebrain neuroepithelial tissues, respectively. In comparison, singular neural rosette emergence within spinal neuroepithelial tissues peaked at 73.5% on 150 µm (0.018 mm²) diameter micropatterns, and the presence of ROCK inhibitor completely abolished their ability form neural rosettes (FIG. 6F). Of note, NEC density within forebrain vs. spinal tissues of a given micropattern size and in the presence vs. absence of ROCK inhibitor did not vary significantly (FIG. 7).

Considering our previous experiments, the optimal morphology for single neural rosette emergence in forebrain and spinal neuroepithelial tissues is 200-250 μm (0.031-0.049 mm$^2$) and 150 μm (0.018 mm$^2$)diameter circular micropatterns respectively. The physical size of emergent neural rosettes is not conserved across tissues of increasing area (FIGS. 6C and 6E). Hence, the micropatterned tissue morphology does not instruct rosette morphogenesis, but restricts tissue area to statistically favor emergence of a single rosette in accordance with innate NEC properties. Since ROCK inhibition downregulates actin polymerization and acto-myosin contraction (39), our results suggest that decreasing the contractility of forebrain NECs reduces the length scale over which the cells can effectively polarize to evoke a rosette 355 structure, i.e., 250 μm vs. 150/180/200 μm in 0 vs. 10 μM Rock inhibitor. This further suggests that forebrain vs. spinal NECs can generate more contractile force since singular rosette emergence peaks in larger forebrain, i.e., 250 μm (0.049 mm$^2$) diameter, versus smaller spinal, i.e., 150 μm (0.018 mm$^2$) diameter, circular tissues. The ability of 10 μM Rock inhibitor to only partially diminish vs. fully eliminate the rosette formation capacity of forebrain vs. spinal NECs also supports this ranking of contractility. These results provide the first evidence that NEC biomechanical properties vary based on their regional patterning. They also demonstrate the necessity of customizing the micropatterned neuroepithelial tissue morphology to efficiently induce singular rosette emergence based on the cell's regional phenotype.

Figure 8A:
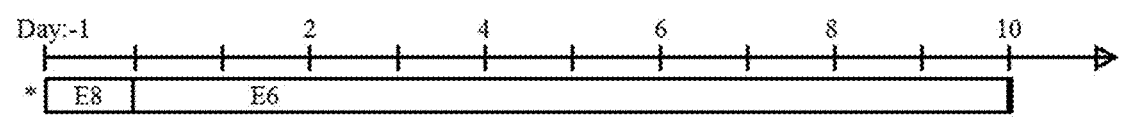
FIGS. 8A-8B demonstrate ECM deposition by neuroepithelial tissues upon extended culture. (A) Schematic timeline for extended culture of forebrain NECs in standard well plate culture; seeding onto TCPS well plate indicated by (*). (B) Fluorescent image of D10 NECs depicting dense deposition of laminin at the neural rosettes' basal tissue boundary. Scale bar is 50 µm.
Figure 8B:
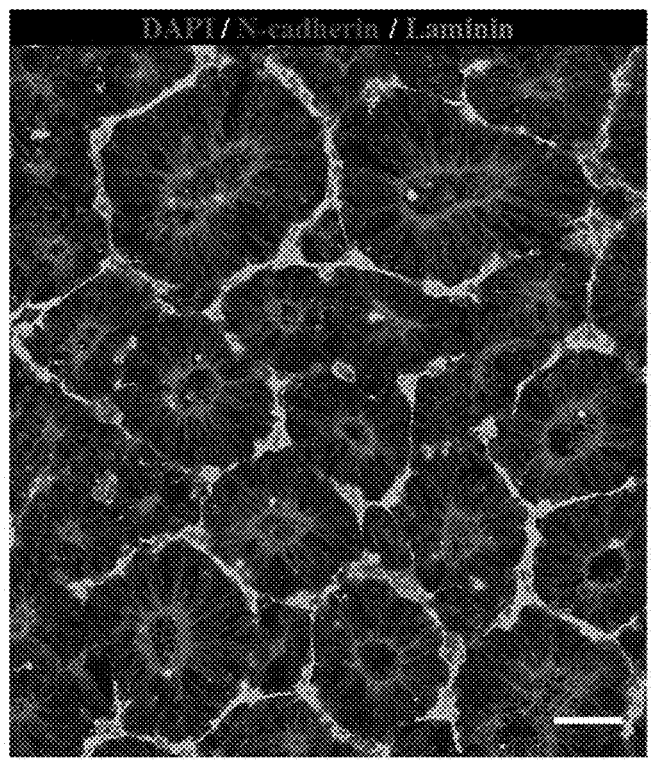
Figure 9A:
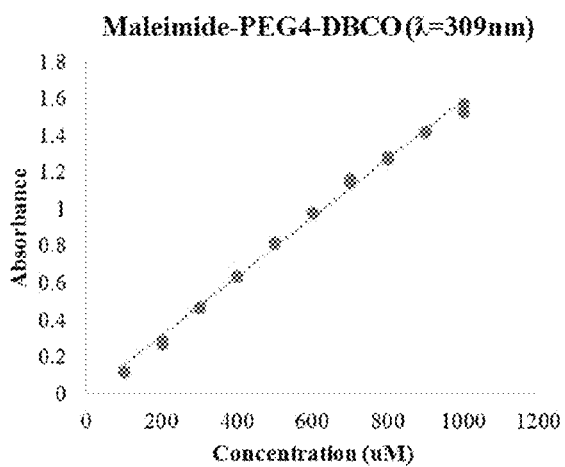
FIGS. 9A-9E presents characterization of FITC-HBP-DBCO bioconjugate synthesis. (A) Standard curve of maleimide-PEG4-DBCO crosslinker absorbance measured at 309 nm. (B) Standard curve of FITC-HBP absorbance measured at 495 nm. Size exclusion chromatography traces of FITC-HBP quantified from (C) 495 nm measurements and (D) a Micro-BCA assay, and (E) DBCO quantified from 309 nm elution in fractions containing the desired bioconjugate.
Figure 9B:
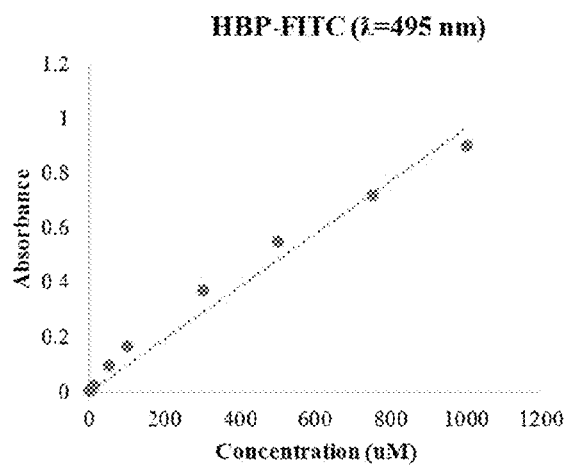
Figure 9C:
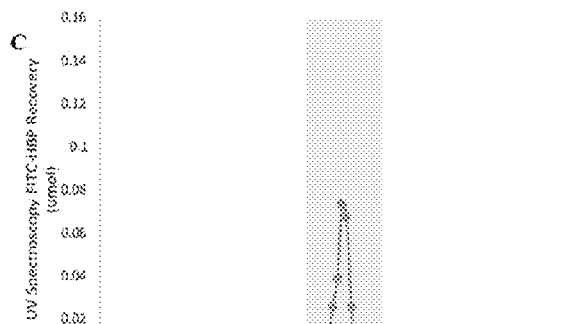
Figure 9D:
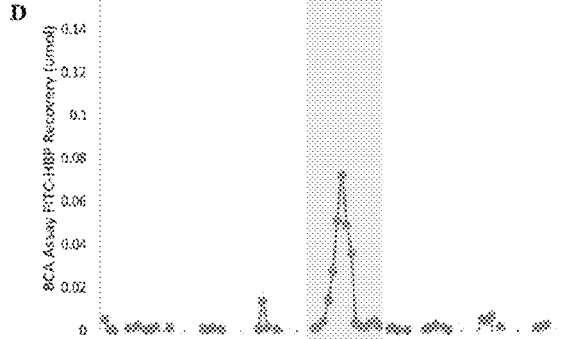
Figure 9E:
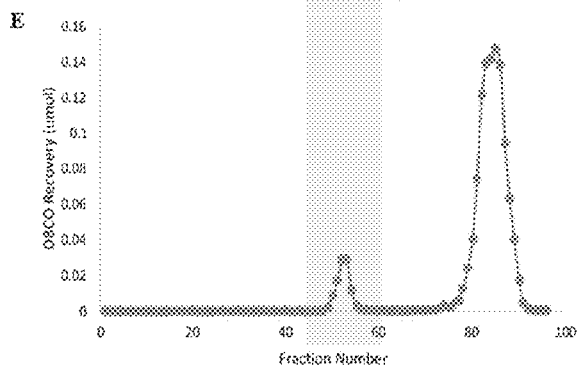
Figures 10A, 10B, 10C, 10D:
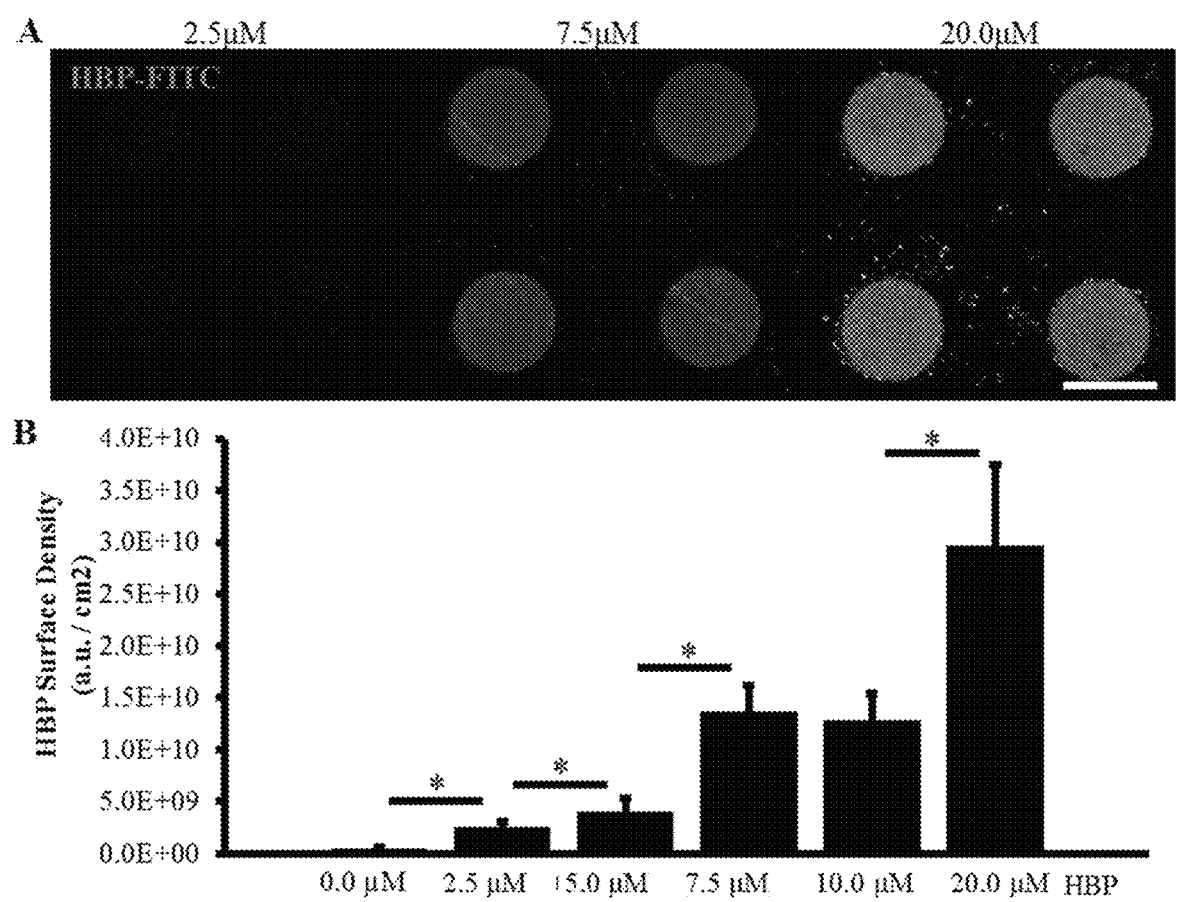
FIGS. 10A-10D demonstrates analysis of HBP-DBCO bioconjugate surface density and ECM adsorption. (A) Fluorescent images of FITC-HBP surface immobilization after 24 hour incubation of micropatterned substrates of 200 µm diameter circular and azide-functionalized PEG-MA posts backfilled with inert PEG brushes at various concentrations of FITC-HBP-DBCO. (B) Relative quantification of FITC-HBP surface density on micropatterned substrates, n=50 micropatterns per condition (technical replicates). (C) Fluorescent images of rhodamine-laminin adsorption on micropatterned substrates functionalized with various combinations of HBP. (D) Relative quantification of laminin adsorption on micropatterned substrates, n=50 micropatterns per condition (technical replicates). (*) indicates a significance of p<0.05 calculated using a One-way ANOVA, and error bars represent standard deviation. Scale bars are 200 um.

Singular Neural Rosette Cytoarchitecure is Maintained During Radial Tissue Outgrowth:

The importance of maintaining a singular neuroepithelium in early CNS development is evident given severe congenital disorders associated with breakdown (40, 41) or duplication (12, 14) of the neuroepithelial tube. Accordingly, we investigated whether the singular rosette structure induced within micropatterned neuroepithelial tissues would persist upon subsequent tissue growth and morphogenesis. Using our previously developed 'clickable' polyethylene glycol (PEG) brush chemistry (26, 28), we synthesized array substrates that could be actuated to release the micropatterned tissues from their confinement and permit radial tissue outgrowth. In our prior publication, tissue outgrowth was enabled by in situ conjugation of -RGD peptide bioconjugates to the microarray's PEG brushes. However, this caused aberrant migration of single cells away from the neuroepithelial tissues instead of a more coordinated, biomimetic radial tissue expansion (26). Therefore, we explored whether a clickable bioconjugate containing a heparin binding peptide (-CGTYRSRKY) derived from Fibroblast growth factor-2 would mediate a more gradual tissue expansion. This was posited based on the fact that the heparin binding peptide (HBP) is unable to directly promote cell migration via integrin binding but could immobilize heparin sulfate proteoglycan-bound ECM proteins (e.g., Laminin) secreted at the neuroepithelial tissues' basal aspect upon extended culture (42) (FIGS. 8A-8B).

To evaluate feasibility of our proposed substrate design, micropatterned arrays with reactive, 200 μm (0.031 mm$^2$) diameter, circular PEG brushes were fabricated and functionalized via an overnight incubation in cell culture media containing 0 to 20 μM FITC HBP conjugated to a Malemide-PEG4-DBCO linker (FIGS. 9A-9E and FIGS. 10A-10B). Using confocal microscopy, a direct correlation between fluorescence from immobilized FITC-HBP and the incubation media concentration was observed with culture media containing 20 μM FITC-HBP-DBCO bioconjugate providing maximal surface density. Then, we tested whether HBP-presenting PEG brushes could sequester ECM proteins. Substrates modified with cell culture media containing 0, 5, 10, and 20 μM HBP DBCO bioconjugate were subsequently incubated overnight in media containing 10 μM NHS-rhodamine tagged Laminin, which was isolated from a mouse sarcoma and likely co-bound with heparin sulfate proteoglycans. Imaging revealed a consistent increase in rhodamine fluorescence directly correlated with increasing surface densities of HBP and saturating on substrates modified with culture media containing 10 HBP-DBCO bioconjugate (FIGS. 10C-10D). Thus, PEG-brushes modified in situ with 10 μM HBP-DBCO bioconjugate are capable of immobilizing Laminin proteins, and potentially a diverse cadre of basement membrane ECM proteins that bind heparin sulfate proteoglycans (43).

Figures 11A, 11B, 11C, 11D, 11E, 11F, 11G:
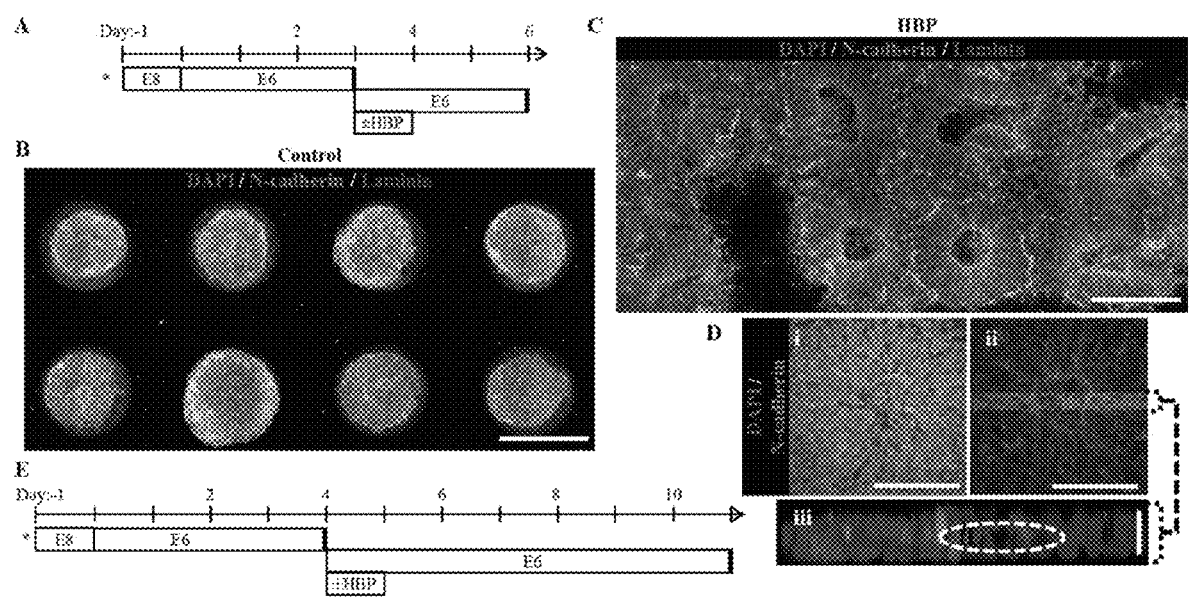
FIGS. 11A-11G demonstrate micropatterned neuroepithelial tissue outgrowth on clickable, HBP-presenting substrates. (A) Schematic for derivation and HBP-mediated expansion of forebrain neuroepithelial tissues on chemically-modified micropattern arrays of 200 µm diameter circles with 400 µm center-to-center spacing. (B) Image of singular neural rosette emergence within D6 neuroepithelial tissues on inert PEG-MA substrates not functionalized by HBP-DBCO bioconjugates. (C) Image of singular neural rosette expansion within D6 neuroepithelial tissues on reactive PEG-MA substrates functionalized with HBP-DBCO bioconjugates. The tissues show radial expansion and deposition of a Laminin+ basement membrane analogous to extended neuroepithelial culture in well plates as shown in FIGS. 8A-8B. Bright-field, time course images of radial tissue expansion are shown in FIGS. 12A-12B. (D) (i) Magnified image of expanded neuroepithelial of forebrain neural tissues on chemically-modified micropattern arrays of 200 µm diameter circles with 800 µm center-to-center spacing. (F) Image of singular neural rosette tissue outgrowth and neuronal differentiation on HBP-functionalized substrates at day 11. (G) (i) Magnified image of the neuroepithelial center of expanded neural tissues with (ii) the highlighted 3D cross-section and profile view of (iii) nuclei, (iv) Pax6+ core, and (v) primarily peripheral Tuj 1+ neuronal processes; white dotted lines indicate hollow polarization cavity. Scale bars are (B, C, F) 200 µm, (D(i,ii), G(i,ii)) 100 µm, and (D(iii), G(iii,iv,v)) 20 µm.
Figures 12A, 12B:
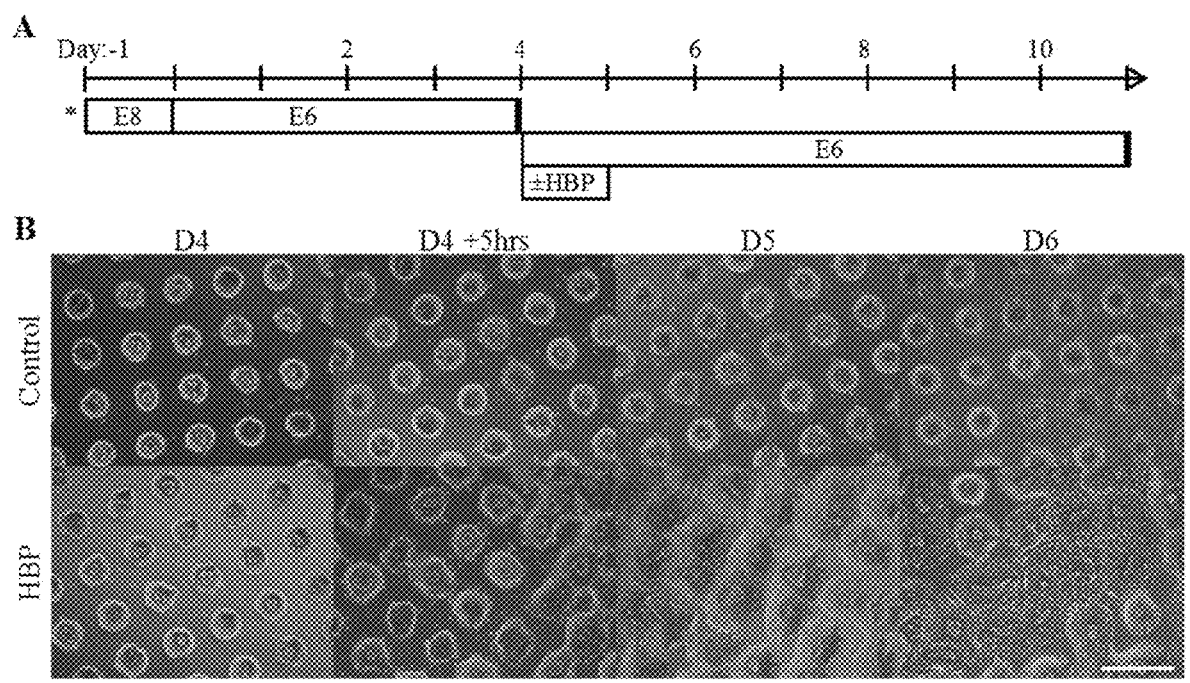
FIGS. 12A-12B demonstrate time course imaging of patterned NEC tissue outgrowth. (A) Schematic timeline for derivation and HBP-mediated expansion of forebrain NEC tissues on 200 μm circular micropatterned arrays with 40 μm center-to center spacing and intervening reactive PEG-MA brushes. (*) indicates when hPSCs are seeded on micropatterned substrates. (B) Representative brightfield images of neuroepithelial tissue expansion directly following in situ surface functionalization with HBP. Scale bar is 400 μm.

Next, neuroepithelial tissue outgrowth was tested on both inert and reactive PEG-grafted substrates micropatterned to display arrays of 200 μm (0.031 mm$^2$) diameter circular culture regions with 400 μm center-to-center spacing. The substrates were subsequently coated with MATRIGEL™ to deposit ECM proteins on the 200 μm diameter culture regions. Pax6– D$^-$1 hESCs were seeded onto the substrates at 100,000 cells/cm$^2$ and maintained in E6 culture for 3 days, at which point the media was supplemented with 10.0 μM HBP DBCO bioconjugate for 24 hours on both inert and reactive microarray substrates. After 3 additional days of culture, the tissues were fixed and stained for N-cadherin and Laminin (FIG. 11A). Inert control PEG brushes predictably maintained the restricted singular rosette tissue morphology for the culture duration (FIG. 11B). In contrast, on reactive substrates modified in situ with HBP-DBCO bioconjugates, the tissues expanded as a coherent, multilayered structures maintaining a singular neuroepithelium and eventually intersecting with neighboring tissues. Also, they displayed basal deposition of laminin resembling the developing neural tube's basal lamina (FIGS. 11C-11D and FIGS. 12A-12B). To prevent inhibition of tissue outgrowth, the experiment was repeated on reactive micropatterned arrays with 200 μm (0.031 mm$^2$) diameter circular regions with larger 800 μm center-to-center spacing. The in situ modification occurred on Day 4 of E6 culture, and microarrays were fixed and stained after an additional 7 days of culture (FIG. 11E). These tissues also maintained a singular Pax6+ neuroepithelium throughout the culture period that morphed into a 3-D hemispherical structure with a central cavity and Tuj 1+ neuronal cells residing at the tissues periphery (FIGS. 11F-11G). These results indicate that controlled induction of singular rosette emergence upon organotypic neural tissue formation will persist throughout subsequent stages of morphogenesis, thereby enabling formation of a biomimetic nascent CNS tissue cytoarchitecture.

Discussion

Neural organoid technology has enabled unprecedented in vitro recapitulation of biomimetic, human CNS tissue microenvironments. This is currently being used to develop novel personalized neurological disease modeling platforms (4, 44, 45). However, while impressive in their extent of ex vivo morphogenesis, the spontaneous and cell-intrinsic emergent properties that enable organoid formation also currently limited their wide-scale implementation due to the lack of reproducibility in their macroscale cytoarchitecture and cellular composition. In essence, we now have a glimpse of the neural organoid's potential, but do not understand the processes that govern their morphogenesis well enough to precisely engineer their formation (46). Here, we have melded organoid technology with a biomaterial culture platform to elucidate biophysical parameters that control the genesis of human neural organoid morphogenesis, i.e., polarized neural epithelium formation.

Over the past decade, scientists have generated human neural organoids of the cerebral cortex (2), retina (3), forebrain (4, 17), midbrain (47), and cerebellum (48) with both neuronal and glial cellular constituents (49). However, a consistent limitation in creating reproducible and biomimetic neural organoid anatomy at the macroscale is the random formation of multiple polarized neuroepithelial regions, a.k.a. rosettes, which can each act as independent morphogenesis centers. Using micropatterned culture substrates, we have demonstrated that enforcing a 200-250 um forebrain and 150 um spinal, circular neuroepithelial tissue morphology optimally induces formation of a singular rosette cytoarchitecture with 80-85% and 73.5% efficiency, respectively. Our results indicate that these biophysical parameters for reproducible induction of a biomimetic, neural tube-like cytoarchitecture are dependent on local cell density, acquisition of Pax6 expression, and cell non-autonomous biomechanical properties such as contractility. Furthermore, we have shown that the singular neural rosette cytoarchitecture can be maintained upon subsequent tissue morphogenesis, indicating that initial constraint of tissue morphology in accordance with these identified length scales could be a generalizable approach to engineering human neural organoids with standardized nascent CNS tissue cytoarchitecture. However, we acknowledge that our micropatterned tissues do morph from 2-D monolayers to 3-D hemispherical tissues (FIGS. 11A-11G) and, therefore, our identified optimal tissue morphology parameters may not be precisely conserved for organoids initially formed as 3-D cell aggregates.

While organoids can be used to generate novel humanoid disease models, their ability to recapitulate developmental morphogenesis ex vivo and within a human genomic background also provides unique opportunities to investigate mechanisms that orchestrate early human development (21, 22). In efforts to develop a unified approach for inducing singular neural rosette emergence within neuroepithelium patterned to any CNS rostrocaudal region, we discovered that the biomechanical properties of Pax6+/N-cadherin+ NECs of the dorsal forebrain differed from those of the ventral spinal cord. Forebrain NECs appear to be able to form singular neural rosettes within tissue of larger circular dimensions that spinal NECs because of their increased contractility (FIGS. 6A-6F). This would seem to correlate with the significantly larger dimensions of forebrain ventricles versus the spinal cord's central canal, and could represent a unique axis between the biochemical morphogens and biomechanical properties that govern CNS morphogenesis. While our conclusions are based on observations from correlated perturbations of ROCK activity and not direct contractility measurements, our experimental paradigm does provide a unique platform for further definitive analysis of the interplay between biochemical and biomechanical factors that govern this facet of human CNS morphogenesis. To our knowledge, there is no other experimentally tractable means by which such phenomena can be investigated within a human genomic background.

The ability to reproducibly engineer the nascent neuroepithelial cytoarchitecture of neural organoids in a high-throughput arrayed format could have significant implications for future advanced biomanufacture of the neural organoid platform. The 3-D nature of organoids grown in suspension culture provides constituent cells with a biomimetic tissue context. However, suspension organoids grow to millimeters in diameter, limiting real-time analysis of internal morphogenesis processes using traditional imaging modalities. While our microarrayed neural tissues initiate as a 2-D monolayer, they quickly become multilayered and definitively 3-D, i.e., >4 cell layers thick, within 4 days of culture and continue to increase in thickness upon expended culture (FIGS. 3A-3F and FIGS. 11A-11G). Thus, the biophysical (50) and electrophysiological (51) benefit of 3-D organoids may still apply within our engineered neural tube slides. Our arrayed approach enables constant monitoring throughout their morphogenesis process using confocal microscopy. Furthermore, the stratified microscale cytoarchitecture observed in regions of cortical, retinal, cerebellar, and cerebral organoids may also be achievable upon further modification of our culture substrates to provide continual but expanding confinement as the arrayed tissues outgrow radially (26, 52). If achievable, then the substrate parameters elucidated in this study could serve as a basis for generating an engineered well-plate platform to which scientists could simply add their patient-specific hPSCs or Pax6-hPSC derivatives (FIGS. 3A-3F and FIGS. 4A-4E), follow an in situ modification protocol (FIGS. 11A-11G), and allow the engineered culture substrate to instruct reproducible growth of high density arrays of neural organoid tissues. This would facilitate broad dissemination of the neural organoid platform as well as real-time microscopic investigation of the organoid's morphogenesis and terminal structure.

Experimental Procedures

Micropatterned Substrate Fabrication:

Micropatterned substrates were fabricated using a combination of previously published methods[26]. Poly(dimethyl siloxane) (PDMS) stamps with arrays of post- and microwell features were generated as relief molds of silicon wafers. The wafers were designed in AutoCAD ad purchased from FlowJEM (see flowjem.com on the world wide web). PDMS stamps were coated with w-mercaptoundecyl bromoisobutyrate (2 mM in 100% ethanol), dried under inert gas, and then brought in conformal contact with glass coverslips coated with 180 nm Au atop 30 nm Ti. Micropatterned slides were then incubated in 100% ethanol for 10 minutes, prior to being dried under nitrogen and transferred to a Schlenk flask under vacuum. A solution of either poly(ethylene glycol) methyl ether methacrylate (PEG-MEMA) or poly(ethylene glycol)methacrylate (PEG-MA) macromonomer (Sigma Aldrich), water, methanol (Thermo Fisher), copper(II) bromide (Sigma Aldrich), and 2',2-bipyridine (Sigma Aldrich) was degassed and transferred to the reaction flask. Surface-initiated atom-transfer radical-polymerization (SI-ATRP) of PEG polymers was initiated by injection of L-ascorbic acid (Sigma Aldrich) in deionized water into the reaction flask. ATRP was allowed to continue for 16 hours to generate micropatterned PEG brushes. Polymerization was terminated via addition of air, followed by rinsing with ethanol and water before drying under inert gas. In a sterile hood, the substrates were rinsed five times with sterile PBS (Thermo Fisher) and transferred to individual wells of a 12-well tissue-culture polystyrene (TCPS) plate, where they were rendered cell-adhesive through adsorption of 0.083 mg/mL MATRIGEL™ (WiCell) in DMEM/F-12 (Thermo Fisher) via overnight incubation at 37° C.

Generation of Micropatterned Forebrain Neural Tissues:

WA09 or HUES3 Hb9::GFP hESCs were maintained in Essential 8 medium (E8) on MATRIGEL™-coated TCPS plates and routinely passaged with Versene (Thermo Fisher). NEC derivation from hPSCs was performed in accordance with the E6 protocol (23). To generate NEC-derived micropatterned tissues at various stages of neural derivation, cells were first rinsed with PBS, dissociated with Accutase (Thermo Fisher) for 5 minutes at 37° C., and collected via centrifugation at 1000 rpm for 5 minutes. Singularized NECs were re-suspended in E6 media with 10 µM ROCK inhibitor (Y27632; R&D Systems) and seeded onto micropatterned substrates at 75,000 cells/cm$^2$ in 2 mL of media per well. The following day the media was replaced with 2 mL of E6 media and 50% media changes were performed daily thereafter. Alternatively, to generate hPSC-derived micropatterned tissues, hPSC cultures at ~85% confluency were rinsed with PBS, dissociated with Accutase for 5 minutes at 37° C. and collected via centrifugation at 1000 rpm for 5 minutes. Singularized hPSCs were then suspended in E8 media with 10 µM ROCK inhibitor and seeded onto micropatterned substrates at 100,000 cells/cm$^2$ in 2 mL of media per well. The following day the media was replaced with 2 mL of E6 media and 50% media changes were performed daily thereafter.

Generation of Micropatterned Spinal Cord Neuroepithelial Tissues:

Caudalization of hPSC-derived cultures to generate micropatterned neuroepithelial tissues of the cervical/thoracic spinal cord was performed using a modified version of the deterministic HOX patterning protocol (36). Human PSCs were dissociated with Accutase and seeded onto MATRIGEL™-coated, 6-well TCPS plates at 150,000 cells/cm$^2$ in E8 media comprising 10 µM ROCK inhibitor. The following day the media was switched to E6 media for another 24 hours of culture, after which the media was supplemented with 200 ng/mL FGF8b (R&D Systems) to initiate differentiation into a NMP phenotype. Following 24 hours in E6+FGF8b media, the cells were dissociated with Accutase for 1:45 minutes and seeded onto TCPS plates at a 1:1.5 well ratio in E6 media comprising 200 ng/mL FGF8b, 3 µM CHIR (R&D Systems), and 10 µM ROCK inhibitor. The cells were allowed to remain in E6+FGF8b+CHIR+ROCK for 48 hrs before the media was switched to E6+FGF8b+CHIR. After 24 hrs, the NMPs were dissociated with Accutase for 5 minutes and seeded onto micropatterned substrates at 150,000 cells/cm$^2$ or 250,000 cells/cm$^2$ in E6 media comprising 10 µM ROCK inhibitor. Six hours later, the media was supplemented with 1 µM Retinoic Acid (RA, R&D Systems), and 10 µM ROCK inhibitor to initiate transition to a neuroepithelial cell type. The next day the media was switched to E6 media with 1 µM RA, and 50% media changes were performed every 24 hrs for the next 2 days. Then, the media was supplemented with 1 µM RA, 2 µg/mL Sonic hedgehog, and 2 µM Purmorphomine (Shh, PM; R&D Systems) to induce ventralization. To further enhance ventralization, a 6-hour boost in Wnt signaling via media supplementation with 6 µM CHIR was applied either immediately before subculture or 72 hrs after cell seeding onto micropatterned substrates but prior to RA+Shh+PM exposure. The neuroepithelial cells were maintained in E6+RA+Shh+PM with 50% media changes daily.

Immunocytochemistry and Microscopy:

Micropatterned tissues were rinsed with PBS and fixed with 4% paraformaldehyde (PFA, Sigma Aldrich) in PBS for 10 minutes at room temperature. Following three rinses with phosphate buffered saline (PBS), the micropatterned substrates were blocked and permeabilized in PBS with 5% Donkey Serum and 0.3% Triton X-100 (TX100; Thermo Fisher) (PBS-DT) for 1 hour at room temperature. Next, the tissues were incubated with primary antibodies diluted in PBS-DT for 2 hours at room temperature or overnight at 4° C. Then, the substrates were rinsed in PBD-DT 3 times for 15 minutes each. Secondary antibodies were diluted in PBS-DT and exposed to the tissues for 1 hour at room temperature. Tissue nuclei were subsequently stained with 300 nM 4',6-diamidino-2-phenyl-lindoldihydrochloride (DAPI, Sigma Aldrich) for 30 minutes followed by three 15 minute PBS washes. The micropatterned substrates were mounted on glass coverslips using Prolong Gold Antifade Reagent (Thermo Fisher). Live images of micropatterned tissues were obtained using a Nikon TS100 microscope with a ME600L camera and all fluorescence images were obtained using a Nikon MR confocal microscope. CellProfiler (BROAD Institute) was used to segment and quantify immunostained images to determine a differentiation efficiency based on the percentage of nuclei stained positively for a specific protein marker.

Figures 14A, 14B, 14C, 14D:
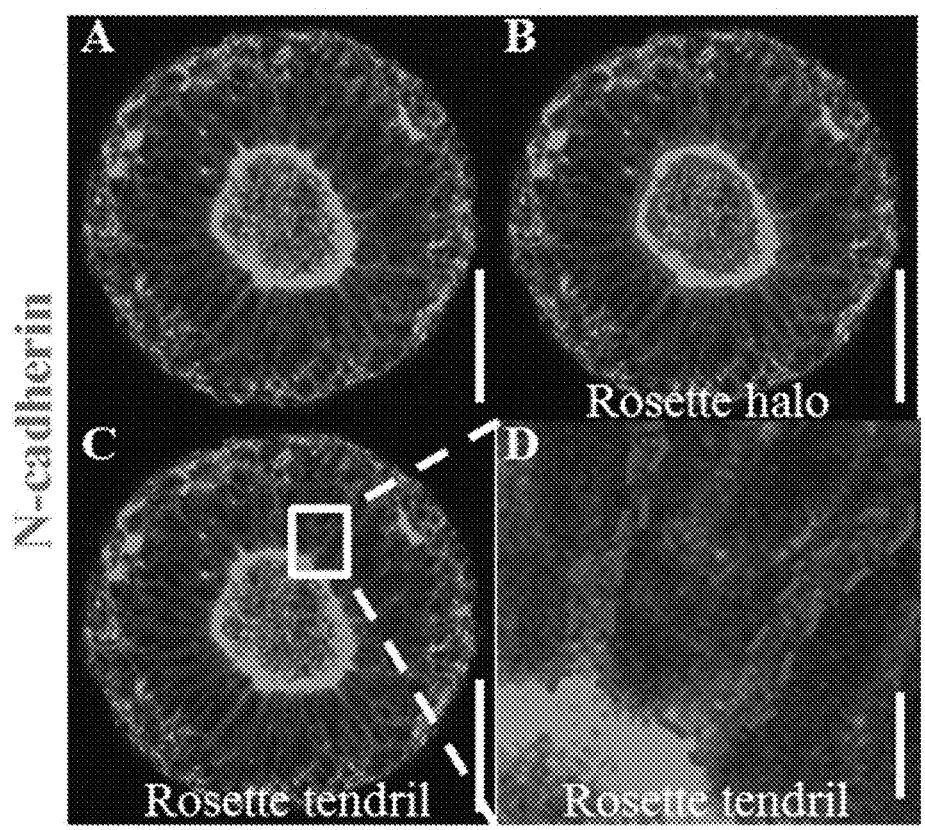
FIGS. 14A-14D are images demonstrating application of automated image analysis descriptors for neuroepithelial tissues. (A) Maximum intensity projection of micropatterned neuroepithelial tissue immunostained for N-cadherin. (B) Outlined region identified as N-cadherin halo boundary for use in area, radius, and eccentricity measurements. (C) Selected box region (white) that proceeds around N-cadherin ring boundary to calculate tendril angle 1 and 2 and tendril density 1 and 2. (D) Magnification of box region with dotted red outline of N-cadherin stained tendrils, which are indicative of cell-to-cell membrane interfaces. Scale bars are (A, B, C) 100 μm and (D) 10 μm.

Neuroepithelial Tissue Image Analysis Algorithm and Descriptor Definitions:

An automated workflow for quantitative analysis of micropatterned neuroepithelial tissue morphology (see FIGS. 14A-14D) was generated using MATLAB® (MathWorks). We first defined morphological characteristics of polarized neuroepithelial tissues. Neural rosettes in micropatterned tissues were identified by the presence of a coherent N-cadherin ring structure described in algorithm logic as halo (FIG. 14B). Neural rosette morphology was further defined by the density of N-cadherin localization along constituent cell membranes with apico-basal polarity, described here as tendrils (FIGS. 14C-14D). Areas of NECs that exhibited punctate localization of N-cadherin absent the requisite ring structure and corresponding apico basal polarity were classified as polarization foci (see FIG. 1F). Next, descriptors were established for variance in size and shape of zones of N-cadherin localization defined in the algorithm as measures of polarization area, fitted ellipse major axis length, and eccentricity. Further, a halo intensity ratio was applied to N-cadherin ring structures as a measure of the ratio of internal and external fluorescence intensity across the boundary of N-cadherin localization. Lastly, the apico-basal polarity of constituent cells surrounding apical N-cadherin localization was characterized as a measurement of cell membrane alignment angle compared to the tangent of the N-cadherin boundary (i.e., tendril angle incoherence 1 & 2). This measure was to be analyzed in conjunction with a measure of the tendril 1 & 2 density. Continuous variation in the above descriptors was accounted for to allow discontinuous response in classification of polarizing NECs as polarization foci or neural rosettes.

Conducting Automated Analysis of Neuroepithelial Tissue Images:

Automated analysis of NEC polarization and neural rosette emergence was performed using 3D image stacks of single micropatterned neural tissues fluorescently stained for nuclei and N-cadherin. 3D image stacks were compiled from 7 vertically segmented image acquisitions at 1.5 µm intervals using a 60× objective with 1024×1024 pixel resolution. Entire datasets were analyzed in batch fashion using the custom MATLAB® program described above. First, images were pre-processed by applying a median filter to the maximum intensity projection. Next, regions of dense N-cadherin staining were identified as discrete blobs (i.e., polarization foci) using the process of maximally stable extremal regions (MSER) (53). After applying a smoothing filter, polarization foci area, eccentricity, and major axis of a fitted ellipse ('radius') was calculated for each region detected. Foci with area less than 176 µm$^2$ were excluded from further processing. To the mean image projection with a median filter, the location and intensity ratio of the N-cadherin halo was assessed. Identification of the halo served to both evaluate the coherence of the N-cadherin ring and establish a boundary for assaying arrangement of tendrils in relation to the halo. Once the halo boundary was established, the tendril density and tendril angle were measured by sampling 20 pixel squares at various points around the foci epicenter at a distance of 1.5× (1) and 2× (2) the radius of the foci. Within each sampling area, pixel intensity was assayed to measure density of tendrils and a gradient orientation filter was used to calculate the directionality of tendrils relative to the halo boundary. For each foci identified, values for tendril angle 1 & 2 and tendril density 1 & 2 were calculated as averages from all points sampled. Collectively, these eight descriptors comprised an image descriptor vector.

REFERENCES

[1] J. A. Thomson, Embryonic Stem Cell Lines Derived from Human Blastocysts, Science. 282 (1998) 1145-1147. doi:10.1126/science.282.5391.1145.

[2] M. Eiraku, K. Watanabe, M. Matsuo-Takasaki, M. Kawada, S. Yonemura, M. Matsumura, et al., Self-organized formation of polarized cortical tissues from ESCs and its active manipulation by extrinsic signals, Cell Stem Cell. 3 (2008) 519-532. doi:10.1016/j.stem.2008.09.002.

[3] T. Nakano, S. Ando, N. Takata, M. Kawada, K. Muguruma, K. Sekiguchi, et al., Self-Formation of Optic Cups and Storable Stratified Neural Retina from Human ESCs, Cell Stem Cell. 10 (2012) 771-785. doi:10.1016/j.stem.2012.05.009.

[4] M. A. Lancaster, M. Renner, C.-A. Martin, D. Wenzel, L. S. Bicknell, M. E. Hurles, et al., Cerebral organoids model human brain development and microcephaly, Nature. 501 (2013) 373-379. doi:10.1038/nature12517.

[5] C. L. Watson, M. M. Mahe, J. Múnera, J. C. Howell, N. Sundaram, H. M. Poling, et al., An in vivo model of human small intestine using pluripotent stem cells, Nat. Med. 20 (2014) 1310-1314. doi:10.1038/nm.3737.

[6] M. A. Lancaster, J. A. Knoblich, Organogenesis in a dish: modeling development and disease using organoid technologies, Science. 345 (2014) 1247125-1247125. doi:10.1126/science.1247125.

[7] Y. Sasai, Next-generation regenerative medicine: organogenesis from stem cells in 3D culture, Cell Stem Cell. 12 (2013) 520-530. doi:10.1016/j.stem.2013.04.009.

[8] M. J. Workman, M. M. Mahe, S. Trisno, H. M. Poling, C. L. Watson, N. Sundaram, et al., Engineered human pluripotent-stem-cell-derived intestinal tissues with a functional enteric nervous system, Nat. Med. 23 (2017) 49-59. doi:10.1038/nm.4233.

[9] C. R. Marti-Figueroa, R. S. Ashton, The case for applying tissue engineering methodologies to instruct human organoid morphogenesis, Acta Biomaterialia. 54 (2017) 35-44. doi:10.1016/j.actbio.2017.03.023.

[10] M. A. Lancaster, N. S. Corsini, T. R. Burkard, J. A. Knoblich, Guided self-organization recapitulates tissue architecture in a bioengineered brain organoid model, bioRxiv. (2016).

[11] J. Zhang, G. J. Woodhead, S. K. Swaminathan, S. R. Noles, E. R. McQuinn, A. J. Pisarek, et al., Cortical neural precursors inhibit their own differentiation via N-cadherin maintenance of beta-catenin signaling, Developmental Cell. 18 (2010) 472-479. doi:10.1016/j.devcel.2009.12.025.

[12] S. Testoni, A. Grandis, A. Diana, Imaging diagnosis—ultrasonographic diagnosis of diplomyelia in a calf, Veterinary Radiology . . . (2010). doi:10.1111/j.1740-8261.2010.01717.x.

[13] S. B. COGLIATTI, Diplomyelia—Caudal Duplication of the Neural-Tube in Mice, Teratology. 34 (1986) 343-352. doi:10.1002/tera.1420340314.

[14] R. Spencer, Theoretical and analytical embryology of conjoined twins: part I: embryogenesis, Clin Anat. 13 (2000) 36-53. doi:10.1002/(SICI)1098-2353(2000)13:1<36::AID-CA5>3.0.CO; 2-3.

[15] C.-T. Lee, J. Chen, A. A. Kindberg, R. M. Bendriem, C. E. Spivak, M. P. Williams, et al., CYP3A5 Mediates Effects of Cocaine on Human Neocorticogenesis: Studies using an In Vitro 3D Self-Organized hPSC Model with a Single Cortex-Like Unit, Neuropsychopharmacology. 42 (2017) 774-784. doi:10.1038/npp.2016.156.

[16] S. C. Zhang, M. Wernig, I. D. Duncan, O. Brustle, J. A. Thomson, In vitro differentiation of transplantable neural precursors from human embryonic stem cells, Nature Biotechnology. 19 (2001) 1129-1133. doi:10.1038/nbt1201-1129.

[17] M. A. Lancaster, N. S. Corsini, T. R. Burkard, J. A. Knoblich, Guided self-organization recapitulates tissue architecture in a bioengineered brain organoid model, bioRxiv. (2016). doi:10.1101/049346.

[18] A. Meinhardt, D. Eberle, A. Tazaki, A. Ranga, M. Niesche, M. Wilsch-Brauninger, et al., 3D reconstitution of the patterned neural tube from embryonic stem cells, Stem Cell Reports. 3 (2014) 987-999. doi:10.1016/j.stemcr.2014.09.020.

[19] A. Ranga, S. Gobaa, Y. Okawa, K. Mosiewicz, A. Negro, M. P. Lutolf, 3D niche microarrays for systems-level analyses of cell fate, Nature Communications. 5 (2014) 4324. doi:10.1038/ncomms5324.

[20] Y. Shi, P. Kirwan, J. Smith, H. P. C. Robinson, F. J. Livesey, Human cerebral cortex development from pluripotent stem cells to functional excitatory synapses, Nat. Neurosci. 15 (2012) 477-86-S1. doi:10.1038/nn.3041.

[21] A. Warmflash, B. Sorre, F. Etoc, E. D. Siggia, A. H. Brivanlou, A method to recapitulate early embryonic spatial patterning in human embryonic stem cells, Nat Meth. 11 (2014) 847-854. doi:10.1038/nmeth.3016.

[22] F. Etoc, J. Metzger, A. Ruzo, C. Kirst, A. Yoney, M. Z. Ozair, et al., A Balance between Secreted Inhibitors and Edge Sensing Controls Gastruloid Self-Organization, Developmental Cell. 39 (2016) 302-315. doi:10.1016/j.devcel.2016.09.016.

[23] E. S. Lippmann, M. C. Estevez-Silva, R. S. Ashton, Defined human pluripotent stem cell culture enables highly efficient neuroepithelium derivation without small molecule inhibitors, Stem Cells. 32 (2014) 1032-1042. doi:10.1002/stem.1622.

[24] S. M. Chambers, C. A. Fasano, E. P. Papapetrou, M. Tomishima, M. Sadelain, L. Studer, Highly efficient neural conversion of human E S and iPS cells by dual inhibition of SMAD signaling, Nature Biotechnology. 27 (2009) 275-280. doi:10.1038/nbt.1529.

[25] X. Zhang, C. T. Huang, J. Chen, M. T. Pankratz, J. Xi, J. Li, et al., Pax6 is a human neuroectoderm cell fate determinant, Cell Stem Cell. 7 (2010) 90-100. doi:10.1016/j.stem.2010.04.017.

[26] J. Sha, E. S. Lippmann, J. McNulty, Y. Ma, R. S. Ashton, Sequential Nucleophilic Substitutions Permit Orthogonal Click Functionalization of Multicomponent PEG Brushes, Biomacromolecules. 14 (2013) 3294-3303. doi:10.1021/bm400900r.

[27] G. T. Knight, J. Sha, R. S. Ashton, Micropatterned, clickable culture substrates enable in situ spatiotemporal control of human PSC-derived neural tissue morphology, Chem. Commun. 51 (2015) 5238-5241. doi:10.1039/C4CC08665A.

[28] L. A. Davidson, R. E. Keller, Neural tube closure in *Xenopus laevis* involves medial migration, directed protrusive activity, cell intercalation and convergent extension, Development. 126 (1999) 4547-4556.

[29] T. Nishimura, H. Honda, M. Takeichi, Planar cell polarity links axes of spatial dynamics in neural-tube closure, Cell. 149 (2012) 1084-1097. doi:10.1016/j.cell.2012.04.021.

[30] C. M. Nelson, R. P. Jean, J. L. Tan, W. F. Liu, N. J. Sniadecki, A. A. Spector, et al., Emergent patterns of growth controlled by multicellular form and mechanics, Proc. Natl. Acad. Sci. U.S.a. 102 (2005) 11594-11599. doi:10.1073/pnas.0502575102.

[31] P. Philippidou, J. S. Dasen, Hox Genes: Choreographers in Neural Development, Architects of Circuit Organization, Neuron. 80 (2013) 12-34. doi:10.1016/j.neuron.2013.09.020.

[32] J. Briscoe, A. Pierani, T. M. Jessell, J. Ericson, A Homeodomain Protein Code Specifies Progenitor Cell Identity and Neuronal Fate in the Ventral Neural Tube, Cell. 101 (2000) 435-445. doi:10.1016/50092-8674(00)80853-3.

[33] J. R. Timmer, C. Wang, L. Niswander, BMP signaling patterns the dorsal and intermediate neural tube via regulation of homeobox and helix-loop-helix transcription factors, Development. 129 (2002) 2459-2472.

[34] E. S. Lippmann, C. E. Williams, D. A. Ruhl, M. C. Estevez-Silva, E. R. Chapman, J. J. Coon, et al., Deterministic HOX patterning in human pluripotent stem cell-derived neuroectoderm, Stem Cell Reports. 4 (2015) 632-644. doi:10.1016/j.stemcr.2015.02.018.

[35] R. Ashton, E. Lippmann, M. Estevez-Silva, Chemically defined differentiation of human pluripotent stem cells to hindbrain and spinal cord neural stem cells with defined regional identities, Protocol Exchange. (2015). doi: 10.1038/protex.2015.076.

[36] U. Nordstrom, E. Maier, T. M. Jessell, T. Edlund, An Early Role for Wnt Signaling in Specifying Neural Patterns of Cdx and Hox Gene Expression and Motor Neuron Subtype Identity, PLoS Biol. 4 (2006) e252. doi:10.1371/journal.pbio.0040252.sg003.

[37] E. Dessaud, L. L. Yang, K. Hill, B. Cox, F. Ulloa, A. Ribeiro, et al., Interpretation of the sonic hedgehog morphogen gradient by a temporal adaptation mechanism, Nature. 450 (2007) 717-720. doi:10.1038/nature06347.

The invention has been described in connection with what are presently considered to be the most practical and preferred embodiments. However, the present invention has been presented by way of illustration and is not intended to be limited to the disclosed embodiments. Accordingly, those skilled in the art will realize that the invention is intended to encompass all modifications and alternative arrangements within the spirit and scope of the invention as set forth in the appended claims.

We claim:

1. A method of producing a plurality of biomimetic neural tissues, comprising:

(a) seeding human pluripotent stem cells (hPSCs) in the presence of a Rho kinase inhibitor onto a micropatterned substrate, wherein the substrate is comprised of an array of micropatterned regions configured to instruct biomimetic neural morphogenesis of cells cultured thereon;

(b) culturing the seeded cells of (a) on the micropatterned substrate for a first culture period of about one to two days in the presence of a first neural differentiation base medium to obtain a first cell population, wherein the first neural differentiation base medium comprises a Rho kinase inhibitor;

(c) culturing the cells of (b) for a second culture period of about 2 to about 6 days under adherent culture conditions in a second neural differentiation base medium; and (d) producing a plurality of biomimetic neural tissues arrayed on the micropatterned substrate, wherein at least 75% of the arrayed tissues consist of a single polarized rosette structure in which at least 80% of cells of the structure are Pax6+/N-cadherin+ neuroepithelial cells.

2. The method of claim 1, wherein the first neural differentiation medium is a chemically defined medium comprising DMEM/F-12, ascorbic acid, sodium bicarbonate, selenium, insulin, transferrin, FGF2, and TGFβ1.

3. The method of claim 1, wherein the first neural differentiation medium is E8 medium.

4. The method of claim 1, wherein the second neural differentiation medium is a chemically defined medium comprising DMEM/F-12, ascorbic acid, sodium bicarbonate, selenium, insulin, transferrin.

5. The method of claim 1, wherein the second neural differentiation medium is E6 medium.

6. The method of claim 4, wherein second neural differentiation medium further comprises one or more of an FGF and an activator of β-catenin pathway signaling.

7. The method of claim 6, wherein the FGF is FGF2, FGF8a, FGF8b, FGF8f, FGF17, or FGF18.

8. The method of claim 6, wherein the activator of β-catenin pathway signaling is a GSK3 kinase inhibitor.

9. The method of claim 8, wherein the GSK3 kinase inhibitor is CHIR99021.

10. The method of claim 6, wherein the second neural differentiation medium comprises about 100 ng/ml to about 200 ng/ml FGF8b and about 3 µM to about 9 µM CHIR99021.

11. The method of claim 1, wherein the second culture period is about 5 days.

12. The method of claim 1, further comprising transiently exposing cells on the micropatterned substrate to an activator of Wnt/β-catenin signaling about 24-72 hours after seeding onto the micropatterned substrate.

13. The method of claim 1, further comprising, about 24-72 hours after seeding cells onto the micropatterned substrate, exposing the seeded cells to RA and Sonic Hedgehog (SHH) or a SHH signaling agonist for about 1 to about 5 days, whereby the polarized rosette structure comprises Olig2+ motor neurons progenitors (pMNs)

14. The method of claim 13, wherein the SHH signaling agonist is purmorphamine.

15. The method of claim 1, wherein hPSCs are seeded onto the micropatterned substrate at a density between about $75 \times 10^3$ cells/cm$^2$ and about $2.5 \times 10^5$ cells/cm$^2$.

16. The method of claim 1, wherein the micropatterned substrate has a bounded geometry having at least one dimension of about 150 µm to 800 µm.

17. The method of claim 1, wherein the micropatterned substrate has a circular bounded geometry having a diameter of about 150 μm to about 500 μm.

18. The method of claim 1, wherein the micropatterned substrate comprises a singular or plurality of polyethylene glycol (PEG) brushes or peptide-immobilizing PEG brushes arranged in a user-defined, bounded geometry.

* * * * *